US006951927B2

(12) United States Patent
Mayo et al.

(10) Patent No.: US 6,951,927 B2
(45) Date of Patent: Oct. 4, 2005

(54) PROTEINS WITH INTEGRIN-LIKE ACTIVITY

(75) Inventors: Stephen Mayo, Pasadena, CA (US); Julia Shifman, Pasadena, CA (US); Motomu Shimaoka, Brookline, MA (US); Timothy Springer, Newton, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/902,481

(22) Filed: Jul. 9, 2001

(65) Prior Publication Data

US 2003/0054440 A1 Mar. 20, 2003

Related U.S. Application Data

(60) Provisional application No. 60/216,600, filed on Jul. 7, 2000.

(51) Int. Cl.[7] .............................................. C07K 1/107
(52) U.S. Cl. ....................................... 530/395; 530/402
(58) Field of Search ....................... 424/185.1; 530/350, 530/395, 402

(56) References Cited

U.S. PATENT DOCUMENTS

| 6,188,965 B1 | 2/2001 | Mayo et al. |
| 6,269,312 B1 | 7/2001 | Mayo et al. |

FOREIGN PATENT DOCUMENTS

| WO | WO 95/17412 A1 | 6/1995 |
| WO | WO98/47089 A1 | 10/1998 |

OTHER PUBLICATIONS

Ngo J.T, Marks J., Karplus M., Computational complexity, protein structure prediction, and the Levinthal paradox in The Protein Folding Problem, ch.14, pp. 435–508, Birkhauser, 1994.*

Bowie JU, et al Deciphering the message in protein sequences: tolerance to amino acid substitutions. Science. 247(4948):1306–1310, 1990.*

Burgess et al Possible dissociation of the heparin–binding and mitogenic activities of heparin–binding growth factor–1 from its receptor–binding activities by site–directed mutagenesis of a single lysine residue. J Cell Biol. 111:2129–2138, 1990.*

Lazar E et al., Tranforming growth factor alpha: mutation of aspartic acid 47 and leucine 48 result in different biological activities. Mol Cell Biol. 8:1247–1252, 1988.*

Anderson, D.C. et al., "Contributions of the Mac–1 glycoprotein family to adherence–dependent granulocyte functions: structure–function assessments employing subunit–specific monoclonal antibodies." J Immunol. Jul. 1, 1986;137(1):15–27.

Aplin, A.E. et al., "Signal transduction and signal modulation by cell adhesion receptors: the role of integrins, cadherins, immunoglobulin–cell adhesion molecules, and selectins." Pharmacol Rev. Jun. 1998;50(2):197–263.

Arnaout, M.A. et al., "Amino acid sequence of the alpha subunit of human leukocyte adhesion receptor Mo1 (complement receptor type 3)." J Cell Biol. Jun. 1988;106(6):2153–8.

Betz, S.F. and DeGrado, W.F. "Controlling topology and native–like behavior of de novo–designed peptides: design and characterization of antiparallel four–stranded coiled coils." Biochemistry. May 28, 1996;35(21):6955–62.

(Continued)

*Primary Examiner*—Christina Chan
*Assistant Examiner*—Maher Haddad
(74) *Attorney, Agent, or Firm*—Robin M. Silva, Esq.; Renee M. Kosslak, Esq.; Dorsey & Whitney LLP.

(57) ABSTRACT

The invention relates to novel proteins with novel integrin and I domain activity and nucleic acids encoding these proteins. The invention further relates to the use of the novel proteins in the treatment of integrin related disorders.

TABLE 1

Computationally designed mutants[a]

| WT | ido1q | ido1r | ido2r | jlm2r |

TABLE 1

Computationally designed mutants[a]

| Backbone | Energy[b] | | | |
|---|---|---|---|---|
| 1ido | −1037 | −1145 | −1138 | −1116 | −678 |
| 1jlm | −1059 | +82758 | −840 | −1000 | −1086 |
| Position | Residues | | | |
| 139 | I | — | — | V | — |
| 153 | M | — | — | A | — |
| 156 | F | L | W | — | — |
| 157 | V | — | — | I | — |
| 160 | V | I | — | — | — |
| 199 | V | I | I | I | — |
| 215 | I | L | L | — | V |
| 219 | V | — | — | — | I |
| 223 | F | — | — | — | L |
| 238 | V | F | F | I | I |
| 239 | V | L | L | L | — |
| 240 | I | L | L | — | — |
| 259 | A | L | L | — | — |
| 269 | I | L | — | — | — |
| 271 | V | F | — | — | — |
| 287 | I | V | V | V | — |
| 299 | V | A | I | I | — |
| 308 | I | V | — | — | — |

[a]Mutants are named according to the structure that was stabilized (ido or jlm), the solvation potential used (1 or 2) and the definition of core residues (q or r).
[b]The lowest energy rotamer configuration was calculated for each sequence in the 1ido structure, and cross-calculated in the 1jlm structure, using both solvent potentials; all 50 core residues were used in order to make the q and r energies comparable. Results are shown for solvent potential 1 and were similar for potential 2. A severe clash of the sidechain of F271 with the backbone caused the high energy of the 1q sequence in the 1jlm structure; no movement of the backbone is allowed by the design method.

4 Claims, 12 Drawing Sheets

OTHER PUBLICATIONS

Corbi, A.L. et al., "cDNA cloning and complete primary structure of the alpha subunit of a leukocyte adhesion glycoprotein, p150,95." EMBO J. Dec. 20, 1987;6(13):4023–8.

Corbi, A.L. et al., "The human leukocyte adhesion glycoprotein Mac–1 (complement receptor type 3, CD11b) alpha subunit. Cloning, primary structure, and relation to the integrins, von Willebrand factor and factor B." J Biol Chem. Sep. 5, 1988;263(25):12403–11.

Dahiyat, B.I. and Mayo, S.L. "Protein design automation." Protein Sci. May 1996;5(5):895–903.

Dahiyat, B.I. et al., "Automated design of the surface positions of protein helices." Protein Sci. Jun. 1997;6(6):1333–7.

Dahiyat, B.I. and Mayo, S.L. "De novo protein design: fully automated sequence selection." Science. Oct. 3, 1997;278(5335):82–7.

Dahiyat, B.I. et al., "De novo protein design: towards fully automated sequence selection." J Mol Biol. Nov. 7, 1997;273(4):789–96.

Davignon, D. et al., "Lymphocyte function–associated antigen 1 (LFA–1): a surface antigen distinct from Lyt–2,3 that participates in T lymphocyte–mediated killing." Proc Natl Acad Sci U S A. Jul. 1981;78(7):4535–9.

Desjarlais, J.R. and Handel, T.M. "De novo design of the hydrophobic cores of proteins." Protein Sci. Oct. 1995;4(10):2006–18.

Diamond, M.S. et al., "The I domain is a major recognition site on the leukocyte integrin Mac–1 (CD11b/CD18) for four distinct adhesion ligands." J Cell Biol. Feb. 1993;120(4):1031–43.

Dustin, M.L. and Springer, T.A., "Lymphocyte function–associated antigen–1 (LFA–1) interaction with intercellular adhesion molecule–1 (ICAM–1) is one of at least three mechanisms for lymphocyte adhesion to cultured endothelial cells." J Cell Biol. Jul. 1988;107(1):321–31.

Emsley, J. et al., "Structural basis of collagen recognition by integrin alpha2beta1." Cell. Mar. 31, 2000;101(1):47–56.

Emsley, J. et al., "Crystal structure of the I domain from integrin alpha2beta1." J Biol Chem. Nov. 7, 1997;272(45):28512–7.

Harbury, P.B. et al., "Repacking protein cores with backbone freedom: structure prediction for coiled coils." Proc Natl Acad Sci U S A. Aug. 29, 1995;92(18):8408–12.

Harlan, J.M. et al., "The role of neutrophil membrane glycoprotein GP–150 in neutrophil adherence to endothelium in vitro." Blood. Jul. 1985;66(1):167–78.

Haskard, D. et al., "T lymphocyte adhesion to endothelial cells: mechanisms demonstrated by anti–LFA–1 monoclonal antibodies." J Immunol. Nov. 1, 1986;137(9):2901–6.

Hellinga, H.W. and Richards, F.M. "Construction of new ligand binding sites in proteins of known structure. I.Computer–aided modeling of sites with pre–defined geometry." J Mol Biol. Dec. 5, 1991;222(3):763–85.

Huang, C. and Springer, T.A., "A binding interface on the I domain of lymphocyte function–associated antigen–1 (LFA–1) required for specific interaction with intercellular adhesion molecule 1 (ICAM–1)." J Biol Chem. Aug. 11, 1995;270(32):19008–16.

Humphries, M.J. "Integrin structure." Bichem Soc Trans. 2000;28(4):311–39.

Hurley, J.H. et al., "Design and structural analysis of alternative hydrophobic core packing arrangements in bacteriophage T4 lysozyme." J Mol Biol. Apr. 20, 1992;224(4):1143–59.

Jones, D.T. "De novo protein design using pairwise potentials and a genetic algorithm." Protein Sci. Apr. 1994, 3(4):567–74.

Kaufmann, Y. et al., "Cloning of the murine lymphocyte function–associated molecule–1 alpha–subunit and its expression in COS cells." J Immunol. Jul. 1, 1991;147(1):369–74.

Kishimoto, T.K. et al., "The leukocyte integrins." Adv Immunol. 1989;46:149–82.

Klemba, M. et al., "Novel metal–binding proteins by design."baNat Struct Biol. May 1995;2(5):368–73.

Kono, H. and Doi, J. "Energy minimization method using automata network for sequence and side–chain conformation prediction from given backbone geometry." Proteins. Jul. 1994;19(3):244–55.

Krensky, A.M. et al., "The functional significance, distribution, and structure of LFA–1, LFA–2, and LFA–3: cell surface antigens associated with CTL–target interactions." J Immunol. Aug. 1983;131(2):611–6.

Lanier, L.L. et al., "p150/95, Third member of the LFA–1/CR3 polypeptide family identified by anti–Leu M5 monoclonal antibody." Eur J Immunol. Jul. 1985;15(7):713–8.

Larson, R.S. et al., "Primary structure of the leukocyte function–associated molecule–1 alpha subunit: an integrin with an embedded domain defining a protein superfamily." J Cell Biol. Feb. 1989;108(2):703–12.

Lee, J.O. et al., "Crystal structure of the A domain from the alpha subunit of integrin CR3 (CD11b/CD18)." Cell. Feb. 24, 1995;80(4):631–8.

Lee, J.O. et al., "Two conformations of the integrin A–domain (I–domain): a pathway for activation?" Structure. Dec. 15, 1995;3(12):1333–40.

Li, R. et al., "Two functional states of the CD11b A–domain: correlations with key features of two Mn2+–complexed crystal structures." J Cell Biol. Dec. 14, 1998;143(6):1523–34.

Lo, S.K. et al., "Transient adhesion of neutrophils to endothelium." J Exp Med. May 1, 1989;169(5):1779–93.

Lo, S.K., et al., "Two leukocyte receptors (CD11a/CD18 and CD11b/CD18) mediate transient adhesion to endothelium by binding to different ligands." J Immunol. Nov. 15, 1989;143(10):3325–9.

Loftus, J.C. and Liddington, R.C. "Cell adhesion in vascular biology. New insights into integrin–ligand interaction." J Clin Invest. May 15, 1997;99(10):2302–6.

Malakauskas, S.M. and Mayo, S.L. "Design, structure and stability of a hyperthermophilic protein variant." Nat Struct Biol. Jun. 1998;5(6):470–5.

Michishita, M. et al., "A novel divalent cation–binding site in the A domain of the beta 2 integrin CR3 (CD11b/CD18) is essential for ligand binding." Cell. Mar. 26, 1993;72(6):857–67.

Nautiyal, S. et al., "A designed heterotrimeric coiled coil." Biochemistry. Sep. 19, 1995;34(37):11645–51.

Nolte, M. et al., "Crystal structure of the alpha1 beta1 integrin I–domain: insights into integrin I–domain function." FEBS Lett. Jun. 11, 1999;452(3):379–85.

Oxvig, C. et al., "Conformational changes in tertiary structure near the ligand binding site of an integrin I domain." Proc Natl Acad Sci U S A. Mar. 2, 1999;96(5):2215–20.

Perutz, M.F. "Mechanisms of cooperativity and allosteric regulation in proteins." Q Rev Biophys. May 1989;22(2):139–237.

Pytela, R. "Amino acid sequence of the murine Mac–1 alpha chain reveals homology with the integrin family and an additional domain related to von Willebrand factor." EMBO J. May 1988;7(5):1371–8.

Qu, A. and Leahy, D.J. "Crystal structure of the I–domain from the CD11a/CD18 (LFA–1, alpha L beta 2) integrin." Proc Natl Acad Sci U S A. Oct. 24, 1995;92(22):10277–81.

Qu, A. and Leahy, D.J. "The role of the divalent cation in the structure of the I domain from the CD11a/CD18 integrin." Structure. Aug. 15, 1996;4(8):931–42.

Rich, R.L. et al., "Trench–shaped binding sites promote multiple classes of interactions between collagen and the adherence receptors, alpha(1)beta(1) integrin and *Staphylococcus aureus* cna MSCRAMM." J Biol Chem. Aug. 27, 1999;274(35):24906–13.

Smith, C.W. et al., "Cooperative interactions of LFA–1 and Mac–1 with intercellular adhesion molecule–1 in facilitating adherence and transendothelial migration of human neutrophils in vitro." J Clin Invest. Jun. 1989;83(6):2008–17.

Smith, C.W. et al., "Recognition of an endothelial determinant for CD 18–dependent human neutrophil adherence and transendothelial migration." J Clin Invest. Nov. 1988;82(5):1746–56.

Smyth, S.S. et al., "Regulation of vascular integrins." Blood. Jun. 1, 1993;81(11):2827–43.

Springer, T.A. and Anderson, D.C. "The importance of the Mac–1, LFA–1 glycoprotein family in monocyte and granulocyte adherence, chemotaxis, and migration into inflammatory sites: insights from an experiment of nature." Ciba Found Symp. 1986;118:102–26.

Springer, T.A. "Folding of the N–terminal, ligand–binding region of integrin alpha–subunits into a beta–propeller domain." Proc Natl Acad Sci U S A. Jan. 7, 1997;94(1):65–72.

Springer, T.A. "Adhesion receptors of the immune system." Nature. Aug. 2, 1990;346(6283):425–34.

Todd. R.F. 3rd et al., "Subcellular localization of the large subunit of Mo1 (Mo1 alpha; formerly gp 110), a surface glycoprotein associated with neutrophil adhesion." J Clin Invest. Oct. 1984;74(4):1280–90.

Yancey, K.B. et al., "Human C5a modulates monocyte Fc and C3 receptor expression." J Immunol. Jul. 1985;135(1):465–70.

Zhang, L. and Plow, E.F.. "Amino acid sequences within the alpha subunit of integrin alpha M beta 2 (Mac–1) critical for specific recognition of C3bi." Biochemistry. Jun. 22, 1999;38(25):8064–71.

Huth, JR, et al, NMR and mutagenesis evidence for an I domain allosteric site that regulates lymphocyte function–associated antigen 1 ligand binding. Proc Natl Acad Sci U S A. May 9, 2000;97(10):5231–6.

Lu, C, et al., "Association of the membrane proximal regions of the alpha and beta subunit cytoplasmic domains constrains an integrin in the inactive state." J Biol Chem. May 4, 2001;276(18):14642–8.

Shimaoka M, et al., "Conformational regulation of integrin structure and function." Annu Rev Biophys Biomol Struct. 2002;31:485–516.

Shimaoka M, et al., "Computational design of an integrin I domain stabilized in the open high affinity conformation." Nat Struct Biol. Aug. 2000;7(8):674–8.

Xiong JP, et al., "An isoleucine–based allosteric switch controls affinity and shape shifting in integrin CD11b A–domain." J Biol Chem. Dec. 8, 2000;275(49):38762–7.

* cited by examiner

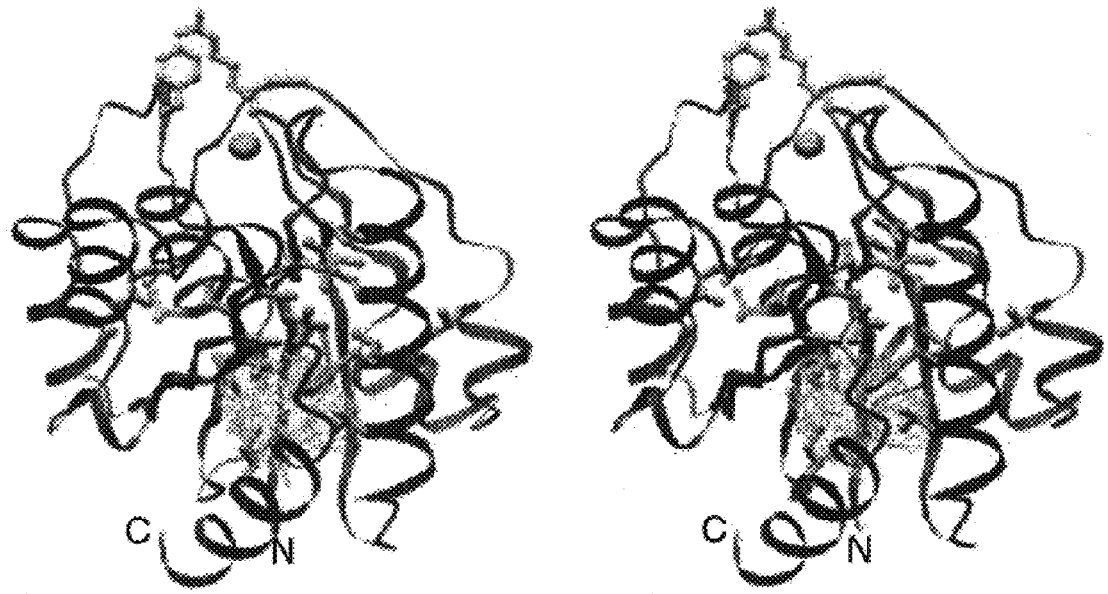
FIG._1A
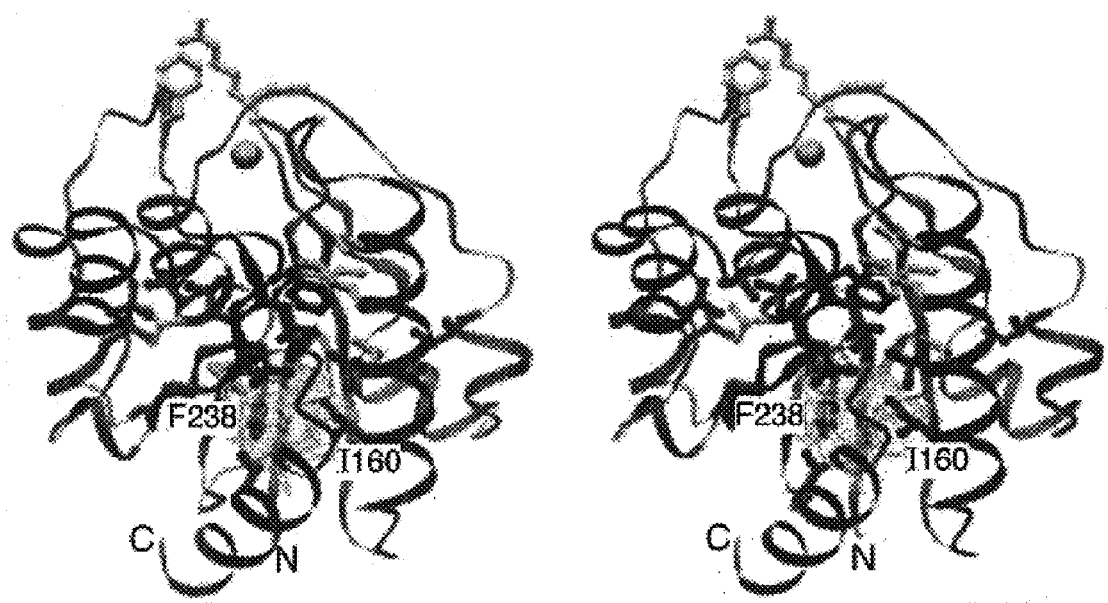
FIG._1B

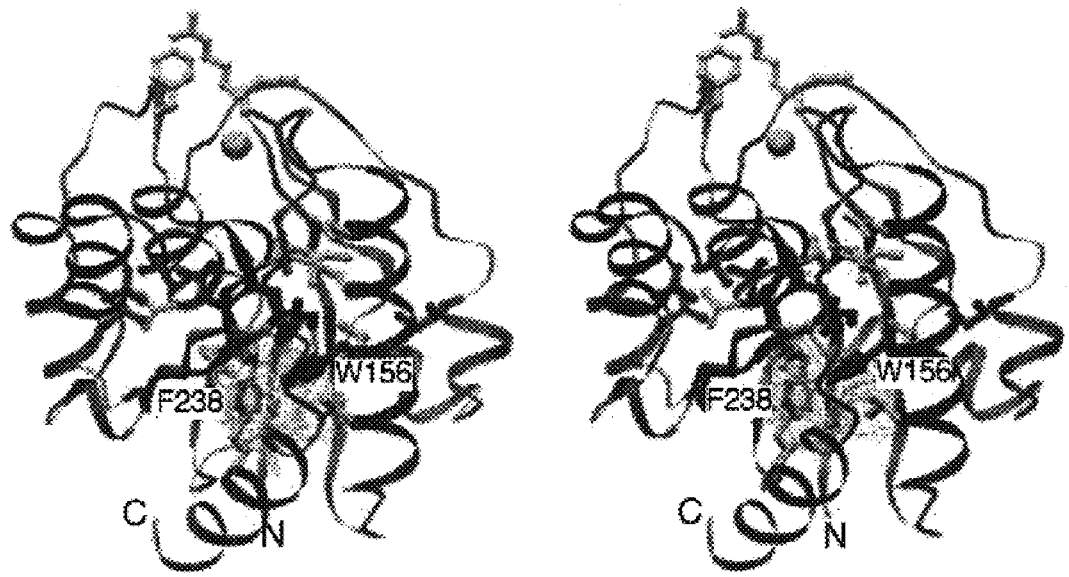
FIG._1C
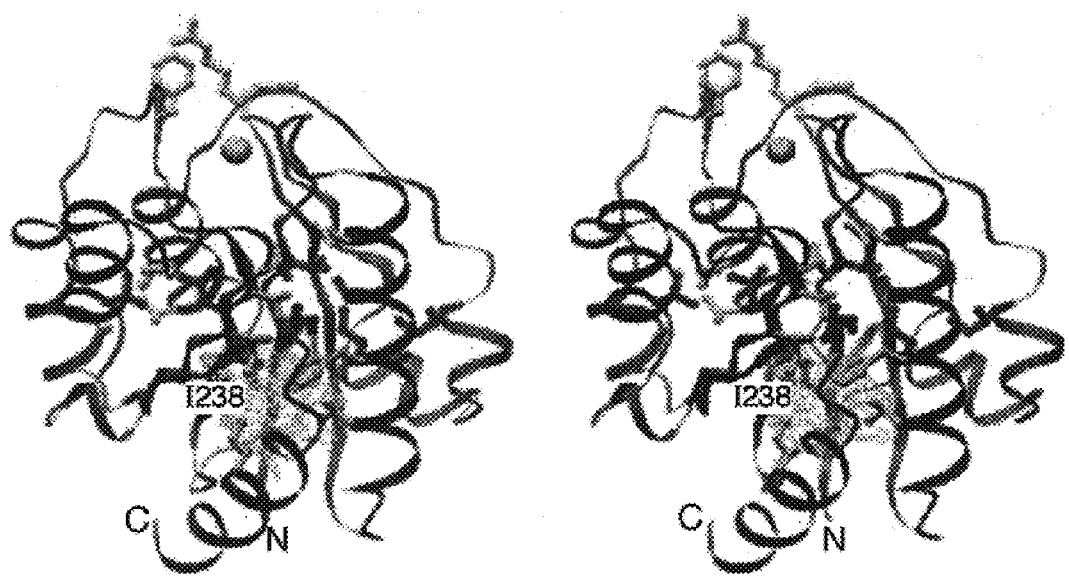
FIG._1D

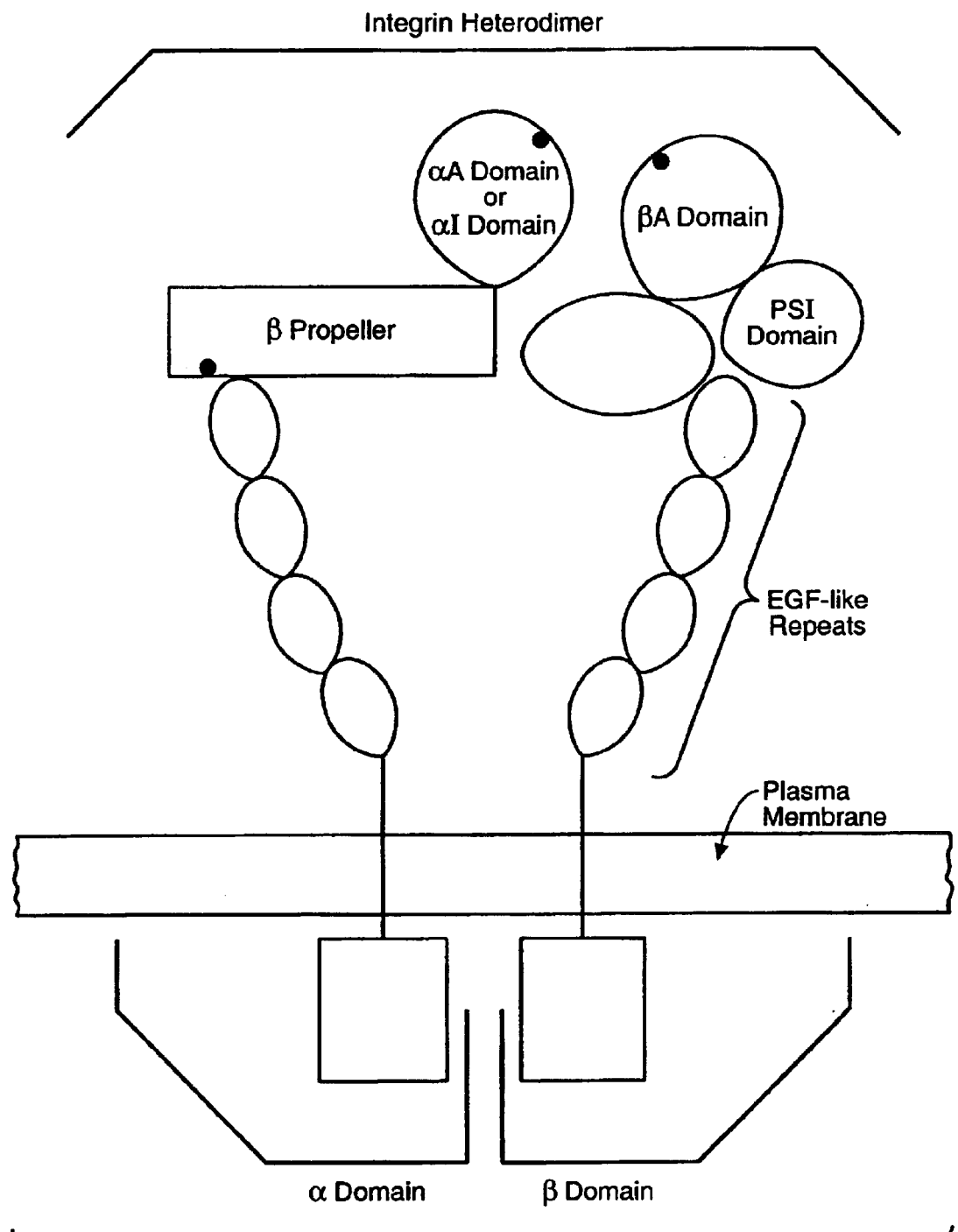
FIG._1E

```
MALRVLLLTALTLCHGFNLDTENAMTFQENARGFGQSVVQLQGSRVVVGAP
QEIVAANQRGSLYQCDYSTGSCEPIRLQVPVEAVNMSLGLSLAATTSPPQL
LACGPTVHQTCSENTYVKGLCFLFGSNLRQQPQKFPEALRGCPQEDSDIAF
LIDGSGSIIPHDFRRMKEFVSTVMEQLKKSKTLFSLMQYSEEFRIHFTFKE
FQNNPNPRSLVKPITQLLGRTHTATGIRKVVRELFNITNGARKNAFKILVV
ITDGEKFGDPLGYEDVIPEADREGVIRYVIGVGDAFRSEKSRQELNTIASK
PPRDHVFQVNNFEALKTIQNQLREKIFAIEGTQTGSSSSFEHEMSQEGFSA
AITSNGPLLSTVGSYDWAGGVFLYTSKEKSTFINMTRVDSDMNDAYLGYAA
AIILRNRVQSLVLGAPRYQHIGLVAMFRQNTGMWESNANVKGTQIGAYFGA
SLCSVDVDSNGSTDLVLIGAPHYYEQTRGGQVSVCPLPRGQRARWQCDAVL
YGEQGQPWGRFGAALTVLGDVNGDKLTDVAIGAPGEEDNRGAVYLFHGTSG
SGISPSHSQRIAGSKLSPRLQYFGQSLSGGQDLTMDGLVDLTVGAQGHVLL
LRSQPVLRVKAIMEFNPREVARNVFECNDQVVKGKEAGEVRVCLHVQKSTR
DRLREGQIQSVVTYDLALDSGRPHSRAVFNETKNSTRRQTQVLGLTQTCET
LKLQLPNCIEDPVSPIVLRLNFSLVGTPLSAFGNLRPVLAEDAQRLFTALF
PFEKNCGNDNICQDDLSITFSFMSLDCLVVGGPREFNVTVTVRNDGEDSYR
TQVTFFFPLDLSYRKVSTLQNQRSQRSWRLACESASSTEVSGALKSTSCSI
NHPIFPENSEVTFNITFDVDSKASLGNKLLLKANVTSENNMPRTNKTEFQL
ELPVKYAVYMVVTSHGVSTKYLNFTASENTSRVMQHQYQVSNLGQRSLPIS
LVFLVPVRLNQTVIWDRPQVTFSENLSSTCHTKERLPSHSDFLAELRKAPV
VNCSIAVCQRIQCDIPFFGIQEEFNATLKGNLSFDWYIKTSHNHLLIVSTA
EILFNDSVFTLLPGQGAFVRSQTETKVEPFEVPNPLPLIVGSSVGGLLLLA
LITAALYKLGFFKRQYKDMMSEGGPPGAEPQ
```

FIG._1F

```
gaattccgtg gttcctcagt ggtgcctgca accccctggtt cacctccttc caggttctgg
ctccttccag ccatggctct cagagtcctt ctgttaacag ccttgacctt atgtcatggg
ttcaacttgg acactgaaaa cgcaatgacc ttccaagaga acgcaagggg cttcgggcag
agcgtggtcc agcttcaggg atccagggtg gtggttggag ccccccagga gatagtggct
gccaaccaaa ggggcagcct ctaccagtgc gactacagca caggctcatg cgagcccatc
cgcctgcagg tcccgtgga ggccgtgaac atgtccctgg gcctgtccct ggcagccacc
accagccccc ctcagctgct ggcctgtggt cccaccgtgc accagacttg cagtgagaac
acgtatgtga aagggctctg cttcctgttt ggatccaacc tacggcagca gccccagaag
ttcccagagg ccctccgagg gtgtcctcaa gaggatagtg acattgcctt cttgattgat
ggctctggta gcatcatccc acatgacttt cggcggatga aggagtttgt ctcaactgtg
atggagcaat taaaaaagtc caaaaccttg ttctctttga tgcagtactc tgaagaattc
cggattcact ttaccttcaa agagttccag aacaacccta acccaagatc actggtgaag
ccaataacgc agctgcttgg gcggacacac acggccacgg gcatccgcaa agtggtacga
gagctgttta acatcaccaa cggagcccga aagaatgcct ttaagatcct agttgtcatc
acggatggag aaaagtttgg cgatcccttg ggatatgagg atgtcatccc tgaggcagac
agagagggag tcattcgcta cgtcattggg gtgggagatg ccttccgcag tgagaaatcc
cgccaagagc ttaataccat cgcatccaag ccgcctcgtg atcacgtgtt ccaggtgaat
aactttgagg ctctgaagac cattcagaac cagcttcggg agaagatctt tgcgatcgag
ggtactcaga caggaagtag cagctccttt gagcatgaga tgtctcagga aggcttcagc
gctgccatca cctctaatgg ccccttgctg agcactgtgg ggagctatga ctgggctggt
ggagtctttc tatatacatc aaaggagaaa agcaccttca tcaacatgac cagagtggat
tcagacatga atgatgctta cttgggttat gctgccgcca tcatcttacg gaaccgggtg
caaagcctgg ttctggggc acctcgatat cagcacatcg gcctggtagc gatgttcagg
cagaacactg gcatgtggga gtccaacgct aatgtcaagg gcacccagat cggcgcctac
ttcggggcct ccctctgctc cgtggacgtg gacagcaacg gcagcaccga cctggtcctc
atcggggccc cccattacta cgagcagacc cgaggggggcc aggtgtccgt gtgcccctttg
cccaggggc agagggctcg gtggcagtgt gatgctgttc tctacgggga gcagggccaa
ccctggggcc gctttgggc agccctaaca gtgctggggg acgtaaatgg ggacaagctg
acggacgtgg ccattggggc cccaggagag gaggacaacc ggggtgctgt ttacctgttt
cacggaacct caggatctgg catcagcccc tcccatagcc agcggatagc aggctccaag
ctctctccca ggctccagta ttttggtcag tcactgagtg ggggccagga cctcacaatg
gatggactgg tagacctgac tgtaggagcc caggggcacg tgctgctgct caggtcccag
ccagtactga gagtcaaggc aatcatggag ttcaatccca gggaagtggc aaggaatgta
tttgagtgta atgatcaggt ggtgaaaggc aaggaagccg gagaggtcag agtctgcctc
catgtccaga agagcacacg ggatcggcta agagaaggac agatccagag tgttgtgact
tatgacctgg ctctggactc cggccgccca cattcccgcg ccgtcttcaa tgagacaaag
aacagcacac gcagacagac acaggtcttg gggctgaccc agacttgtga gaccctgaaa
ctacagttgc cgaattgcat cgaggaccca gtgagcccca ttgtgctgcg cctgaacttc
tctctggtgg aacgccatt gtctgctttc gggaacctcc ggccagtgct ggcggaggat
gctcagagac tcttcacagc cttgtttccc tttgagaaga attgtggcaa tgacaacatc
tgccaggatg acctcagcat caccttcagt ttcatgagcc tggactgcct cgtggtgggt
gggccccggg agttcaacgt gacagtgact gtgagaaatg atggtgagga ctcctacagg
acacaggtca ccttcttctt cccgcttgac ctgtcctacc ggaaggtgtc cacactccag
aaccagcgct cacagcgatc ctggcgcctg gcctgtgagt ctgcctcctc caccgaagtg
tctggggcct tgaagagcac cagctgcagc ataaaccacc ccatcttccc ggaaaactca
gaggtcacct ttaatatcac gtttgatgta gactctaagg cttcccttgg aaacaaactg
ctcctcaagg ccaatgtgac cagtgagaac aacatgccca gaaccaacaa aaccgaattc
caactggagc tgccggtgaa atatgctgtc tacatggtgg tcaccagcca tgggggtctcc
actaaatatc tcaacttcac ggcctcagag aataccagtc gggtcatgca gcatcaatat
caggtcagca acctggggca gaggagcctc cccatcagcc tggtgttctt ggtgcccgtc
cggctgaacc agactgtcat atgggaccgc ccccaggtca ccttctccga gaacctctcg
```

FIG._1G-1

```
agtacgtgcc acaccaagga gcgcttgccc tctcactccg actttctggc tgagcttcgg
aaggcccccg tggtgaactg ctccatcgct gtctgccaga gaatccagtg tgacatcccg
ttctttggca tccaggaaga attcaatgct accctcaaag gcaacctctc gtttgactgg
tacatcaaga cctcgcataa ccacctcctg atcgtgagca cagctgagat cttgtttaac
gattccgtgt tcaccctgct gccgggacag ggggcgtttg tgaggtccca gacggagacc
aaagtggagc cgttcgaggt ccccaacccc ctgccgctca tcgtgggcag ctctgtcggg
ggactgctgc tcctggccct catcaccgcc gcgctgtaca agctcggctt cttcaagcgg
caatacaagg acatgatgag tgaagggggt cccccggggg ccgaacccca gtagcggctc
cttcccgaca gagctgcctc tggtggcca gcaggactct gcccagacca cacgtagccc
ccaggctgct ggacacgtcg gacagcgaag tatccccgac aggacgggct tgggcttcca
tttgtgtgtg tgcaagtgtg tatgtgcgtg tgtgcgagtg tgtgcaagtg tctgtgtgca
agtgtgtgca cgtgtgcgtg tgcgtgcatg tgcactcgca cgcccatgtg tgagtgtgtg
caagtatgtg agtgtgtcca gtgtgtgtgc gtgtgtccat gtgtgtgcag tgtgtgcatg
tgtgcgagtg tgtgcatgtg tgtgctcagg ggctgtggct cacgtgtgtg actcagagtg
tctctggcgt gtgggtaggt gacggcagcg tagcctctcc ggcagaaggg aactgcctgg
gctcccttgt gcgtgggtaa gccgctgctg ggttttcctc cgggagaggg gacggtcaat
cctgtgggtg aagagagagg gaaacacagc agcatctctc cactgaaaga agtgggactt
cccgtcgcct gcgagcctgc ggcctgctgg agcctgcgca gcttggatgg atactccatg
agaaaagccg tgggtggaac caggagcctc ctccacacca gcgctgatgc ccaataaaga
tgcccactga ggaatcatga agcttccttt ctggattcat ttattatttc aatgtgactt
taattttttg gatggataag cctgtctatg gtacaaaaat cacaaggcat tcaagtgtac
agtgaaaagt ctcccttttcc agatattcaa gtcacctcct taaaggtagt caagattgtg
ttttgaggtt tccttcagac agattccagg cgatgtgcaa gtgtatgcac gtgtgcacac
accacacaca tacacacaca caagcttttt tacacaaatg gtagcatact ttatattggt
ctgtatcttg ctttttttca ccaatatttc tcagacatcg gttcatatta agacataaat
tacttttttca ttcttttata ccgctgcata gtattccatt gtgtgagtgt accataatgt
atttaaccag tcttcttttg atatactatt ttcatctctt gttattgcat ctgctgagtt
aataaatcaa atatatgtca aaaaaaaaa aaaaaaaaa aaaaaaaaa aaaaaaaaa
```

FIG._1G-2

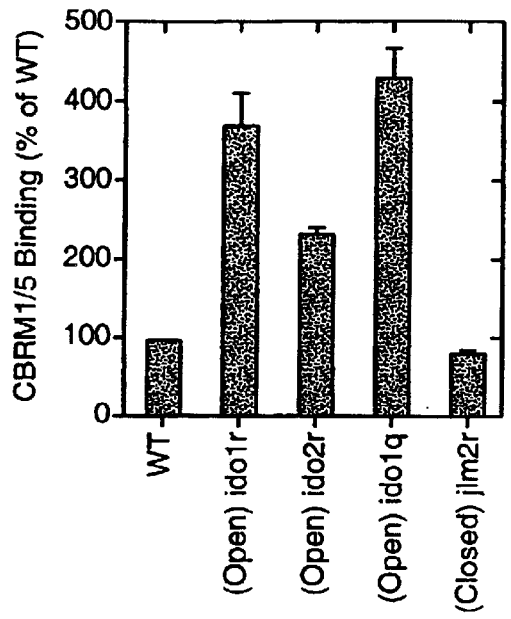
FIG._2A
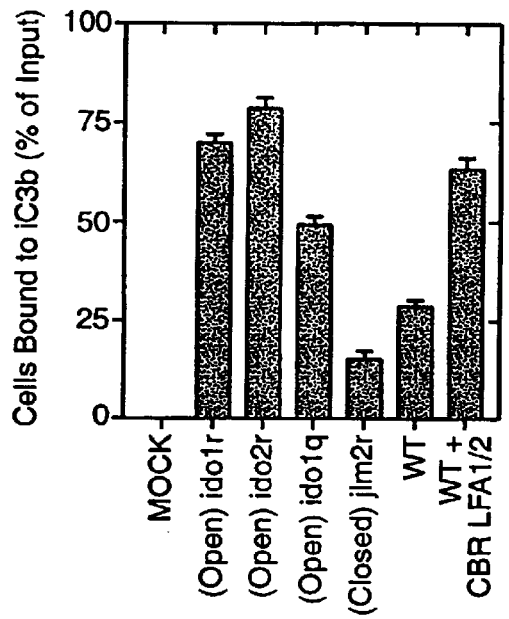
FIG._2B
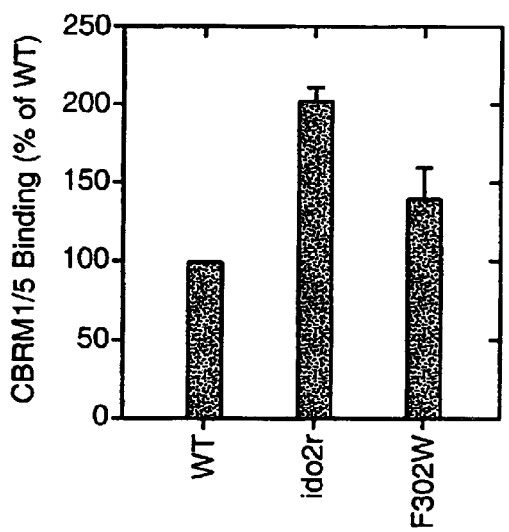
FIG._2C
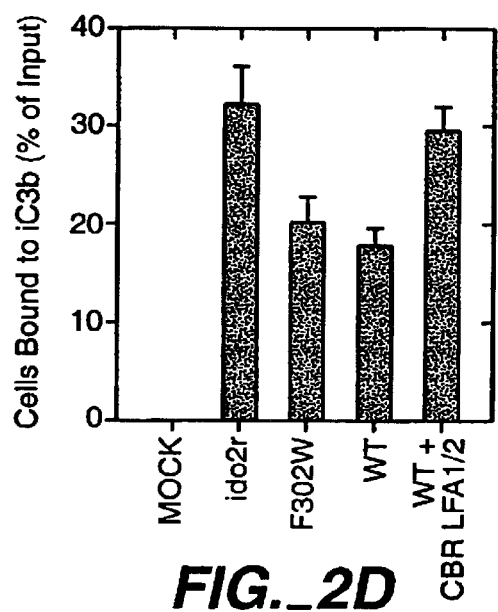
FIG._2D

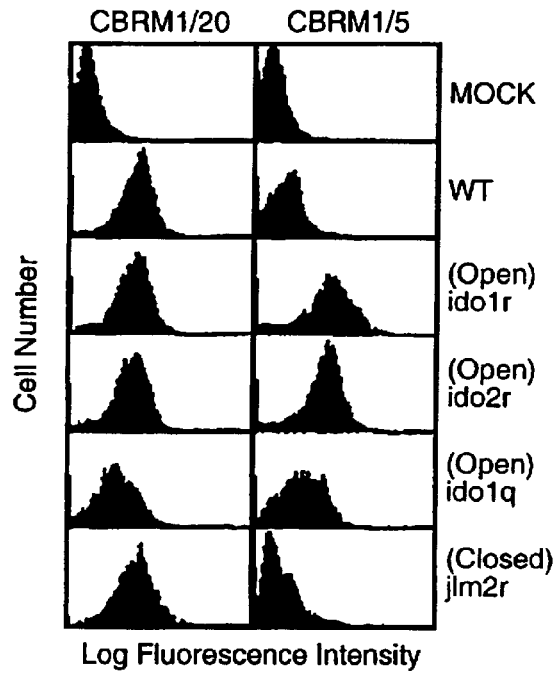
FIG._3A
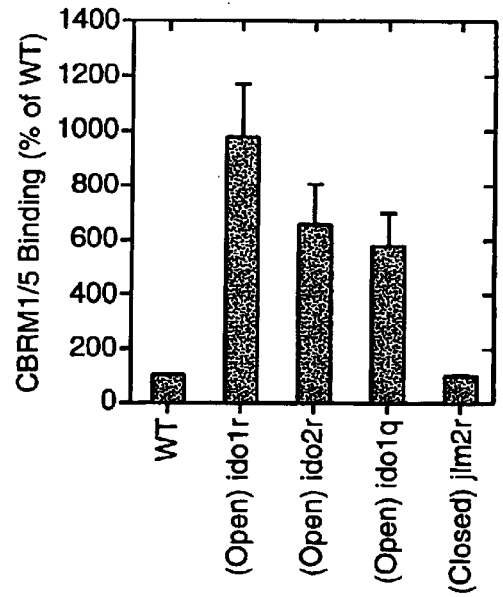
FIG._3B
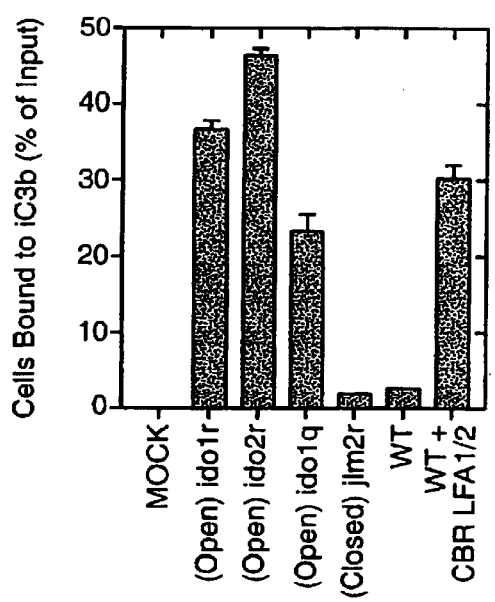
FIG._3C
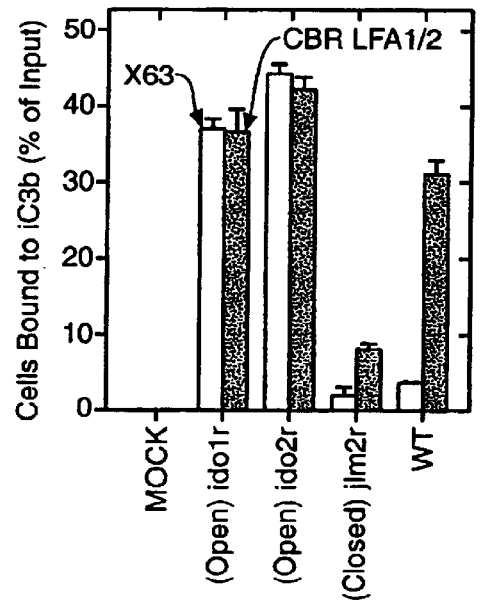
FIG._3D

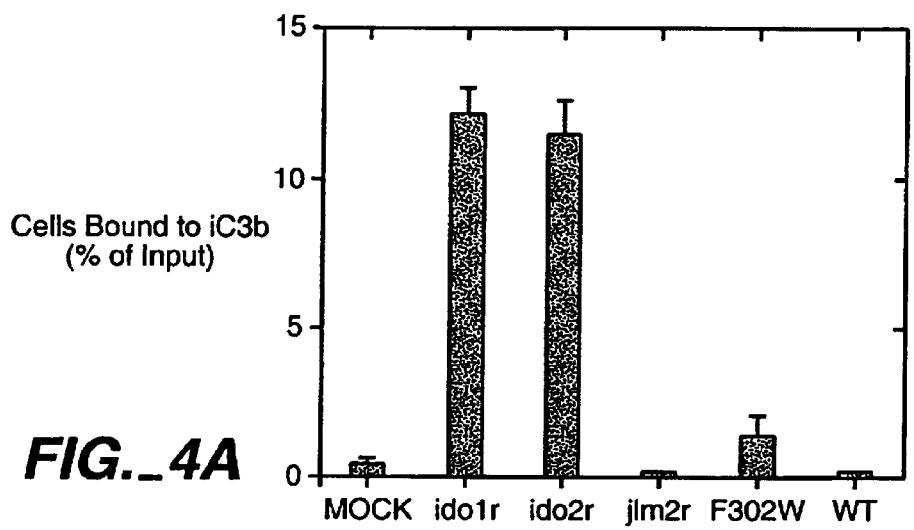
FIG._4A
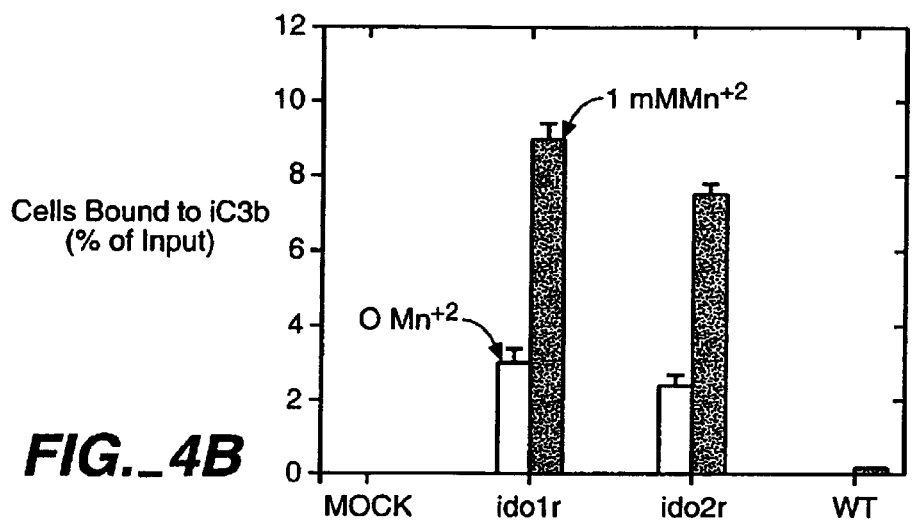
FIG._4B
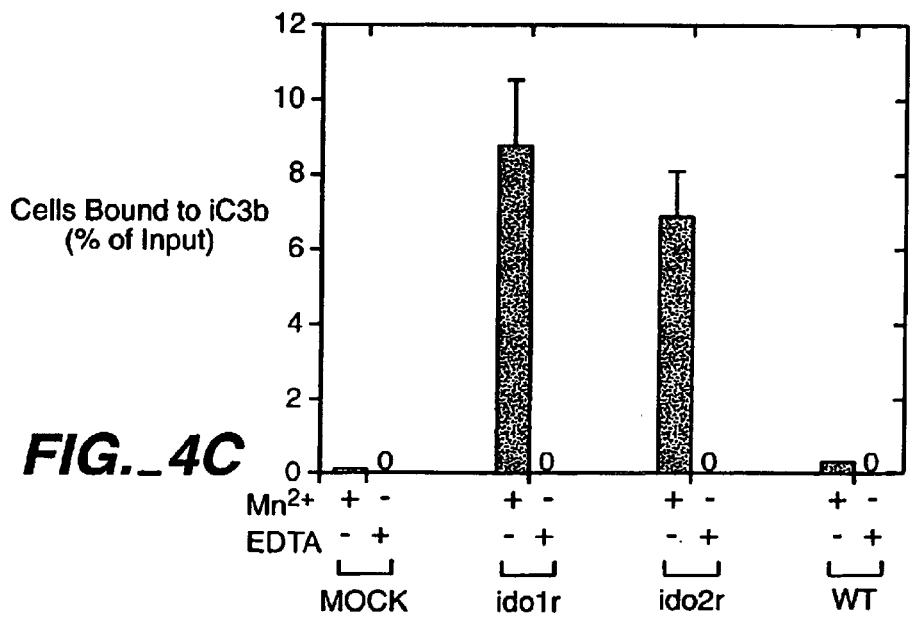
FIG._4C

FIG._5
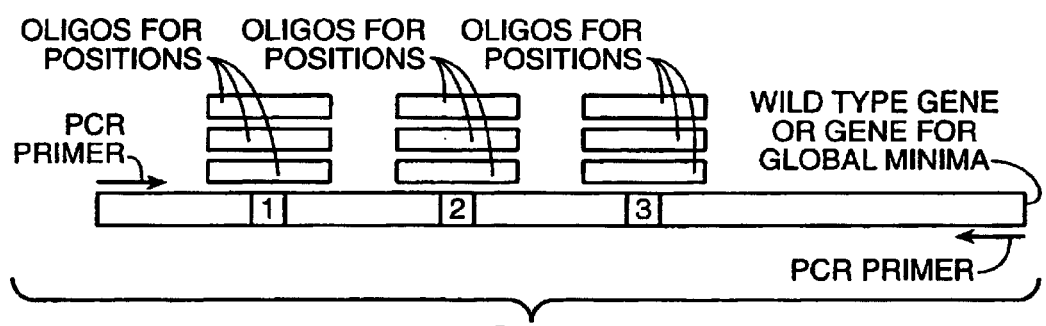
FIG._6

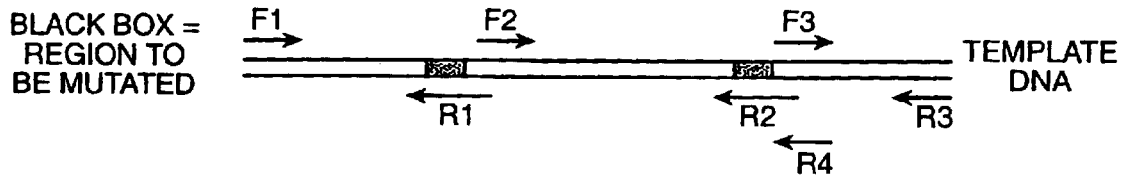
BLACK BOX = REGION TO BE MUTATED
TEMPLATE DNA
STEP 1: SET UP 3 PCR REACTIONS:
PRODUCTS:
TUBE 1: 
TUBE 2: 
TUBE 3: 
STEP 2: SET UP PCR REACTION WITH PRODUCTS OF TUBE 1 + PRODUCTS TUBE 2 + F1 + R4.
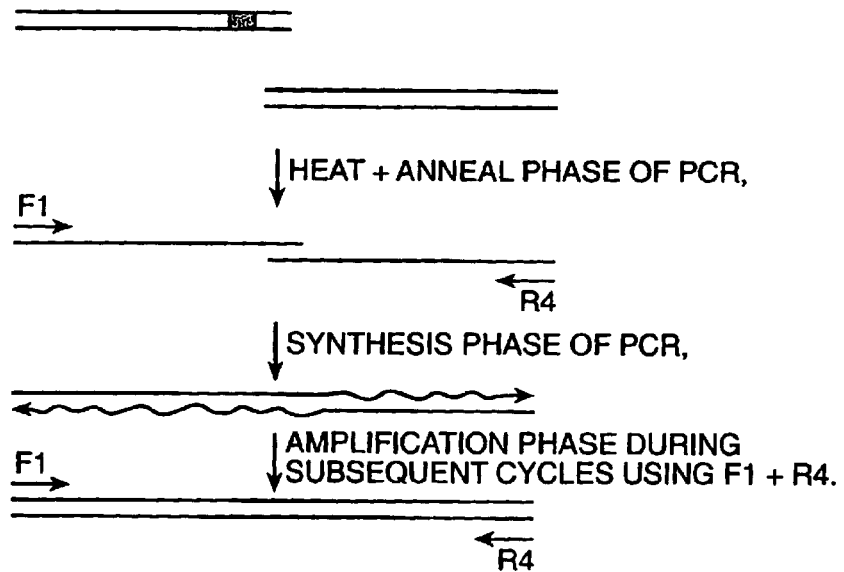
STEP 3: REPEAT STEP 2 USING PRODUCT FROM STEP 2 + PRODUCT FROM STEP 1, TUBE 3 + PRIMERS F1 + R3.
*FIG._7*

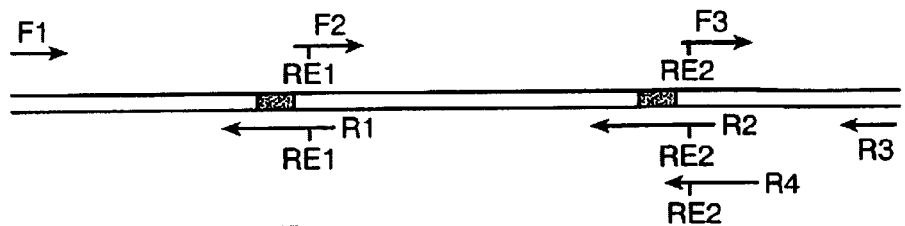

STEP 1: SET UP 3 PCR REACTIONS:

TUBE 1: 

TUBE 2: 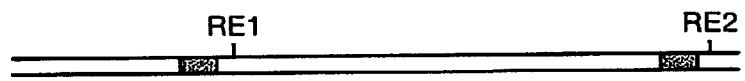

TUBE 3: 

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

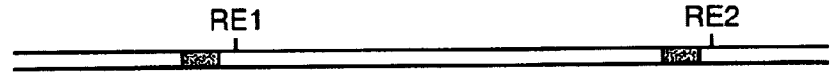

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 3.

STEP 7: AMPLIFY PRODUCT FROM STEP 6 WITH F1 + R3.

FIG._8

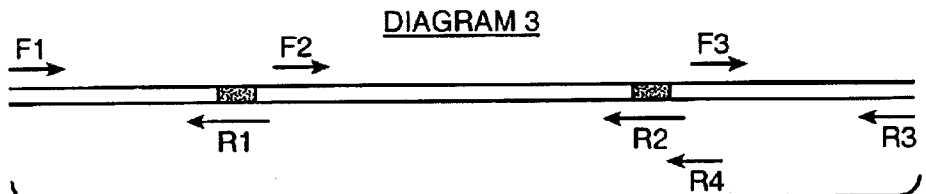

SEQUENCE LISTING

```
<160> NUMBER OF SEQ ID NOS: 13

<210> SEQ ID NO 1
<211> LENGTH: 1153
<212> TYPE: PRT
<213> ORGANISM: Homo sapiens
<220> FEATURE:
<221> NAME/KEY: mat_peptide
<222> LOCATION: (17)..()
<223> OTHER INFORMATION:

<400> SEQUENCE: 1

Met Ala Leu Arg Val Leu Leu Leu Thr Ala Leu Thr Leu Cys His Gly
    -15                 -10                  -5                  -1

Phe Asn Leu Asp Thr Glu Asn Ala Met Thr Phe Gln Glu Asn Ala Arg
1               5                  10                  15

Gly Phe Gly Gln Ser Val Val Gln Leu Gln Gly Ser Arg Val Val Val
            20                  25                  30

Gly Ala Pro Gln Glu Ile Val Ala Ala Asn Gln Arg Gly Ser Leu Tyr
        35                  40                  45

Gln Cys Asp Tyr Ser Thr Gly Ser Cys Glu Pro Ile Arg Leu Gln Val
    50                  55                  60

Pro Val Glu Ala Val Asn Met Ser Leu Gly Leu Ser Leu Ala Ala Thr
65                  70                  75                  80
```

-continued

```
Thr Ser Pro Pro Gln Leu Leu Ala Cys Gly Pro Thr Val His Gln Thr
                85                  90                  95
Cys Ser Glu Asn Thr Tyr Val Lys Gly Leu Cys Phe Leu Phe Gly Ser
            100                 105                 110
Asn Leu Arg Gln Gln Pro Gln Lys Phe Pro Glu Ala Leu Arg Gly Cys
        115                 120                 125
Pro Gln Glu Asp Ser Asp Ile Ala Phe Leu Ile Asp Gly Ser Gly Ser
    130                 135                 140
Ile Ile Pro His Asp Phe Arg Arg Met Lys Glu Phe Val Ser Thr Val
145                 150                 155                 160
Met Glu Gln Leu Lys Lys Ser Lys Thr Leu Phe Ser Leu Met Gln Tyr
                165                 170                 175
Ser Glu Glu Phe Arg Ile His Phe Thr Phe Lys Glu Phe Gln Asn Asn
            180                 185                 190
Pro Asn Pro Arg Ser Leu Val Lys Pro Ile Thr Gln Leu Leu Gly Arg
        195                 200                 205
Thr His Thr Ala Thr Gly Ile Arg Lys Val Val Arg Glu Leu Phe Asn
    210                 215                 220
Ile Thr Asn Gly Ala Arg Lys Asn Ala Phe Lys Ile Leu Val Val Ile
225                 230                 235                 240
Thr Asp Gly Glu Lys Phe Gly Asp Pro Leu Gly Tyr Glu Asp Val Ile
                245                 250                 255
Pro Glu Ala Asp Arg Glu Gly Val Ile Arg Tyr Val Ile Gly Val Gly
            260                 265                 270
Asp Ala Phe Arg Ser Glu Lys Ser Arg Gln Glu Leu Asn Thr Ile Ala
        275                 280                 285
Ser Lys Pro Pro Arg Asp His Val Phe Gln Val Asn Asn Phe Glu Ala
    290                 295                 300
Leu Lys Thr Ile Gln Asn Gln Leu Arg Glu Lys Ile Phe Ala Ile Glu
305                 310                 315                 320
Gly Thr Gln Thr Gly Ser Ser Ser Phe Glu His Glu Met Ser Gln
                325                 330                 335
Glu Gly Phe Ser Ala Ala Ile Thr Ser Asn Gly Pro Leu Leu Ser Thr
            340                 345                 350
Val Gly Ser Tyr Asp Trp Ala Gly Gly Val Phe Leu Tyr Thr Ser Lys
        355                 360                 365
Glu Lys Ser Thr Phe Ile Asn Met Thr Arg Val Asp Ser Asp Met Asn
    370                 375                 380
Asp Ala Tyr Leu Gly Tyr Ala Ala Ala Ile Ile Leu Arg Asn Arg Val
385                 390                 395                 400
Gln Ser Leu Val Leu Gly Ala Pro Arg Tyr Gln His Ile Gly Leu Val
                405                 410                 415
Ala Met Phe Arg Gln Asn Thr Gly Met Trp Glu Ser Asn Ala Asn Val
            420                 425                 430
Lys Gly Thr Gln Ile Gly Ala Tyr Phe Gly Ala Ser Leu Cys Ser Val
        435                 440                 445
Asp Val Asp Ser Asn Gly Ser Thr Asp Leu Val Leu Ile Gly Ala Pro
    450                 455                 460
His Tyr Tyr Glu Gln Thr Arg Gly Gly Gln Val Ser Val Cys Pro Leu
465                 470                 475                 480
Pro Arg Gly Gln Arg Ala Arg Trp Gln Cys Asp Ala Val Leu Tyr Gly
                485                 490                 495
```

```
Glu Gln Gly Gln Pro Trp Gly Arg Phe Gly Ala Ala Leu Thr Val Leu
            500                 505                 510
Gly Asp Val Asn Gly Asp Lys Leu Thr Asp Val Ala Ile Gly Ala Pro
            515                 520                 525
Gly Glu Glu Asp Asn Arg Gly Ala Val Tyr Leu Phe His Gly Thr Ser
            530                 535                 540
Gly Ser Gly Ile Ser Pro Ser His Ser Gln Arg Ile Ala Gly Ser Lys
545                 550                 555                 560
Leu Ser Pro Arg Leu Gln Tyr Phe Gly Gln Ser Leu Ser Gly Gly Gln
            565                 570                 575
Asp Leu Thr Met Asp Gly Leu Val Asp Leu Thr Val Gly Ala Gln Gly
            580                 585                 590
His Val Leu Leu Leu Arg Ser Gln Pro Val Leu Arg Val Lys Ala Ile
            595                 600                 605
Met Glu Phe Asn Pro Arg Glu Val Ala Arg Asn Val Phe Glu Cys Asn
            610                 615                 620
Asp Gln Val Val Lys Gly Lys Glu Ala Gly Glu Val Arg Val Cys Leu
625                 630                 635                 640
His Val Gln Lys Ser Thr Arg Asp Arg Leu Arg Glu Gly Gln Ile Gln
            645                 650                 655
Ser Val Val Thr Tyr Asp Leu Ala Leu Asp Ser Gly Arg Pro His Ser
            660                 665                 670
Arg Ala Val Phe Asn Glu Thr Lys Asn Ser Thr Arg Arg Gln Thr Gln
            675                 680                 685
Val Leu Gly Leu Thr Gln Thr Cys Glu Thr Leu Lys Leu Gln Leu Pro
            690                 695                 700
Asn Cys Ile Glu Asp Pro Val Ser Pro Ile Val Leu Arg Leu Asn Phe
705                 710                 715                 720
Ser Leu Val Gly Thr Pro Leu Ser Ala Phe Gly Asn Leu Arg Pro Val
            725                 730                 735
Leu Ala Glu Asp Ala Gln Arg Leu Phe Thr Ala Leu Phe Pro Phe Glu
            740                 745                 750
Lys Asn Cys Gly Asn Asp Asn Ile Cys Gln Asp Asp Leu Ser Ile Thr
            755                 760                 765
Phe Ser Phe Met Ser Leu Asp Cys Leu Val Val Gly Gly Pro Arg Glu
            770                 775                 780
Phe Asn Val Thr Val Thr Val Arg Asn Asp Gly Glu Asp Ser Tyr Arg
785                 790                 795                 800
Thr Gln Val Thr Phe Phe Pro Leu Asp Leu Ser Tyr Arg Lys Val
            805                 810                 815
Ser Thr Leu Gln Asn Gln Arg Ser Gln Arg Ser Trp Arg Leu Ala Cys
            820                 825                 830
Glu Ser Ala Ser Ser Thr Glu Val Ser Gly Ala Leu Lys Ser Thr Ser
            835                 840                 845
Cys Ser Ile Asn His Pro Ile Phe Pro Glu Asn Ser Glu Val Thr Phe
            850                 855                 860
Asn Ile Thr Phe Asp Val Asp Ser Lys Ala Ser Leu Gly Asn Lys Leu
865                 870                 875                 880
Leu Leu Lys Ala Asn Val Thr Ser Glu Asn Asn Met Pro Arg Thr Asn
            885                 890                 895
Lys Thr Glu Phe Gln Leu Glu Leu Pro Val Lys Tyr Ala Val Tyr Met
            900                 905                 910
Val Val Thr Ser His Gly Val Ser Thr Lys Tyr Leu Asn Phe Thr Ala
```

```
                915                 920                 925
Ser Glu Asn Thr Ser Arg Val Met Gln His Gln Tyr Gln Val Ser Asn
            930                 935                 940

Leu Gly Gln Arg Ser Leu Pro Ile Ser Leu Val Phe Leu Val Pro Val
945                 950                 955                 960

Arg Leu Asn Gln Thr Val Ile Trp Asp Arg Pro Gln Val Thr Phe Ser
                965                 970                 975

Glu Asn Leu Ser Ser Thr Cys His Thr Lys Glu Arg Leu Pro Ser His
            980                 985                 990

Ser Asp Phe Leu Ala Glu Leu Arg  Lys Ala Pro Val  Asn Cys Ser
            995                 1000                1005

Ile Ala  Val Cys Gln Arg Ile  Gln Cys Asp Ile Pro  Phe Phe Gly
    1010                1015                1020

Ile Gln  Glu Glu Phe Asn Ala  Thr Leu Lys Gly Asn  Leu Ser Phe
    1025                1030                1035

Asp Trp  Tyr Ile Lys Thr Ser  His Asn His Leu Leu  Ile Val Ser
    1040                1045                1050

Thr Ala  Glu Ile Leu Phe Asn  Asp Ser Val Phe Thr  Leu Leu Pro
    1055                1060                1065

Gly Gln  Gly Ala Phe Val Arg  Ser Gln Thr Glu Thr  Lys Val Glu
    1070                1075                1080

Pro Phe  Glu Val Pro Asn Pro  Leu Pro Leu Ile Val  Gly Ser Ser
    1085                1090                1095

Val Gly  Gly Leu Leu Leu Leu  Ala Leu Ile Thr Ala  Ala Leu Tyr
    1100                1105                1110

Lys Leu  Gly Phe Phe Lys Arg  Gln Tyr Lys Asp Met  Met Ser Glu
    1115                1120                1125

Gly Gly  Pro Pro Gly Ala Glu  Pro Gln
    1130                1135

<210> SEQ ID NO 2
<211> LENGTH: 4740
<212> TYPE: DNA
<213> ORGANISM: Homo sapiens

<400> SEQUENCE: 2
gaattccgtg gttcctcagt ggtgcctgca accctggtt cacctccttc caggttctgg    60
ctccttccag ccatggctct cagagtcctt ctgttaacag ccttgacctt atgtcatggg   120
ttcaacttgg acactgaaaa cgcaatgacc ttccaagaga cgcaaggggg cttcgggcag   180
agcgtggtcc agcttcaggg atccaggggtg gtggttggag ccccccagga gatagtggct   240
gccaaccaaa ggggcagcct ctaccagtgc gactacagca caggctcatg cgagcccatc   300
cgcctgcagg tccccgtgga ggccgtgaac atgtccctgg gcctgtccct ggcagccacc   360
accagccccc ctcagctgct ggcctgtggt cccaccgtgc accagacttg cagtgagaac   420
acgtatgtga agggctctg cttcctgttt ggatccaacc tacggcagca gccccagaag   480
ttcccagagg ccctccgagg gtgtcctcaa gaggatagtg acattgcctt cttgattgat   540
ggctctggta gcatcatccc acatgacttt cggcggatga aggagtttgt ctcaactgtg   600
atggagcaat aaaaaagtc caaaaccttg ttctctttga tgcagtactc tgaagaattc   660
cggattcact ttaccttcaa agagttccag aacaacccta acccaagatc actggtgaag   720
ccaataacgc agctgcttgg gcggacacac acgccacgg gcatccgcaa agtggtacga   780 gagctgtttta acatcaccaa cggagcccga aagaatgcct taagatcct agttgtcatc   840
```

-continued

| | |
|---|---|
| acggatggag aaaagtttgg cgatcccttg ggatatgagg atgtcatccc tgaggcagac | 900 |
| agagagggag tcattcgcta cgtcattggg gtgggagatg ccttccgcag tgagaaatcc | 960 |
| cgccaagagc ttaataccat cgcatccaag ccgcctcgtg atcacgtgtt ccaggtgaat | 1020 |
| aactttgagg ctctgaagac cattcagaac cagcttcggg agaagatctt tgcgatcgag | 1080 |
| ggtactcaga caggaagtag cagctccttt gagcatgaga tgtctcagga aggcttcagc | 1140 |
| gctgccatca cctctaatgg cccccttgctg agcactgtgg ggagctatga ctgggctggt | 1200 |
| ggagtctttc tatatacatc aaaggagaaa agcaccttca tcaacatgac agagtggat | 1260 |
| tcagacatga atgatgctta cttgggttat gctgccgcca tcatcttacg gaaccgggtg | 1320 |
| caaagcctgg ttctgggggc acctcgatat cagcacatcg gcctggtagc gatgttcagg | 1380 |
| cagaacactg gcatgtggga gtccaacgct aatgtcaagg cacccagat cggcgcctac | 1440 |
| ttcggggcct ccctctgctc cgtggacgtg acagcaacg gcagcaccga cctggtcctc | 1500 |
| atcggggccc cccattacta cgagcagacc cgaggggcc aggtgtccgt gtgcccttg | 1560 |
| cccaggggc agagggctcg gtggcagtgt gatgctgttc tctacgggga gcagggccaa | 1620 |
| ccctggggcc gctttggggc agccctaaca gtgctggggg acgtaaatgg ggacaagctg | 1680 |
| acggacgtgg ccattgggc cccaggagag gaggacaacc ggggtgctgt ttacctgttt | 1740 |
| cacggaacct caggatctgg catcagcccc tcccatagcc agcggatagc aggctccaag | 1800 |
| ctctctccca ggctccagta ttttggtcag tcactgagtg ggggccagga cctcacaatg | 1860 |
| gatgactgg tagacctgac tgtaggagcc caggggcacg tgctgctgct caggtcccag | 1920 |
| ccagtactga gagtcaaggc aatcatggag ttcaatccca gggaagtggc aaggaatgta | 1980 |
| tttgagtgta atgatcaggt ggtgaaaggc aaggaagccg gagaggtcag agtctgcctc | 2040 |
| catgtccaga agagcacacg ggatcggcta agagaaggac agatccagag tgttgtgact | 2100 |
| tatgacctgc tctggactc cggccgccca cattcccgcg ccgtcttcaa tgagacaaag | 2160 |
| aacagcacac gcagacagac acaggtcttg gggctgaccc agacttgtga gaccctgaaa | 2220 |
| ctacagttgc cgaattgcat cgaggaccca gtgagcccca ttgtgctgcg cctgaacttc | 2280 |
| tctctggtgg gaacgccatt gtctgctttc gggaacctcc ggccagtgct ggcggaggat | 2340 |
| gctcagagac tcttcacagc cttgtttccc tttgagaaga attgtggcaa tgacaacatc | 2400 |
| tgccaggatg acctcagcat caccttcagt ttcatgagcc tggactgcct cgtggtgggt | 2460 |
| gggccccggg agttcaacgt gacagtgact gtgagaaatg atggtgagga ctcctacagg | 2520 |
| acacaggtca ccttcttctt cccgcttgac ctgtcctacc ggaaggtgtc cacactccag | 2580 |
| aaccagcgct cacagcgatc ctggcgcctg gcctgtgagt ctgcctcctc caccgaagtg | 2640 |
| tctggggcct tgaagagcac cagctgcagc ataaaccacc ccatcttccc ggaaaactca | 2700 |
| gaggtcacct ttaatatcac gtttgatgta gactctaagg cttcccttgg aaacaaactg | 2760 |
| ctcctcaagg ccaatgtgac cagtgagaac aacatgccca gaaccaacaa accgaattc | 2820 |
| caactggagc tgccggtgaa atatgctgtc tacatggtgg tcaccagcca tggggtctcc | 2880 |
| actaaatatc tcaacttcac ggcctcagag aataccagtc gggtcatgca gcatcaatat | 2940 |
| caggtcagca acctggggca gaggagcctc cccatcagcc tggtgttctt ggtgcccgtc | 3000 |
| cggctgaacc agactgtcat atgggaccgc ccccaggtca ccttctccga gaacctctcg | 3060 |
| agtacgtgcc acaccaagga gcgcttgccc tctcactccg actttctggc tgagcttcgg | 3120 |
| aaggccccg tggtgaactg ctccatcgct gtctgccaga gaatccagtg tgacatcccg | 3180 |

-continued

```
ttctttggca tccaggaaga attcaatgct accctcaaag gcaacctctc gtttgactgg    3240
tacatcaaga cctcgcataa ccacctcctg atcgtgagca cagctgagat cttgtttaac    3300
gattccgtgt tcaccctgct gccgggacag ggggcgtttg tgaggtccca gacggagacc    3360
aaagtggagc cgttcgaggt cccccaacccc ctgccgctca tcgtgggcag ctctgtcggg    3420
ggactgctgc tcctggccct catcaccgcc gcgctgtaca agctcggctt cttcaagcgg    3480
caatacaagg acatgatgag tgaagggggt cccccggggg ccgaaccca gtagcggctc    3540 cttcccgaca gagctgcctc tcggtggcca gcaggactct cccagacca cacgtagccc    3600 ccaggctgct ggacacgtcg gacagcgaag tatccccgac aggacgggct tgggcttcca    3660
tttgtgtgtg tgcaagtgtg tatgtgcgtg tgtgcgagtg tgtgcaagtg tctgtgtgca    3720
agtgtgtgca cgtgtgcgtg tgcgtgcatg tgcactcgca cgcccatgtg tgagtgtgtg    3780
caagtatgtg agtgtgtcca gtgtgtgtgc gtgtgtccat gtgtgtgcag tgtgtgcatg    3840
tgtgcgagtg tgtgcatgtg tgtgctcagg ggctgtggct cacgtgtgtg actcagagtg    3900
tctctggcgt gtgggtaggt gacggcagcg tagcctctcc ggcagaaggg aactgcctgg    3960
gctcccttgt gcgtgggtaa gccgctgctg gttttcctc cgggagaggg gacggtcaat    4020
cctgtgggtg aagagagagg gaaacacagc agcatctctc cactgaaaga agtgggactt    4080
cccgtcgcct gcgagcctgc ggcctgctgg agcctgcgca gcttggatgg atactccatg    4140
agaaaagccg tgggtggaac caggagcctc ctccacacca gcgctgatgc ccaataaaga    4200
tgcccactga ggaatcatga agcttccttt ctggattcat ttattatttc aatgtgactt    4260
taattttttg gatggataag cctgtctatg gtacaaaaat cacaaggcat tcaagtgtac    4320
agtgaaaagt ctccctttcc agatattcaa gtcacctcct taaaggtagt caagattgtg    4380
ttttgaggtt tccttcagac agattccagg cgatgtgcaa gtgtatgcac gtgtgcacac    4440
accacacaca tacacacaca caagcttttt tacacaaatg gtagcatact ttatattggt    4500
ctgtatcttg ctttttttca ccaatatttc tcagacatcg gttcatatta agacataaat    4560 tacttttca ttcttttata ccgctgcata gtattccatt gtgtgagtgt accataatgt    4620
atttaaccag tcttctttg atatactatt ttcatctctt gttattgcat ctgctgagtt    4680
aataaatcaa atatatgtca aaaaaaaaaa aaaaaaaaa aaaaaaaaa aaaaaaaaa      4740
```

<210> SEQ ID NO 3
<211> LENGTH: 1137
<212> TYPE: PRT
<213> ORGANISM: Artificial sequence
<220> FEATURE:
<223> OTHER INFORMATION: synthetic

<400> SEQUENCE: 3

```
Phe Asn Leu Asp Thr Glu Asn Ala Met Thr Phe Gln Glu Asn Ala Arg
1               5                   10                  15

Gly Phe Gly Gln Ser Val Val Gln Leu Gln Gly Ser Arg Val Val Val
                20                  25                  30

Gly Ala Pro Gln Glu Ile Val Ala Ala Asn Gln Arg Gly Ser Leu Tyr
            35                  40                  45

Gln Cys Asp Tyr Ser Thr Gly Ser Cys Glu Pro Ile Arg Leu Gln Val
        50                  55                  60

Pro Val Glu Ala Val Asn Met Ser Leu Gly Leu Ser Leu Ala Ala Thr
65                  70                  75                  80

Thr Ser Pro Pro Gln Leu Leu Ala Cys Gly Pro Thr Val His Gln Thr
                85                  90                  95
```

```
Cys Ser Glu Asn Thr Tyr Val Lys Gly Leu Cys Phe Leu Phe Gly Ser
            100                 105                 110

Asn Leu Arg Gln Gln Pro Gln Lys Phe Pro Glu Ala Leu Arg Gly Cys
            115                 120                 125

Pro Gln Glu Asp Ser Asp Ile Ala Phe Leu Ile Asp Gly Ser Gly Ser
            130                 135                 140

Ile Ile Pro His Asp Phe Arg Arg Met Lys Glu Leu Val Ser Thr Ile
145                 150                 155                 160

Met Glu Gln Leu Lys Lys Ser Lys Thr Leu Phe Ser Leu Met Gln Tyr
                165                 170                 175

Ser Glu Glu Phe Arg Ile His Phe Thr Phe Lys Glu Phe Gln Asn Asn
            180                 185                 190

Pro Asn Pro Arg Ser Leu Ile Lys Pro Ile Thr Gln Leu Leu Gly Arg
            195                 200                 205

Thr His Thr Ala Thr Gly Leu Arg Lys Val Val Arg Glu Leu Phe Asn
210                 215                 220

Ile Thr Asn Gly Ala Arg Lys Asn Ala Phe Lys Ile Leu Phe Leu Leu
225                 230                 235                 240

Thr Asp Gly Glu Lys Phe Gly Asp Pro Leu Gly Tyr Glu Asp Val Ile
                245                 250                 255

Pro Glu Leu Asp Arg Glu Gly Val Ile Arg Tyr Val Leu Gly Phe Gly
            260                 265                 270

Asp Ala Phe Arg Ser Glu Lys Ser Arg Gln Glu Leu Asn Thr Val Ala
            275                 280                 285

Ser Lys Pro Pro Arg Asp His Val Phe Gln Ala Asn Asn Phe Glu Ala
            290                 295                 300

Leu Lys Thr Val Gln Asn Gln Leu Arg Glu Lys Ile Phe Ala Ile Glu
305                 310                 315                 320

Gly Thr Gln Thr Gly Ser Ser Ser Phe Glu His Glu Met Ser Gln
                325                 330                 335

Glu Gly Phe Ser Ala Ala Ile Thr Ser Asn Gly Pro Leu Leu Ser Thr
            340                 345                 350

Val Gly Ser Tyr Asp Trp Ala Gly Gly Val Phe Leu Tyr Thr Ser Lys
            355                 360                 365

Glu Lys Ser Thr Phe Ile Asn Met Thr Arg Val Asp Ser Asp Met Asn
            370                 375                 380

Asp Ala Tyr Leu Gly Tyr Ala Ala Ala Ile Ile Leu Arg Asn Arg Val
385                 390                 395                 400

Gln Ser Leu Val Leu Gly Ala Pro Arg Tyr Gln His Ile Gly Leu Val
            405                 410                 415

Ala Met Phe Arg Gln Asn Thr Gly Met Trp Glu Ser Asn Ala Asn Val
            420                 425                 430

Lys Gly Thr Gln Ile Gly Ala Tyr Phe Gly Ala Ser Leu Cys Ser Val
            435                 440                 445

Asp Val Asp Ser Asn Gly Ser Thr Asp Leu Val Leu Ile Gly Ala Pro
450                 455                 460

His Tyr Tyr Glu Gln Thr Arg Gly Gly Gln Val Ser Val Cys Pro Leu
465                 470                 475                 480

Pro Arg Gly Gln Arg Ala Arg Trp Gln Cys Asp Ala Val Leu Tyr Gly
                485                 490                 495

Glu Gln Gly Gln Pro Trp Gly Arg Phe Gly Ala Ala Leu Thr Val Leu
            500                 505                 510
```

-continued

Gly Asp Val Asn Gly Asp Lys Leu Thr Asp Val Ala Ile Gly Ala Pro
                515                 520                 525

Gly Glu Glu Asp Asn Arg Gly Ala Val Tyr Leu Phe His Gly Thr Ser
            530                 535                 540

Gly Ser Gly Ile Ser Pro Ser His Ser Gln Arg Ile Ala Gly Ser Lys
545                 550                 555                 560

Leu Ser Pro Arg Leu Gln Tyr Phe Gly Gln Ser Leu Ser Gly Gly Gln
                565                 570                 575

Asp Leu Thr Met Asp Gly Leu Val Asp Leu Thr Val Gly Ala Gln Gly
            580                 585                 590

His Val Leu Leu Arg Ser Gln Pro Val Leu Arg Val Lys Ala Ile
            595                 600                 605

Met Glu Phe Asn Pro Arg Glu Val Ala Arg Asn Val Phe Glu Cys Asn
    610                 615                 620

Asp Gln Val Val Lys Gly Lys Glu Ala Gly Glu Val Arg Val Cys Leu
625                 630                 635                 640

His Val Gln Lys Ser Thr Arg Asp Arg Leu Arg Gly Gln Ile Gln
                645                 650                 655

Ser Val Val Thr Tyr Asp Leu Ala Leu Asp Ser Gly Arg Pro His Ser
                660                 665                 670

Arg Ala Val Phe Asn Glu Thr Lys Asn Ser Thr Arg Arg Gln Thr Gln
            675                 680                 685

Val Leu Gly Leu Thr Gln Thr Cys Glu Thr Leu Lys Leu Gln Leu Pro
            690                 695                 700

Asn Cys Ile Glu Asp Pro Val Ser Pro Ile Val Leu Arg Leu Asn Phe
705                 710                 715                 720

Ser Leu Val Gly Thr Pro Leu Ser Ala Phe Gly Asn Leu Arg Pro Val
                725                 730                 735

Leu Ala Glu Asp Ala Gln Arg Leu Phe Thr Ala Leu Phe Pro Phe Glu
            740                 745                 750

Lys Asn Cys Gly Asn Asp Asn Ile Cys Gln Asp Asp Leu Ser Ile Thr
            755                 760                 765

Phe Ser Phe Met Ser Leu Asp Cys Leu Val Val Gly Gly Pro Arg Glu
            770                 775                 780

Phe Asn Val Thr Val Thr Val Arg Asn Asp Gly Glu Asp Ser Tyr Arg
785                 790                 795                 800

Thr Gln Val Thr Phe Phe Pro Leu Asp Leu Ser Tyr Arg Lys Val
                805                 810                 815

Ser Thr Leu Gln Asn Gln Arg Ser Gln Arg Ser Trp Arg Leu Ala Cys
            820                 825                 830

Glu Ser Ala Ser Ser Thr Glu Val Ser Gly Ala Leu Lys Ser Thr Ser
            835                 840                 845

Cys Ser Ile Asn His Pro Ile Phe Pro Glu Asn Ser Glu Val Thr Phe
850                 855                 860

Asn Ile Thr Phe Asp Val Asp Ser Lys Ala Ser Leu Gly Asn Lys Leu
865                 870                 875                 880

Leu Leu Lys Ala Asn Val Thr Ser Glu Asn Asn Met Pro Arg Thr Asn
                885                 890                 895

Lys Thr Glu Phe Gln Leu Glu Leu Pro Val Lys Tyr Ala Val Tyr Met
            900                 905                 910

Val Val Thr Ser His Gly Val Ser Thr Lys Tyr Leu Asn Phe Thr Ala
            915                 920                 925

Ser Glu Asn Thr Ser Arg Val Met Gln His Gln Tyr Gln Val Ser Asn

```
                930             935             940
Leu Gly Gln Arg Ser Leu Pro Ile Ser Leu Val Phe Leu Val Pro Val
945             950             955             960

Arg Leu Asn Gln Thr Val Ile Trp Asp Arg Pro Gln Val Thr Phe Ser
            965             970             975

Glu Asn Leu Ser Ser Thr Cys His Thr Lys Glu Arg Leu Pro Ser His
            980             985             990

Ser Asp Phe Leu Ala Glu Leu Arg  Lys Ala Pro Val Val  Asn Cys Ser
            995             1000            1005

Ile Ala  Val Cys Gln Arg Ile  Gln Cys Asp Ile Pro  Phe Phe Gly
    1010            1015            1020

Ile Gln  Glu Glu Phe Asn Ala  Thr Leu Lys Gly Asn  Leu Ser Phe
    1025            1030            1035

Asp Trp  Tyr Ile Lys Thr Ser  His Asn His Leu Leu  Ile Val Ser
    1040            1045            1050

Thr Ala  Glu Ile Leu Phe Asn  Asp Ser Val Phe Thr  Leu Leu Pro
    1055            1060            1065

Gly Gln  Gly Ala Phe Val Arg  Ser Gln Thr Glu Thr  Lys Val Glu
    1070            1075            1080

Pro Phe  Glu Val Pro Asn Pro  Leu Pro Leu Ile Val  Gly Ser Ser
    1085            1090            1095

Val Gly  Gly Leu Leu Leu Leu  Ala Leu Ile Thr Ala  Ala Leu Tyr
    1100            1105            1110

Lys Leu  Gly Phe Phe Lys Arg  Gln Tyr Lys Asp Met  Met Ser Glu
    1115            1120            1125

Gly Gly  Pro Pro Gly Ala Glu  Pro Gln
    1130            1135

<210> SEQ ID NO 4
<211> LENGTH: 1137
<212> TYPE: PRT
<213> ORGANISM: Artificial sequence
<220> FEATURE:
<223> OTHER INFORMATION: synthetic

<400> SEQUENCE: 4

Phe Asn Leu Asp Thr Glu Asn Ala Met Thr Phe Gln Glu Asn Ala Arg
1               5               10              15

Gly Phe Gly Gln Ser Val Val Gln Leu Gln Gly Ser Arg Val Val Val
            20              25              30

Gly Ala Pro Gln Glu Ile Val Ala Ala Asn Gln Arg Gly Ser Leu Tyr
        35              40              45

Gln Cys Asp Tyr Ser Thr Gly Ser Cys Glu Pro Ile Arg Leu Gln Val
    50              55              60

Pro Val Glu Ala Val Asn Met Ser Leu Gly Leu Ser Leu Ala Ala Thr
65              70              75              80

Thr Ser Pro Pro Gln Leu Leu Ala Cys Gly Pro Thr Val His Gln Thr
            85              90              95

Cys Ser Glu Asn Thr Tyr Val Lys Gly Leu Cys Phe Leu Phe Gly Ser
            100             105             110

Asn Leu Arg Gln Gln Pro Gln Lys Phe Pro Glu Ala Leu Arg Gly Cys
        115             120             125

Pro Gln Glu Asp Ser Asp Ile Ala Phe Leu Ile Asp Gly Ser Gly Ser
    130             135             140

Ile Ile Pro His Asp Phe Arg Arg Met Lys Glu Trp Val Ser Thr Val
```

```
                145                 150                 155                 160
Met Glu Gln Leu Lys Lys Ser Lys Thr Leu Phe Ser Leu Met Gln Tyr
                    165                 170                 175

Ser Glu Glu Phe Arg Ile His Phe Thr Phe Lys Glu Phe Gln Asn Asn
                    180                 185                 190

Pro Asn Pro Arg Ser Leu Ile Lys Pro Ile Thr Gln Leu Leu Gly Arg
                    195                 200                 205

Thr His Thr Ala Thr Gly Leu Arg Lys Val Val Arg Glu Leu Phe Asn
                    210                 215                 220

Ile Thr Asn Gly Ala Arg Lys Asn Ala Phe Lys Ile Leu Phe Leu Leu
225                 230                 235                 240

Thr Asp Gly Glu Lys Phe Gly Asp Pro Leu Gly Tyr Glu Asp Val Ile
                    245                 250                 255

Pro Glu Leu Asp Arg Glu Gly Val Ile Arg Tyr Val Ile Gly Val Gly
                    260                 265                 270

Asp Ala Phe Arg Ser Glu Lys Ser Arg Gln Glu Leu Asn Thr Val Ala
                    275                 280                 285

Ser Lys Pro Pro Arg Asp His Val Phe Gln Ile Asn Asn Phe Glu Ala
                    290                 295                 300

Leu Lys Thr Ile Gln Asn Gln Leu Arg Glu Lys Ile Phe Ala Ile Glu
305                 310                 315                 320

Gly Thr Gln Thr Gly Ser Ser Ser Phe Glu His Glu Met Ser Gln
                    325                 330                 335

Glu Gly Phe Ser Ala Ala Ile Thr Ser Asn Gly Pro Leu Leu Ser Thr
                    340                 345                 350

Val Gly Ser Tyr Asp Trp Ala Gly Gly Val Phe Leu Tyr Thr Ser Lys
                    355                 360                 365

Glu Lys Ser Thr Phe Ile Asn Met Thr Arg Val Asp Ser Asp Met Asn
                    370                 375                 380

Asp Ala Tyr Leu Gly Tyr Ala Ala Ala Ile Ile Leu Arg Asn Arg Val
385                 390                 395                 400

Gln Ser Leu Val Leu Gly Ala Pro Arg Tyr Gln His Ile Gly Leu Val
                    405                 410                 415

Ala Met Phe Arg Gln Asn Thr Gly Met Trp Glu Ser Asn Ala Asn Val
                    420                 425                 430

Lys Gly Thr Gln Ile Gly Ala Tyr Phe Gly Ala Ser Leu Cys Ser Val
                    435                 440                 445

Asp Val Asp Ser Asn Gly Ser Thr Asp Leu Val Leu Ile Gly Ala Pro
                    450                 455                 460

His Tyr Tyr Glu Gln Thr Arg Gly Gly Gln Val Ser Val Cys Pro Leu
465                 470                 475                 480

Pro Arg Gly Gln Arg Ala Arg Trp Gln Cys Asp Ala Val Leu Tyr Gly
                    485                 490                 495

Glu Gln Gly Gln Pro Trp Gly Arg Phe Gly Ala Ala Leu Thr Val Leu
                    500                 505                 510

Gly Asp Val Asn Gly Asp Lys Leu Thr Asp Val Ala Ile Gly Ala Pro
                    515                 520                 525

Gly Glu Glu Asp Asn Arg Gly Ala Val Tyr Leu Phe His Gly Thr Ser
                    530                 535                 540

Gly Ser Gly Ile Ser Pro Ser His Ser Gln Arg Ile Ala Gly Ser Lys
545                 550                 555                 560

Leu Ser Pro Arg Leu Gln Tyr Phe Gly Gln Ser Leu Ser Gly Gly Gln
                    565                 570                 575
```

-continued

```
Asp Leu Thr Met Asp Gly Leu Val Asp Leu Thr Val Gly Ala Gln Gly
            580                 585                 590
His Val Leu Leu Arg Ser Gln Pro Val Leu Arg Val Lys Ala Ile
            595                 600                 605
Met Glu Phe Asn Pro Arg Glu Val Ala Arg Asn Val Phe Glu Cys Asn
            610                 615                 620
Asp Gln Val Val Lys Gly Lys Glu Ala Gly Glu Val Arg Val Cys Leu
625                 630                 635                 640
His Val Gln Lys Ser Thr Arg Asp Arg Leu Arg Glu Gly Gln Ile Gln
            645                 650                 655
Ser Val Val Thr Tyr Asp Leu Ala Leu Asp Ser Gly Arg Pro His Ser
            660                 665                 670
Arg Ala Val Phe Asn Glu Thr Lys Asn Ser Thr Arg Gln Thr Gln
            675                 680                 685
Val Leu Gly Leu Thr Gln Thr Cys Glu Thr Leu Lys Leu Gln Leu Pro
            690                 695                 700
Asn Cys Ile Glu Asp Pro Val Ser Pro Ile Val Leu Arg Leu Asn Phe
705                 710                 715                 720
Ser Leu Val Gly Thr Pro Leu Ser Ala Phe Gly Asn Leu Arg Pro Val
            725                 730                 735
Leu Ala Glu Asp Ala Gln Arg Leu Phe Thr Ala Leu Phe Pro Phe Glu
            740                 745                 750
Lys Asn Cys Gly Asn Asp Asn Ile Cys Gln Asp Asp Leu Ser Ile Thr
            755                 760                 765
Phe Ser Phe Met Ser Leu Asp Cys Leu Val Val Gly Gly Pro Arg Glu
            770                 775                 780
Phe Asn Val Thr Val Thr Val Arg Asn Asp Gly Glu Asp Ser Tyr Arg
785                 790                 795                 800
Thr Gln Val Thr Phe Phe Pro Leu Asp Leu Ser Tyr Arg Lys Val
            805                 810                 815
Ser Thr Leu Gln Asn Gln Arg Ser Gln Arg Ser Trp Arg Leu Ala Cys
            820                 825                 830
Glu Ser Ala Ser Ser Thr Glu Val Ser Gly Ala Leu Lys Ser Thr Ser
            835                 840                 845
Cys Ser Ile Asn His Pro Ile Phe Pro Glu Asn Ser Glu Val Thr Phe
            850                 855                 860
Asn Ile Thr Phe Asp Val Asp Ser Lys Ala Ser Leu Gly Asn Lys Leu
865                 870                 875                 880
Leu Leu Lys Ala Asn Val Thr Ser Glu Asn Asn Met Pro Arg Thr Asn
            885                 890                 895
Lys Thr Glu Phe Gln Leu Glu Leu Pro Val Lys Tyr Ala Val Tyr Met
            900                 905                 910
Val Val Thr Ser His Gly Val Ser Thr Lys Tyr Leu Asn Phe Thr Ala
            915                 920                 925
Ser Glu Asn Thr Ser Arg Val Met Gln His Gln Tyr Gln Val Ser Asn
            930                 935                 940
Leu Gly Gln Arg Ser Leu Pro Ile Ser Leu Val Phe Leu Val Pro Val
945                 950                 955                 960
Arg Leu Asn Gln Thr Val Ile Trp Asp Arg Pro Gln Val Thr Phe Ser
            965                 970                 975
Glu Asn Leu Ser Ser Thr Cys His Thr Lys Glu Arg Leu Pro Ser His
            980                 985                 990
```

```
Ser Asp Phe Leu Ala Glu Leu Arg  Lys Ala Pro Val Val  Asn Cys Ser
        995                  1000                1005

Ile Ala  Val Cys Gln Arg Ile  Gln Cys Asp Ile Pro  Phe Phe Gly
    1010                 1015                1020

Ile Gln  Glu Glu Phe Asn Ala  Thr Leu Lys Gly Asn  Leu Ser Phe
    1025                 1030                1035

Asp Trp  Tyr Ile Lys Thr Ser  His Asn His Leu Leu  Ile Val Ser
    1040                 1045                1050

Thr Ala  Glu Ile Leu Phe Asn  Asp Ser Val Phe Thr  Leu Leu Pro
    1055                 1060                1065

Gly Gln  Gly Ala Phe Val Arg  Ser Gln Thr Glu Thr  Lys Val Glu
    1070                 1075                1080

Pro Phe  Glu Val Pro Asn Pro  Leu Pro Leu Ile Val  Gly Ser Ser
    1085                 1090                1095

Val Gly  Gly Leu Leu Leu Leu  Ala Leu Ile Thr Ala  Ala Leu Tyr
    1100                 1105                1110

Lys Leu  Gly Phe Phe Lys Arg  Gln Tyr Lys Asp Met  Met Ser Glu
    1115                 1120                1125

Gly Gly  Pro Pro Gly Ala Glu  Pro Gln
    1130                 1135

<210> SEQ ID NO 5
<211> LENGTH: 1137
<212> TYPE: PRT
<213> ORGANISM: Artificial sequence
<220> FEATURE:
<223> OTHER INFORMATION: synthetic

<400> SEQUENCE: 5

Phe Asn Leu Asp Thr Glu Asn Ala Met Thr Phe Gln Glu Asn Ala Arg
1               5                   10                  15

Gly Phe Gly Gln Ser Val Val Gln Leu Gln Gly Ser Arg Val Val Val
            20                  25                  30

Gly Ala Pro Gln Glu Ile Val Ala Ala Asn Gln Arg Gly Ser Leu Tyr
        35                  40                  45

Gln Cys Asp Tyr Ser Thr Gly Ser Cys Glu Pro Ile Arg Leu Gln Val
    50                  55                  60

Pro Val Glu Ala Val Asn Met Ser Leu Gly Leu Ser Leu Ala Ala Thr
65                  70                  75                  80

Thr Ser Pro Pro Gln Leu Leu Ala Cys Gly Pro Thr Val His Gln Thr
                85                  90                  95

Cys Ser Glu Asn Thr Tyr Val Lys Gly Leu Cys Phe Leu Phe Gly Ser
            100                 105                 110

Asn Leu Arg Gln Gln Pro Gln Lys Phe Pro Glu Ala Leu Arg Gly Cys
        115                 120                 125

Pro Gln Glu Asp Ser Asp Ile Ala Phe Leu Val Asp Gly Ser Gly Ser
    130                 135                 140

Ile Ile Pro His Asp Phe Arg Arg Ala Lys Glu Phe Ile Ser Thr Val
145                 150                 155                 160

Met Glu Gln Leu Lys Lys Ser Lys Thr Leu Phe Ser Leu Met Gln Tyr
                165                 170                 175

Ser Glu Glu Phe Arg Ile His Phe Thr Phe Lys Glu Phe Gln Asn Asn
            180                 185                 190

Pro Asn Pro Arg Ser Leu Ile Lys Pro Ile Thr Gln Leu Leu Gly Arg
        195                 200                 205
```

```
Thr His Thr Ala Thr Gly Ile Arg Lys Val Val Arg Glu Leu Phe Asn
210                 215                 220

Ile Thr Asn Gly Ala Arg Lys Asn Ala Phe Lys Ile Leu Ile Leu Ile
225                 230                 235                 240

Thr Asp Gly Glu Lys Phe Gly Asp Pro Leu Gly Tyr Glu Asp Val Ile
                245                 250                 255

Pro Glu Ala Asp Arg Glu Gly Val Ile Arg Tyr Val Ile Gly Val Gly
                260                 265                 270

Asp Ala Phe Arg Ser Glu Lys Ser Arg Gln Glu Leu Asn Thr Val Ala
                275                 280                 285

Ser Lys Pro Pro Arg Asp His Val Phe Gln Ile Asn Asn Phe Glu Ala
290                 295                 300

Leu Lys Thr Ile Gln Asn Gln Leu Arg Glu Lys Ile Phe Ala Ile Glu
305                 310                 315                 320

Gly Thr Gln Thr Gly Ser Ser Ser Phe Glu His Glu Met Ser Gln
                325                 330                 335

Glu Gly Phe Ser Ala Ala Ile Thr Ser Asn Gly Pro Leu Leu Ser Thr
                340                 345                 350

Val Gly Ser Tyr Asp Trp Ala Gly Val Phe Leu Tyr Thr Ser Lys
                355                 360                 365

Glu Lys Ser Thr Phe Ile Asn Met Thr Arg Val Asp Ser Asp Met Asn
370                 375                 380

Asp Ala Tyr Leu Gly Tyr Ala Ala Ile Ile Leu Arg Asn Arg Val
385                 390                 395                 400

Gln Ser Leu Val Leu Gly Ala Pro Arg Tyr Gln His Ile Gly Leu Val
                405                 410                 415

Ala Met Phe Arg Gln Asn Thr Gly Met Trp Glu Ser Asn Ala Asn Val
                420                 425                 430

Lys Gly Thr Gln Ile Gly Ala Tyr Phe Gly Ala Ser Leu Cys Ser Val
                435                 440                 445

Asp Val Asp Ser Asn Gly Ser Thr Asp Leu Val Leu Ile Gly Ala Pro
                450                 455                 460

His Tyr Tyr Glu Gln Thr Arg Gly Gly Gln Val Ser Val Cys Pro Leu
465                 470                 475                 480

Pro Arg Gly Gln Arg Ala Arg Trp Gln Cys Asp Ala Val Leu Tyr Gly
                485                 490                 495

Glu Gln Gly Gln Pro Trp Gly Arg Phe Gly Ala Ala Leu Thr Val Leu
                500                 505                 510

Gly Asp Val Asn Gly Asp Lys Leu Thr Asp Val Ala Ile Gly Ala Pro
                515                 520                 525

Gly Glu Glu Asp Asn Arg Gly Ala Val Tyr Leu Phe His Gly Thr Ser
530                 535                 540

Gly Ser Gly Ile Ser Pro Ser His Ser Gln Arg Ile Ala Gly Ser Lys
545                 550                 555                 560

Leu Ser Pro Arg Leu Gln Tyr Phe Gly Gln Ser Leu Ser Gly Gly Gln
                565                 570                 575

Asp Leu Thr Met Asp Gly Leu Val Asp Leu Thr Val Gly Ala Gln Gly
                580                 585                 590

His Val Leu Leu Leu Arg Ser Gln Pro Val Leu Arg Val Lys Ala Ile
                595                 600                 605

Met Glu Phe Asn Pro Arg Glu Val Ala Arg Asn Val Phe Glu Cys Asn
                610                 615                 620

Asp Gln Val Val Lys Gly Lys Glu Ala Gly Glu Val Arg Val Cys Leu
```

-continued

```
            625                 630                 635                 640
His Val Gln Lys Ser Thr Arg Asp Arg Leu Arg Glu Gly Gln Ile Gln
                645                 650                 655
Ser Val Val Thr Tyr Asp Leu Ala Leu Asp Ser Gly Arg Pro His Ser
                660                 665                 670
Arg Ala Val Phe Asn Glu Thr Lys Asn Ser Thr Arg Arg Gln Thr Gln
                675                 680                 685
Val Leu Gly Leu Thr Gln Thr Cys Glu Thr Leu Lys Leu Gln Leu Pro
            690                 695                 700
Asn Cys Ile Glu Asp Pro Val Ser Pro Ile Val Leu Arg Leu Asn Phe
705                 710                 715                 720
Ser Leu Val Gly Thr Pro Leu Ser Ala Phe Gly Asn Leu Arg Pro Val
                725                 730                 735
Leu Ala Glu Asp Ala Gln Arg Leu Phe Thr Ala Leu Phe Pro Phe Glu
                740                 745                 750
Lys Asn Cys Gly Asn Asp Asn Ile Cys Gln Asp Leu Ser Ile Thr
                755                 760                 765
Phe Ser Phe Met Ser Leu Asp Cys Leu Val Val Gly Gly Pro Arg Glu
            770                 775                 780
Phe Asn Val Thr Val Thr Val Arg Asn Asp Gly Glu Asp Ser Tyr Arg
785                 790                 795                 800
Thr Gln Val Thr Phe Phe Pro Leu Asp Leu Ser Tyr Arg Lys Val
                805                 810                 815
Ser Thr Leu Gln Asn Gln Arg Ser Gln Arg Ser Trp Arg Leu Ala Cys
            820                 825                 830
Glu Ser Ala Ser Ser Thr Glu Val Ser Gly Ala Leu Lys Ser Thr Ser
            835                 840                 845
Cys Ser Ile Asn His Pro Ile Phe Pro Glu Asn Ser Glu Val Thr Phe
            850                 855                 860
Asn Ile Thr Phe Asp Val Asp Ser Lys Ala Ser Leu Gly Asn Lys Leu
865                 870                 875                 880
Leu Leu Lys Ala Asn Val Thr Ser Glu Asn Asn Met Pro Arg Thr Asn
                885                 890                 895
Lys Thr Glu Phe Gln Leu Glu Leu Pro Val Lys Tyr Ala Val Tyr Met
                900                 905                 910
Val Val Thr Ser His Gly Val Ser Thr Lys Tyr Leu Asn Phe Thr Ala
            915                 920                 925
Ser Glu Asn Thr Ser Arg Val Met Gln His Gln Tyr Gln Val Ser Asn
            930                 935                 940
Leu Gly Gln Arg Ser Leu Pro Ile Ser Leu Val Phe Leu Val Pro Val
945                 950                 955                 960
Arg Leu Asn Gln Thr Val Ile Trp Asp Arg Pro Gln Val Thr Phe Ser
                965                 970                 975
Glu Asn Leu Ser Ser Thr Cys His Thr Lys Glu Arg Leu Pro Ser His
                980                 985                 990
Ser Asp Phe Leu Ala Glu Leu Arg  Lys Ala Pro Val Val  Asn Cys Ser
            995                 1000                1005
Ile Ala  Val Cys Gln Arg Ile  Gln Cys Asp Ile Pro  Phe Phe Gly
            1010                1015                1020
Ile Gln  Glu Glu Phe Asn Ala  Thr Leu Lys Gly Asn  Leu Ser Phe
            1025                1030                1035
Asp Trp  Tyr Ile Lys Thr Ser  His Asn His Leu Leu  Ile Val Ser
            1040                1045                1050
```

```
Thr Ala Glu Ile Leu Phe Asn Asp Ser Val Phe Thr Leu Leu Pro
    1055                1060                1065

Gly Gln Gly Ala Phe Val Arg Ser Gln Thr Glu Thr Lys Val Glu
    1070                1075                1080

Pro Phe Glu Val Pro Asn Pro Leu Pro Leu Ile Val Gly Ser Ser
    1085                1090                1095

Val Gly Gly Leu Leu Leu Leu Ala Leu Ile Thr Ala Ala Leu Tyr
    1100                1105                1110

Lys Leu Gly Phe Phe Lys Arg Gln Tyr Lys Asp Met Met Ser Glu
    1115                1120                1125

Gly Gly Pro Pro Gly Ala Glu Pro Gln
    1130                1135

<210> SEQ ID NO 6
<211> LENGTH: 1137
<212> TYPE: PRT
<213> ORGANISM: Artificial sequence
<220> FEATURE:
<223> OTHER INFORMATION: synthetic

<400> SEQUENCE: 6

Phe Asn Leu Asp Thr Glu Asn Ala Met Thr Phe Gln Glu Asn Ala Arg
1               5                   10                  15

Gly Phe Gly Gln Ser Val Val Gln Leu Gln Gly Ser Arg Val Val Val
                20                  25                  30

Gly Ala Pro Gln Glu Ile Val Ala Ala Asn Gln Arg Gly Ser Leu Tyr
            35                  40                  45

Gln Cys Asp Tyr Ser Thr Gly Ser Cys Glu Pro Ile Arg Leu Gln Val
    50                  55                  60

Pro Val Glu Ala Val Asn Met Ser Leu Gly Leu Ser Leu Ala Ala Thr
65                  70                  75                  80

Thr Ser Pro Pro Gln Leu Leu Ala Cys Gly Pro Thr Val His Gln Thr
                85                  90                  95

Cys Ser Glu Asn Thr Tyr Val Lys Gly Leu Cys Phe Leu Phe Gly Ser
            100                 105                 110

Asn Leu Arg Gln Gln Pro Gln Lys Phe Pro Glu Ala Leu Arg Gly Cys
        115                 120                 125

Pro Gln Glu Asp Ser Asp Ile Ala Phe Leu Ile Asp Gly Ser Gly Ser
    130                 135                 140

Ile Ile Pro His Asp Phe Arg Arg Met Lys Glu Phe Val Ser Thr Val
145                 150                 155                 160

Met Glu Gln Leu Lys Lys Ser Lys Thr Leu Phe Ser Leu Met Gln Tyr
                165                 170                 175

Ser Glu Glu Phe Arg Ile His Phe Thr Phe Lys Glu Phe Gln Asn Asn
            180                 185                 190

Pro Asn Pro Arg Ser Leu Val Lys Pro Ile Thr Gln Leu Leu Gly Arg
        195                 200                 205

Thr His Thr Ala Thr Gly Val Arg Lys Val Ile Arg Glu Leu Leu Asn
    210                 215                 220

Ile Thr Asn Gly Ala Arg Lys Asn Ala Phe Lys Ile Leu Ile Val Ile
225                 230                 235                 240

Thr Asp Gly Glu Lys Phe Gly Asp Pro Leu Gly Tyr Glu Asp Val Ile
                245                 250                 255

Pro Glu Ala Asp Arg Glu Gly Val Ile Arg Tyr Val Ile Gly Val Gly
            260                 265                 270
```

```
Asp Ala Phe Arg Ser Glu Lys Ser Arg Gln Glu Leu Asn Thr Ile Ala
        275                 280                 285
Ser Lys Pro Pro Arg Asp His Val Phe Gln Val Asn Asn Phe Glu Ala
    290                 295                 300
Leu Lys Thr Ile Gln Asn Gln Leu Arg Glu Lys Ile Phe Ala Ile Glu
305                 310                 315                 320
Gly Thr Gln Thr Gly Ser Ser Ser Phe His Glu Met Ser Gln
                325                 330                 335
Glu Gly Phe Ser Ala Ala Ile Thr Ser Asn Gly Pro Leu Leu Ser Thr
                340                 345                 350
Val Gly Ser Tyr Asp Trp Ala Gly Val Phe Leu Tyr Thr Ser Lys
            355                 360                 365
Glu Lys Ser Thr Phe Ile Asn Met Thr Arg Val Asp Ser Asp Met Asn
        370                 375                 380
Asp Ala Tyr Leu Gly Tyr Ala Ala Ile Ile Leu Arg Asn Arg Val
385                 390                 395                 400
Gln Ser Leu Val Leu Gly Ala Pro Arg Tyr Gln His Ile Gly Leu Val
                405                 410                 415
Ala Met Phe Arg Gln Asn Thr Gly Met Trp Glu Ser Asn Ala Asn Val
            420                 425                 430
Lys Gly Thr Gln Ile Gly Ala Tyr Phe Gly Ala Ser Leu Cys Ser Val
            435                 440                 445
Asp Val Asp Ser Asn Gly Ser Thr Asp Leu Val Leu Ile Gly Ala Pro
        450                 455                 460
His Tyr Tyr Glu Gln Thr Arg Gly Gly Gln Val Ser Val Cys Pro Leu
465                 470                 475                 480
Pro Arg Gly Gln Arg Ala Arg Trp Gln Cys Asp Ala Val Leu Tyr Gly
                485                 490                 495
Glu Gln Gly Gln Pro Trp Gly Arg Phe Gly Ala Ala Leu Thr Val Leu
                500                 505                 510
Gly Asp Val Asn Gly Asp Lys Leu Thr Asp Val Ala Ile Gly Ala Pro
    515                 520                 525
Gly Glu Glu Asp Asn Arg Gly Ala Val Tyr Leu Phe His Gly Thr Ser
530                 535                 540
Gly Ser Gly Ile Ser Pro Ser His Ser Gln Arg Ile Ala Gly Ser Lys
545                 550                 555                 560
Leu Ser Pro Arg Leu Gln Tyr Phe Gly Gln Ser Leu Ser Gly Gly Gln
                565                 570                 575
Asp Leu Thr Met Asp Gly Leu Val Asp Leu Thr Val Gly Ala Gln Gly
            580                 585                 590
His Val Leu Leu Leu Arg Ser Gln Pro Val Leu Arg Val Lys Ala Ile
        595                 600                 605
Met Glu Phe Asn Pro Arg Glu Val Ala Arg Asn Val Phe Glu Cys Asn
    610                 615                 620
Asp Gln Val Val Lys Gly Lys Glu Ala Gly Glu Val Arg Val Cys Leu
625                 630                 635                 640
His Val Gln Lys Ser Thr Arg Asp Arg Leu Arg Glu Gly Gln Ile Gln
                645                 650                 655
Ser Val Val Thr Tyr Asp Leu Ala Leu Asp Ser Gly Arg Pro His Ser
            660                 665                 670
Arg Ala Val Phe Asn Glu Thr Lys Asn Ser Thr Arg Arg Gln Thr Gln
            675                 680                 685
```

-continued

```
Val Leu Gly Leu Thr Gln Thr Cys Glu Thr Leu Lys Leu Gln Leu Pro
    690                 695                 700

Asn Cys Ile Glu Asp Pro Val Ser Pro Ile Val Leu Arg Leu Asn Phe
705                 710                 715                 720

Ser Leu Val Gly Thr Pro Leu Ser Ala Phe Gly Asn Leu Arg Pro Val
            725                 730                 735

Leu Ala Glu Asp Ala Gln Arg Leu Phe Thr Ala Leu Phe Pro Phe Glu
            740                 745                 750

Lys Asn Cys Gly Asn Asp Asn Ile Cys Gln Asp Asp Leu Ser Ile Thr
            755                 760                 765

Phe Ser Phe Met Ser Leu Asp Cys Leu Val Val Gly Gly Pro Arg Glu
770                 775                 780

Phe Asn Val Thr Val Thr Val Arg Asn Asp Gly Glu Asp Ser Tyr Arg
785                 790                 795                 800

Thr Gln Val Thr Phe Phe Phe Pro Leu Asp Leu Ser Tyr Arg Lys Val
                805                 810                 815

Ser Thr Leu Gln Asn Gln Arg Ser Gln Arg Ser Trp Arg Leu Ala Cys
            820                 825                 830

Glu Ser Ala Ser Ser Thr Glu Val Ser Gly Ala Leu Lys Ser Thr Ser
            835                 840                 845

Cys Ser Ile Asn His Pro Ile Phe Pro Glu Asn Ser Glu Val Thr Phe
850                 855                 860

Asn Ile Thr Phe Asp Val Asp Ser Lys Ala Ser Leu Gly Asn Lys Leu
865                 870                 875                 880

Leu Leu Lys Ala Asn Val Thr Ser Glu Asn Asn Met Pro Arg Thr Asn
                885                 890                 895

Lys Thr Glu Phe Gln Leu Glu Leu Pro Val Lys Tyr Ala Val Tyr Met
            900                 905                 910

Val Val Thr Ser His Gly Val Ser Thr Lys Tyr Leu Asn Phe Thr Ala
            915                 920                 925

Ser Glu Asn Thr Ser Arg Val Met Gln His Gln Tyr Gln Val Ser Asn
930                 935                 940

Leu Gly Gln Arg Ser Leu Pro Ile Ser Leu Val Phe Leu Val Pro Val
945                 950                 955                 960

Arg Leu Asn Gln Thr Val Ile Trp Asp Arg Pro Gln Val Thr Phe Ser
                965                 970                 975

Glu Asn Leu Ser Ser Thr Cys His Thr Lys Glu Arg Leu Pro Ser His
            980                 985                 990

Ser Asp Phe Leu Ala Glu Leu Arg Lys Ala Pro Val Val Asn Cys Ser
            995                 1000                1005

Ile Ala Val Cys Gln Arg Ile Gln Cys Asp Ile Pro Phe Phe Gly
    1010                1015                1020

Ile Gln Glu Glu Phe Asn Ala Thr Leu Lys Gly Asn Leu Ser Phe
    1025                1030                1035

Asp Trp Tyr Ile Lys Thr Ser His Asn His Leu Leu Ile Val Ser
    1040                1045                1050

Thr Ala Glu Ile Leu Phe Asn Asp Ser Val Phe Thr Leu Leu Pro
    1055                1060                1065

Gly Gln Gly Ala Phe Val Arg Ser Gln Thr Glu Thr Lys Val Glu
    1070                1075                1080

Pro Phe Glu Val Pro Asn Pro Leu Pro Leu Ile Val Gly Ser Ser
    1085                1090                1095

Val Gly Gly Leu Leu Leu Leu Ala Leu Ile Thr Ala Ala Leu Tyr
```

```
                    1100                1105                1110
        Lys Leu  Gly Phe Phe Lys Arg  Gln Tyr Lys Asp Met  Met Ser Glu
                    1115                1120                1125

Gly Gly  Pro Pro Gly Ala Glu  Pro Gln
                    1130                1135

<210> SEQ ID NO 7
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 through 6 can be any amino acid.

<400> SEQUENCE: 7

Met Gly Xaa Xaa Xaa Xaa Gly Gly Pro Pro
1               5                   10

<210> SEQ ID NO 8
<211> LENGTH: 7
<212> TYPE: PRT
<213> ORGANISM: Artificial sequence
<220> FEATURE:
<223> OTHER INFORMATION: example

<400> SEQUENCE: 8

Leu Val Leu Val Leu Val Leu
1               5

<210> SEQ ID NO 9
<211> LENGTH: 7
<212> TYPE: PRT
<213> ORGANISM: Artificial sequence
<220> FEATURE:
<223> OTHER INFORMATION: example

<400> SEQUENCE: 9

Leu Pro Leu Pro Leu Val Leu
1               5

<210> SEQ ID NO 10
<211> LENGTH: 7
<212> TYPE: PRT
<213> ORGANISM: Artificial sequence
<220> FEATURE:
<223> OTHER INFORMATION: example

<400> SEQUENCE: 10

Leu Pro Leu Pro Leu Pro Leu
1               5

<210> SEQ ID NO 11
<211> LENGTH: 7
<212> TYPE: PRT
<213> ORGANISM: Artificial sequence
<220> FEATURE:
<223> OTHER INFORMATION: example

<400> SEQUENCE: 11

Leu Pro Pro Pro Leu Val Leu
1               5

<210> SEQ ID NO 12
```

```
-continued

<211> LENGTH: 7
<212> TYPE: PRT
<213> ORGANISM: Artificial sequence
<220> FEATURE:
<223> OTHER INFORMATION: example

<400> SEQUENCE: 12

Leu Pro Pro Val Leu Pro Pro
1               5

<210> SEQ ID NO 13
<211> LENGTH: 7
<212> TYPE: PRT
<213> ORGANISM: Artificial sequence
<220> FEATURE:
<223> OTHER INFORMATION: example

<400> SEQUENCE: 13

Pro Pro Leu Pro Pro Val Pro
1               5
```

PROTEINS WITH INTEGRIN-LIKE ACTIVITY

This application claims the benefit of the priority date of U.S. Ser. No. 60/216,600, filed Jul. 7, 2000.

The U.S. Government has certain rights in this invention pursuant to Grant No. CA 31799 awarded by the National Institute of Health.

FIELD OF THE INVENTION

The invention relates to novel integrin and I domain proteins and nucleic acids. This invention further relates to the use of such proteins and nucleic acids in the treatment of integrin related disorders.

BACKGROUND OF THE INVENTION

Integrins are glycoprotein cell adhesion receptors that mediate cell-cell (via counter receptors on other cells) and cell-substrate (i.e. cell-extra cellular matrix) interactions [Aplin at al., Pharmacological Reviews 50:199–252 (1998)]. Integrins function generally to maintain tissue integrity, cellular migration, provide physical support for cells, allow for cohesion between cells, permits the generation of traction forces which enable movement, and to organize signaling complexes which modulate differentiation, cell fate, and apoptosis. Additionally, the properties of the individual integrins depend upon which subunits it contains and which cells they are expressed in. For example, the leukocyte integrins mediate several adhesive events that are crucial for immune system function. They promote the adhesion that is required for T lymphocyte target cell lysis [Davignon, et al., Proc. Natl. Acad. Sci. USA 78:4535–4539 (1981)], T lymphocyte proliferation [Davignon, et al., Proc. Natl. Acad. Sci. USA 78:4535–4539 (1981)], natural killing [Krensky et al., J. Immunol 131:611–616 (1983)], leukocyte adhesion to, and migration through endothelial cells [Dustin et al., J. Cell Biol. 107:321–331 (1988); Harlan et al., Blood 66:167–178 (1985); Haskard et al, J. Immunol. 137:2901–2906 (1986); Lo et al., J. Exp. Med. 169:1779–1793 (1989); Lo et al., J. Immunol. 143(10):3325–3329 (1989); Smith, et al., J. Clin. Invest. 83:2008–2017 (1989); Smith, et al., J. Clin. Invest. 82:1746–1756 (1988)], neutrophil homotypic aggregation, and neutrophil chemotaxis [Anderson, et al., J. Immunol. 137:15–27 (1986)].

Each integrin is a heteroduplex consisting of an alpha subunit and a beta subunit. There are currently 19 different alpha subunits and 8 different beta subunits, perhaps making the integrins the most structurally and functionally diverse family of cell adhesion molecules [e.g. see Springer, T. A. Nature 346:425–433(1990); Smyth et al., Blood 81:2527–2843 (1993); Springer, T. A. Proc. Natl. Acad. Sci. 94:65–72 (1997); Humpries, M. J. Biochem. Soc. Trends 28(4):311–339 (2000)].

Each subunit contains a transmembrane domain anchoring the major portion of the wild-type protein to the external side of the cell's membrane.

Each subunit has a large extracellular domain, a single transmembrane domain and usually a relatively short transmembrane domain [Aplin at al., Pharmacological Reviews 50:199–252 (1998)]. The pairing of a particular alpha subunit with a particular beta subunit in part determines the ligand-binding characteristics of the integrin protein. As such, both of the subunits can alter the binding characteristics of the integrin protein. Studies of integrin binding characteristics have focused on three areas: a) a series of seven repeats near the N-terminal portion of the alpha subunit, b) an inserted domain (I-domain also known as an "A domain") in the alpha subunit, and c) an "I-domain like region" located in the beta subunit [(Loftus & Liddington, J. Clin. Invest. 99:2302–2306 (1997)].

The functional integrin protein appears to exist in two different states, open (activated or high affinity) and closed ("inactivated" or "low affinity"). The open state allows the integrin protein to bind to its appropriate ligand, while the closed state is relatively inert. The ability of integrins to bind to ligands depends upon internal cell messages, as well as the presence or absence of divalent cations such as $Mg^{+2}$ or $Ca^{+2}$ [(Springer, Proc. Natl. Acad. Sci. 94:65–72 (1997)]. This regulation of binding affinity integrin is believed to be due to the different conformational states that integrin can exist in. Signals which after this conformation, either internal cell signals or divalent cations, bias the stability of each conformational state of integrin into an "open" or "closed" conformation.

The leukocyte integrin subfamily includes four members, LFA-1 (CD11a/CD18), Mac-1 (CD11b/CD18), p150,95 (CD11c/CD 18), and alphaDBeta2 that share a common.beta subunit that is noncovalently associated with unique but closely related alpha chains [Kishimoto et al., Adv. Immunol. 46:149–182 (1989); Springer, Nature 346:425–433 (1990)]. These glycoproteins share a common CD18 beta subunit (95,000 MW) but have individual unique CD11 alpha subunits (175,000, 160,000, 150,000 MW) respectively, that are structurally homologous [Larson, et al., J. Cell Biol. 108:703–712 (1989)]. All four members share two prominent features in the extracellular region of the molecule, a putative divalent cation binding region consisting of three tandem repeats of an EF-hand motif, and approximately a 200 amino acid inserted or "I" domain [Arnaout, et al., J. Cell Biol. 106:2153–2158 (1988); Corbi, et al., J. Biol. Chem. 263:12403–12411 (1988); Corbi, et al., EMBO J. 6:4023–4028 (1987); Kaufman, et al., J. Immunol. 147:369–371 (1991); Larson, et al., J. Cell Biol. 108:703–712 (1989); Pytela, EMBO J. 7:1371–1378 (1988)].

Mac-1 plays a central role in promoting neutrophil inflammatory responses, and its use as a target in medical research has shown promise in treating autoimmune diseases and ischemia/reperfusion. It is expressed on the cell surface as well as in an intracellular, vesicular compartment in circulating neutrophils and monocytes which is mobilized to the cell surface by inflammatory mediators [Todd, et al., J. Clin. Invest. 74:1280–1290 (1984); Springer, et al., In: Biochemistry of Macrophages (CIBA Symposium 118), Pitman, London, pp. 102–126 (1986); Lanier, et al., Eur. J. Immunol. 15:713–718 (1985); Yancey, et al., J. Immunol. 135:465–470 (1985)].

The I domain of Mac-1 contains 184 residues and is implicated in the integrin's binding to protein ligands [Michishita et al., Cell 72:857–867 (1993); Diamond et al., J. Cell Biolo. 120:1031–1043 (1993); Lee et al., Structure 3:1333–1340]. Mac-1 can bind to iC3b, intercellular adhesion molecule-1 (ICAM-1, ICAM-2 and fibrinogen) as well as Factor X. I domains in the broader category of integrins may also bind to various collagen isotypes (I and IV) as well as laminin. [Humphries, Biochemistry Society 28:311–339 (2000)]. Crystal structures of I domains reveal a dinucleotide-binding fold, with a metal ion-dependent adhesion site (MIDAS) on the top face [Lee et al. Structure 3:1333–1340 (1995); Lee et al. Cell 80:631–638 (1995); Qu & Leahy, Proc. Natl. Acad. Sci. U.S.A. 92:10277–10281 (1995); Qu & Leahy, Structure 4:931–942 (1996); Emsley et al. J. Biol. Chem. 272:28512–28517 (1997); Baldwin et al., Structure 6:923–935 (1998); Nolte et al., FEBS Lett. 452:379–385 (1999); Rich et al., J. Biol. Chem. 274:24906–24913 (1999)]. The metal ion ligates an acidic residue in protein ligands, and is surrounded by residues that contact the ligand [Lee et al., Structure 3:1333–1340(1995); Huang and Springer, J. Biol. Chem. 270:19008–19016 (1995); Li et al., J. Cell Biol. 143:1523–1534(1998); Zhang et al., Biochemistry 38:8064–8071 (1999)]. The bottom of the I domain connects to a putative integrin beta-propeller domain [Springer, Proc. Natl. Acad. Sci U.S.A. 94:65–72 (1997)].

Two different crystal forms of the Mac-1 I domain, termed open and closed, respectively, are hypothesized to represent the I domain in active (or ligand binding) and inactive (ligand nonbinding) conformations. [Lee et al., Structure 3:1333–1340 (1995); Lee et al., Cell 80:631–638 (1995)]. Although experimental data support this idea [Li et al., J. Cell Biol. 143:1523–1534 (1998); Oxvig et al., Proc. Natl. Acad. Sci. U.S.A. 96:2215–2220 (1999)] it has remained controversial because many other I-domain structures, including those from other alpha subunits, have failed to reveal a corresponding open conformation. [Qu et al., Proc. Natl. Acad. Sci. U.S.A. 92:10277–10281 (1995); Qu et al., Structure 4:931–942 (1996); Emsley et al., J. Biol. Chem. 272:28512–28517 (1997); Baldwin et al., Structure 6:923–935 (1998); Nolte et al., FEBS Lett. 452:379–385 (1999) Rich et al., J. Biol. Chem. 274:24906–24913 (1999)]. However, a recent co-crystal of the alph2 I domain bound to a triple-helical collagen peptide ligand reveals an open conformation very similar to that described for alpha M. [Emsley et al., Cell 101:47–56 (2000)]. Between the closed and open structures, three residues that directly coordinate the metal differ, in position, and other nearby residues shift in position. These movements appear to be structurally linked to a dramatic, 10 Å movement in the C-terminal alpha helix. The structurally homologous G-protein alpha subunit undergoes a similar change in metal coordination between the GDP- and GTP-bound forms, which is coupled to long-range structural rearrangements [Lee et al., Structure 3:1333–1340 (1995)].

One of the ligand binding sites for Mac-1 is believed to be near MIDAS. [Huang & Springer J. Biol. Chem. 270:19008–19016 (1995)].

Mutations that stabilize one protein conformation relative to another have previously been found empirically, for example in hemoglobin [Perutz, Q. Rev. Biophys 22:139–237 (1989)]; furthermore, visual inspection by experts has been used to predict mutations that stabilize the open conformer of the Mac-1 I domain [Li et al., J. Cell Biol. 143:1523–1534 (1998)].

Recently, advances have been made in computational design. Several groups have applied and experimentally tested systematic, quantitative methods to protein design with the goal of developing general design algorithms (Hellinga et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. U.S.A. 92:8408–8412 (1995); Klemba et al., Nat. Struc. Biol. 2:368–373 (1995); Nautiyal et al., Biochemistry 34:11645–11651 (1995); Betzo et al., Biochemistry 35:6955–6962 (1996); Dahiyat et al., Protein Science 5:895–903 (1996); Dahiyat et al., Science 278:82–87 (1997); Dahiyat et al., J. Mol. Biol. 273:789–96; Dahiyat et al., Protein Sci. 6:1333–1337 (1997); Jones, Protein Science 3:567–574 (1994); Konoi, et al., Proteins: Structure, Function and Genetics 19:244–255 (1994)). These algorithms consider the spatial positioning and steric complementarity of side chains by explicitly modeling the atoms of sequences under consideration. In particular, WO98/47089, and U.S. Ser. No. 09/127,926 describe a system for protein design; both are expressly incorporated by reference. With the assistance of these programs mutations have been designed that enhance the stability of small proteins (on the order of 60 residues) [Dahiyat et al., Science 278:82–87 (1997); Malakauskas, & Mayo, Nature Struc. Biol. 5:470–475 (1998)].

Because of the huge functional difference between the two states of the integrin protein, substances which bias one state of the protein over another can provide an effective method of altering the concentration and activity of integrin and dealing with any integrin related problems. Additionally, the ability to monitor the various states that these proteins exist in a state dependent manner is also possible due to the current invention because known populations of single state integrins may be screened against possible probes selective only for that state.

Accordingly, it is an object of the invention to provide conformationally biased integrins for the treatment of diseases in which integrins have been implicated, including but not limited to: autoimmune diseases, inflammatory diseases, transplant rejections, apoptosis, and various forms of shock (i.e. hypovolemic or cerebral), the existence of such conformationally biased proteins will enable more effective drug and antibody design to help with these disorders.

SUMMARY OF THE INVENTION

In accordance with the objects outlined above, the present invention provides structurally biased variant integrin and I domain proteins comprising amino acid sequences with at least three amino acid changes compared to the wild-type integrin or I domain proteins. Preferred embodiments utilize variant integrins or I domains that are structurally biased to exist in either the open or the closed conformation, altering the protein's binding ability. Preferably, variant integrin or I domain proteins with 1, 2, 3, 4, and 5 amino acid changes are used as compared to wild-type protein. In a preferred embodiment these changes are selected from positions 139, 153, 156, 157, 160, 199, 215, 219, 223, 238, 239, 240, 259, 269, 271, 287, 299, 308.

In an additional aspect, the invention provides recombinant nucleic acids encoding the variant integrin or I domain proteins, expression vectors, and host cells.

In an additional aspect, the invention provides a method for screening for modulators that bind to either the structurally biased open integrin or I domain, or modulators that bind to the structurally biased closed integrin or I domain. The screen may provide modulators that bind selectively to one state.

In an additional aspect, the invention provides a method for making antibodies against the structurally biased integrin or I domain; the antibodies may be monoclonal. The antibodies may bind selectively to the structurally biased open integrin or I domain and not the structurally biased closed integrin or I domain, or vice versa.

In a further aspect, the invention provides methods for treating an integrin related disorder comprising administering a variant integrin or I domain protein of the invention to a patient.

BRIEF DESCRIPTION OF THE DRAWINGS

FIG. 1. Stereoview of mutations in the Mac-1 I-domain open structures (active/high affinity/ido). FIG. 1A depicts wild type 1ido (open) structure. FIG. 1B depicts the structure computed for the ido1q (open) mutant. FIG. 1C depicts the structure computed far the ido1r (open) mutant. FIG. 1D depicts the structure computed for the ido2r (open) mutant. Mutant sequences and rotamers were computed as described herein. A cavity was detected in the wild-type 1ido structure but not in the designed mutants, using VOIDOO (Kleywegt et al., Acta Cryst 050:178–185 (1994)) (with a probe of 1.4 Å, a van der Waals growth factor of 1.1, and a minimum of 5 voxels. The cavity is 202 Å$^3$ in 1ido. The cavity is filled by mutations V238F and V160I in ido1q (FIG. 1B), V238F and F156W in ido1r (FIG. 1C), and V238I in ido2r (FIG. 1D). Figure made with Ribbons (Carson, Methods in Enzymology 277:493–505). FIG. 1E is a cartoon representation of a complete integrin heterodimer. The black circles represent bivalent cation binding sites. FIG. 1F depicts the amino acid sequence of Mac-1 alpha subunit of integnn (SEQ ID NO:1). FIG. 1G depicts the nucleotide sequence of Mac-1 alpha subynit of integrin (SEQ ID NO:2).

FIG. 2. Intact Mac-1 molecules with computationally designed I domains are more active than wild-type in binding ligands when transiently expressed in 293T cells. Wild-type alphaM or alphaM with mutant I domains were expressed transiently in 293T cells in association with wild-type beta2. FIG. 2A depicts CBRM1/5 monoclonal antibody binding. Binding of the activation-dependent antibody CBRM1/5, was determined by flow-cytometry as specific mean fluorescence intensity and expressed as a percentage of wild-type. FIG. 2B depicts binding of transfectants to immobilized iC3b. Wild-type Mac-1 in 293T cells is basally active but can be further activated by the activating beta2-chain monoclonal antibody, CBR LFA1/2. FIG. 2C shows a comparison of CBRM1/5 binding between the computationally-designed mutant ido2r and the expert-designed mutant F302W. FIG. 2D shows a comparison of ligand binding between ido2r and F302W. In (FIGS. 2A, 2B, 2C, and 2D) values are normalized to those of wild-type by the binding of CBRM1/20 monoclonal antibody which recognizes the beta-propeller domain of alphaM, and are expressed as mean±S.E.M. of values in FIG. 3 (A&B) or FIG. 2 (C&D) independent experiments in duplicate.

FIG. 3. alphaM beta2 heterodimers with computationally designed open and closed I-domains are active in binding iC3b, and resistant to activation, respectively, when stably expressed in K562 cells. FIGS. 3A&3B show immunofluorescence flow cytometry. FIG. 3C depiscts binding of transfectants to immobilized iC3b. Binding of wild-type was tested in the presence and absence of CBR LFA1/2, an activating monoclonal antibody to the beta2 subunit. FIG. 3D depicts the effect of blocking or activating monoclonal antibody. Transfectants were incubated in the presence of X63 as control IgG (white bar), monoclonal antibody CBR LFA1/2 (central black bar) or the activation-dependent and inhibitory I domain monoclonal antibody CBRM1/5 (right black bar that may be too short to see). In FIGS. 3B, 3C and 3D, the values were normalized by the ratio of mutant/wild-type CBRM1/20 monoclonal antibody specific fluorescence intensity and expressed as mean±S.E.M of three independent experiments.

FIG. 4. Isolated, computationally designed open I-domain mutants bind ligands, whereas wild-type and designed closed I-domains do not. FIG. 4A depicts the binding of 293T transient transfectants to iC3b. Binding was performed in L15 medium/FBS which contains $Mg^{2+}$ and $Ca^{2+}$, with 1 mM $Mn^{2+}$. FIG. 4B depicts the binding of K562 transfectants to iC3b, and enhancement with $Mn^{2+}$. Binding was performed in L15 medium/FBS which contains $Mg^{2+}$ and $Ca^{2+}$, without (white bar) or with (black bar) 1 mM $Mn^{2+}$. FIG. 4C depicts the binding of K562 transfectants to iC3b in the presence or absence of divalent cation. Binding was performed in HEPES/NaCl/glucose supplemented with 1 mM $Mn^{2+}$ (black bar) or 2 mM EDTA (white bar, values are zero in all columns). Immunofluorescent staining with monoclonal antibody (monoclonal antibody) to a c-myc tag (Invitrogen) and CBRM1/1 and CBRM1/2 monoclonal antibody to the I domain showed expression of the 1r and 2r mutants was 90 and 93% of wild-type, respectively.

FIG. 5 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 6 depicts a preferred scheme for synthesizing an integrin protein library of the invention. The wild type gene, or any starting gene, such as the gene for the global minima gene, can be used. Oligonucleotides comprising sequences that encode different amino acids at the different variant positions (indicated in the Figure by box 1, box 2, and box 3) can be used during PCR. Those primers can be used in combination with standard primers. This generally requires fewer oligonucleotides and can result in fewer errors.

FIG. 7 depicts an overlapping extension method. At the top of FIG. 7 is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. Thus, as shown in this example, oligos R1 and F2 comprise a region of homology and so do oligos R2 and F3. In this example, three separate PCR reactions are done for step 1. The first reaction contains the template plus oligos F1 and R1. The second reaction contains template plus oligos F2 and R2, and the third contains the template and oligos F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers, F1 and R4. In Step 3, the purified product from Step 2 is used in a third PCR reaction, together with the product of Step 1, tube 3 and the primers F1 and R3. The final product corresponds to the full length gene and contains the required mutations. Alternatively, Step 2 and Step 3 can be performed in one PCR reaction.

FIG. 8 depicts a ligation of PCR reaction products to synthesize the libraries of the invention. In this technique, the primers also contain an endonuclease restriction site (RE), either generating blunt ends, 5' overhanging ends or 3' overhanging ends. We set up three separate PCR reactions for Step 1. The first reaction contains the template plus oligos F1 and R1. The second reaction contains template plus oligos F2 and R2, and the third contains the template and oligos F3 and R3. The reaction products are shown. In Step 2, the products of Step 1 are purified and then digested with the appropriate restriction endonuclease. The digestion products from Step 2, tube 1 and Step 2, tube 2 are ligated together with DNA ligase (Step 3). The products are then amplified in Step 4 using oligos F1 and R4. The whole process is then repeated by digesting the amplified products, ligating them to the digested products of Step 2, tube 3, and then amplifying the final product using oligos F1 and R3. It would also be possible to ligate all three PCR products from Step 1 together in one reaction, providing the two restriction sites (RE1 and RE2) were different.

FIG. 9 depicts blunt end ligation of PCR products. In this technique, oligos such as F2 and R1 or R2 and F3 do not overlap, but they abut. Again three separate PCR reactions are performed. The products from tube 1 and tube 2 (see FIG. (8A, Step 1) are ligated, and then amplified with outside primers F1 and R4. This product is then ligated with the product from Step 1, tube 3. The final products are then amplified with primers F1 and R3.

DETAILED DESCRIPTION OF THE INVENTION

The present invention is directed to novel proteins and nucleic acids having characteristics similar to the integrin family. The proteins are generated using a system previously described in WO98/47089 and U.S. Ser. Nos. 09/058,459, 09/127,926, 60/104,612, 60/158,700, 09/419,351, 60/181,630, 60/186,904, and U.S. patent application Ser. No. 09/784,004, entitled—Protein Design Automation For Protein Libraries (Filed: Apr. 14, 2000; Inventor: Bassil Dahiyat), all of which are expressly incorporated by reference in their entirety. These applications are directed to computational modeling systems that allows the generation of extremely stable proteins without necessarily disturbing the biological functions of the protein itself. In this way, novel integrin proteins and nucleic acids are generated, that can have a plurality of mutations in comparison to the wild-type receptor yet retain significant activity. In addition, modelling can be done based on either or both of the "open" and "closed" conformations.

Generally, there are a variety of computational methods that can be used to generate the variant integrin proteins of the invention. In a preferred embodiment, sequence based methods are used. Alternatively, structure based methods, such as PDA, described in detail below, are used.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1–8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate the variant integrin proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

As is known in the art, there are a number of sequence alignment methodologies that can be used. For example, sequence homology based alignment methods can be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of variant integrin proteins.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a variant integrin library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused library of variant integrin proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments (Orengo et al., Structure 5(8):1093–108 (1997); Holm et al., Nucleic Acids Res. 26(1):316–9 (1998), both of which are incorporated by reference). These sequence alignments can then be examined to determine the observed sequence variations. Libraries can be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016):164–70, (1991)], rotamer library selections [Dahiyat and Mayo, Protein Sci. 5(5):895–903 (1996); Dahiyat and Mayo, Science 278(5335):82–7 (1997); Desjarlais and Handel, Protein Science 4:2006–2018 (1995); Harbury et al Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], and other inverse folding methods such as those described by Simons et al. [Proteins, 34:535–543, (1999)], Levitt and Gerstein [Proc. Natl. Acad. Sci. U.S.A., 95:5913–5920, (1998)], Godzik and Skolnick [Proc. Natl. Acad. Sci. U.S.A., 89:12098–102, (1992)], Godzik et al. [J. Mol. Biol. 227:227–38, (1992)] and two profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference. In addition, other computational methods such as those described by Koehl and Levitt (J. Mol. Biol. 293:1161–1181 (1999); J. Mol. Biol. 293:1183–1193 (1999); expressly incorporated by reference) can be used to create a variant integrin library which can optionally then be used to generate a smaller variant integrin library for use in experimental screening for improved properties and function. In addition, there are computational methods based on forcefield calculations such as SCMF that can be used as well for SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Mol Biol. 293:1183–93 (1999); Koehl et al., J. Mol. Biol. 293:1161–81 (1999); Lee J., Mol. Biol. 236:918–39 (1994); and Vasquez Biopolymers 36:53–70 (1995); all of which are expressly incorporated by reference. Other forcefield calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc.112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3 [Liwo et al., J Protein Chem. 13(4):375–80 (1994)]; AMBER 1.1 force field (Weiner et al., J. Am. Chem. Soc. 106:765–784); AMBER 3.0 force field [U. C. Singh et al., Proc. Natl. Acad. Sci. U.S.A., 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:31–47 (1988)]; cff91 (Maple et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these forcefield methods may be used to generate the variant integrin library directly; these methods can be used to generate a probability table from which an additional library is directly generated.

In a preferred embodiment, the computational method used to generate the set or library of variant integrin proteins is Protein Design Automation (PDA), as is described in U.S. Ser. Nos. 60/061,097, 60/043,464, 60/054,678, 09/127,926, 60/104,612, 60/158,700, 09/419,351, 60/181,630, 60/186,904, 09/419,351, and an application entitled "Protein Design Automation for Protein Libraries", filed (U.S. Ser. No. 09/784,004) and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occurring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc. In the present invention, it is the tetramerization domain residues which are varied, as outlined below.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modeling. Alternatively, a preferred embodiment utilizes an assessment of the orientation of the Cα-Cβ vectors relative to a solvent accessible surface computed using only the template Cα atoms, as outlined in U.S. Ser. Nos. 60/061,097, 60/043,464, 60/054, 678, 09/127,926 60/104,612, 60/158,700, 09/419,351, 60/181,630, 60/186,904, 09/419,351 and an application entitled "Protein Design Automation for Protein Libraries" filed Feb. 12, 2001 (U.S. Ser. No. 09/784,004) and PCT US98/07254. Alternatively, a surface area calculation can be done.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic salvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec} \qquad \text{Equation 1}$$

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926, 60/104,612, 60/158,700, 09/419,351, 60/181,630, 60/186,904, 09/419,351, and an application entitled "Protein Design Automation for Protein Libraries", filed Feb. 12, 2001 (U.S. Ser. No. 09/784,004) and PCT US98/07254, all of which are expressly incorporated by reference, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 6–10 amino acid residues to the entire amino acid sequence minus one amino acid. Accordingly, the term "portion", as used herein, with regard to a nucleic refers to a fragment of that nucleic acid. This fragment may range in size from 10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PDA calculations can be used, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2 [Allinger, J. Chem. Soc. 99:8127 (1977), Liljefors et al., J. Com. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3 [Allinger et al., J. Amer. Chem. Soc. 111:8551 (1989)], OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc. 11 2:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A 96:5482–5485 (1999)]; ECEPP/3 [Liwo et al., J Protein Chem. 13(4):375–80 (1994)]; AMBER 1.1 force field (Weiner, et al., J. Am. Chem. Soc. 106:765–784); AMBER 3.0 force field (U. C. Singh et al., Proc. Natl. Acad. Sci. U.S.A. 82:755–759); CHARMM and CHARMM22 (Brooks et al., J. Comp. Chem. 4:187–217); cvff3.0 [Dauber-Osguthorpe, et al., Proteins: Structure, Function and Genetics, 4:3147 (1988)]; cff91 (Maple, et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 09/127,926 and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique. In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Mayo, Structure Fold. Des. 7:1089–98, 1999), and exhaustive enumeration of sequences.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted can be altered.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artificial Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the variant integrin library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods can be used to further process a first set to generate additional sets of variant integrin proteins.

As used herein variant integrin proteins include variant integrin monomers or isolated parts of the integrin protein containing variant I domains.

As used herein variant I domain proteins include proteins or fragments thereof that need not be integrins.

The computational processing results in a set of optimized variant integrin protein sequences. Optimized variant integrin protein sequences are generally different from the wild-type integrin sequence in structural regions critical for receptor affinity or regions responsible for signal transduction or regions for dimerization of the protein. Preferably, each optimized variant integrin protein sequence comprises at least about 1 variant amino acid from the starting or wild type sequence, with 3–5 being preferred. Preferably, the variant residues are located in noncontiguous regions.

Accordingly, in a preferred embodiment, the present invention is directed to methods of computationally processing a wild type integrin, or fragment thereof, to produce variant integrin proteins.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid representing a component of the integrin proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22 1998 and Tang et al., Abstr. Pap Am. Chem. S218:U138–U138 Part 2 Aug. 22, 1999, both of which are expressly incorporated by reference herein.

The variant integrin proteins and nucleic acids of the invention are distinguishable from naturally occurring integrins. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in viva cellular machinery of the host cell rather than in vitro manipulations, however, such nucleic acids, once produced recombinantly, although subsequently replicated non-recombinantly, are still considered recombinant for the purpose of the invention. A representative amino acid sequences of a naturally occurring human integrin is shown in FIG. 1F (SEQ ID NO:1). It should be noted that unless otherwise stated, all positional numbering of integrin proteins and integrin nucleic acids is based on these sequences (with position 1 equivalent to position 17 of FIG. 1F). That is, as will be appreciated by those in the art, an alignment of integrin proteins can be done using standard programs, as is outlined below, with the identification of "equivalent" positions between the two proteins. Thus, the variant integrin proteins and nucleic acids of the invention are non-naturally occurring; that is, they do not exist in nature.

The variant integrin proteins may be from any number of organisms, with integrin proteins from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (the sequence of which is depicted in FIG. 1F). As will be appreciated by those in the art, variant integrin proteins based on integrin proteins from mammals other than humans may find use in animal models of human disease.

Integrin proteins may be involved in any number of pathways, including but not limited to pathways involved in membrane signaling, such as MAP kinase cascades (for a review s see, Yamada and Miyamoto, 1995; Brakebusch et al, 1997; Hynes and Bader, 1997; Shattil et al, 1998; Aplin et al, 1998; Giancotti and Ruoslahti, 1999; Schwatz and Baron, 1999). Suitable integrins include, but are not limited to those found in leukocytes, osteoplasts and any functional combination of the 18 alpha and 8 beta subunits presently discovered as described in Humphries (2000), and the above references.

The term "integrin" can include either the alpha or beta subunit of an integrin, or both. By "subunit" herein is meant either the alpha or the beta subunits of the protein, one of each subunit is required to achieve functionality for the wild-type integrin protein. There are currently 19 alpha and 8 beta subunits known in mammals.

The wild type starting integrin sequence can be full-length, or a functional domain thereof. Thus, in a preferred embodiment, the starting sequence is an I domain. By "I domain" herein is meant the "I domain" or the "A domain" or other equivalent term (for a list of reviews see Humphries, (Biochemical society 28:311–339 2000, herein expressly incorporated by reference). Generally, this domain is a 200-residue section of protein which is homologous to the cation-binding A-domain of von Willebrand factor and is usually found between repeats 2 and 3 in the alpha subunit- when the I domain is located in an integrin. Such a domain may, but need not be part of an integrin protein. A nonexhaustive list of examples of such I domains in integrin include those found in the alpha 1, alpha 2, alpha 10, alpha X, alpha D, alpha L, and alpha M (a component of the leukocyte integrin). Not all integrins contain I domains, those integrins without I domains are not relevant to the current invention. Those integrins with I domains, either as a wild-type entity or artificially added, are included in the field of this invention if the I domain is artificially biased as described in claim 1.

In one embodiment, non-integrin variant I domains are included in the invention.

Thus, the invention provides methods for the generation of variant integrins. By "variant integrin proteins", "structurally biased integrin", "conformationally biased integrin", "variant integrin", or grammatical equivalent, herein is meant that the integrin proteins of the invention are non-naturally occurring integrin proteins.

Thus, in a preferred embodiment, the variant integrin proteins of the invention have an amino acid sequence that differs from a wild-type integrin sequence by at least 2% of the residues. That is, the variant integrin proteins of the invention are less than about 98% identical to an integrin amino acid sequence. Accordingly, a protein is an "integrin protein" if the overall homology of the protein sequence to the amino acid sequence shown in FIG. 1F is preferably less than about 98%, more preferably less than about 95%, even more preferably less than about 90% and most preferably less than 85%. In some embodiments the homology will be as low as about 75 to 80%. In other embodiments the homology will be as low 50–70%. Stated differently, based on the human integrin sequence of 51 residues (see FIG. 1F), variant integrin proteins have at least about 1 residue that differs from the human integrin sequence (2%), with variant integrin proteins having from 2 residues to upwards of 25 residues being different from the human integrin sequence. Preferred variant integrin proteins have 1–20 different residues with from about 2 to about 10 being particularly preferred (that is, 4–20% of the protein is not identical to human integrin).

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karlin et al., Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1, it is understood that in one embodiment, the percentage of sequence identity will be determined based on the number of identical amino acids in relation to the total number of amino acids. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, variant integrin proteins of the present invention may be shorter or longer than the amino acid sequence shown in FIG. 1F. Thus, in a preferred embodiment, included within the definition of integrin proteins (or variant integrin proteins) are portions or fragments of the sequences depicted herein. Fragments of integrin proteins are considered integrin proteins if a) they share at least one antigenic epitope; b) have at least the indicated homology; c) and preferably have integrin biological activity as defined herein.

In a preferred embodiment, as is more fully outlined below, the integrin proteins include further amino acid variations, as compared to a wild type integrin, than those outlined herein. In addition, as outlined herein, any of the variations depicted herein may be combined in any way to form additional novel integrin proteins.

In addition, variant integrin proteins can be made that are longer than those depicted in the figures, for example, by the addition of epitope or purification tags, as outlined herein, the addition of other fusion sequences, etc. For example, the variant integrin proteins of the invention may be fused to other therapeutic proteins such as IL-11 or to other proteins such as Fc or serum albumin for pharmacokinetic purposes. See for example U.S. Pat. Nos. 5,766,883 and 5,876,969, both of which are expressly incorporated by reference.

In a preferred emodiment, the variant integrins serve as modulators of wild-type integrins. Modulators in this context include both antagonists and agonists, with the former being preferred.

Thus, in a preferred embodiment, the variant integrins of the invention are antagonists of wild-type integrins. By "antagonists of wild-type integrin" herein is meant that the variant integrin protein inhibits or significantly decreases the activation of receptor signaling by wild-type integrin proteins. In a preferred embodiment, the variant integrin protein interacts with the wild-type integrin protein such that the complex comprising the variant integrin and wild-type integrin is incapable of binding to another molecule and/or participate in signal transduction. Preferably, the variant integrin protein preferentially interacts with wild-type integrins to form mixed hetroduplexes, i.e., mixed alpha and beta subunits, with the wild-type protein such that binding does not occur and/or integrin signaling is not initiated.

In an alternate embodiment, the variant integrins of the invention are agonists of wild-type integrins. By "agonists of wild-type integrin" herein is meant that the variant integrin protein promotes or significantly increases the activation of receptor signaling by wild-type integrin proteins. In a preferred embodiment, the variant integrin protein interacts with the wild-type integrin protein such that the complex comprising the variant integrin and wild-type integrin is more capable of binding to another molecule and/or participate in signal transduction. Preferably, the variant integrin protein preferentially interacts with wild-type integrins to form mixed hetroduplexes, i.e., mixed alpha and beta subunits, with the wild-type protein such that binding is more likely to occur and/or integrin signaling is more likely to occur upon binding.

In a preferred embodiment, the variant integrin protein is an integrin protein comprising a variant I domain. In this embodiment, the I domain can be added, in an active form, and will compete against the native I domains in whichever system they are introduced into. These open I domains will have the advantage of binding better than the wild type I domains in the native integrin, but these I domains need not be incorporated into the membrane (although they may be as explained in example 2). This will have an end result of functionally lowering the concentration of native I domains (i.e. integrins or other proteins with similar I domains) that can be activated because the ligand will be bound to the structurally biased I domain.

By "active" or "open" conformation, state, structure or equivalent grammatical term, herein is meant the three dimensional shape of the integrin protein, which allows the protein to bind to its target. As will be appreciated by those in the art, "activity" need not be an all or none description, active is defined in relative terms, often depending on the presence of other factors in the system. In this system the level of activity of an active integrin has been well defined by the prior art, as well as has been the level of activity of an inactive (closed) integrin. For the purposes of this invention, the importance of activity is in terms of identical environmental conditions between the wild-type integrin and the variant integrin. An example of this difference is presented in Shimaoka et al., (Nature Struct Biol. 7:674–678 (2000)). As pictured at the individual molecule level, the protein that is in an open or active conformation will readily react with a target ligand (Ab etc.) while the protein in a closed or inactive conformation may also interact with a target ligand—but at a lower probability of an actual binding event occurring. For examples of sequences and possible conformations that are defined as but do not limit the open or active conformation of integrin see Shimaoka et al., (Nature Struct Biol. 7:674–678 (2000)); Lee et al., (Cell 80: 631–638 (1995), and Structure 15: 1333–1340 (1995))

By "active" or "open" herein is meant that the protein is able to perform any of its recognized "integrin" functions (for a review see Humphries, 2000; Yamada and Miyamoto, Curr. Opin. Cell Biol. 7:681–689; 1995; Brakebusch et al, J. Cell Sci. 110:2895–2904 (1997); Hynes and Bader, Thromb. Haemostasis 78:83–87 (1997); Shattil et al, Blood 91:2645–2657(1998); Aplin et al, Pharmacol. Rev. 50:197–263 (1998); Giancotti and Ruoslahti, Science 285:1028–1032 (1999); Schwatz and Baron, Curr. Opinion Cell Biol. 11:197–202(1999)). These functions include, but are not limited to, maintenance of tissue integrity, cellular migration, physical support for cells allowing cohesion, traction forces for movement and to organize signaling complexes for cell fate and cell differentiation. Integrin functions are generally recognized to be mediated by the binding of various forms of ligands to the open conformation of integrin. These ligands include but are not limited to: collagen as a broad class, ICAM-1, iC3b, Factor X, and fibrinogen.

As will be recognized by those skilled in the art from the results in Shimaoka et al., (Nature Struct Biol. 7:674–678 (2000)) the active conformation of the I domain in an integrin forces the rest of the integrin protein into the active state. As such, a variant I domain from the current invention is equivalent to an alpha subunit with a variant I domain from the current invention or to a complete variant integrin subunit (alpha and beta) with a variant I domain from the current invention. However, as will be recognized by those skilled in the art, there may be unique advantages gained by incorporating the entire integrin protein or subunit instead of simply the modified I domain. For example, an increased number of possible epitopes may be had by increasing the amount of protein in the sample, or additional changes between the various states of the molecule may be determined.

By "closed" or "inactive" herein is meant the opposite of open or active. As will be recognized by those in the field, a closed state may still show binding or activity, the critical point is that the binding is less than the open state. In a preferred embodiment, binding of closed variant integrin protein will be approximately equal to or less than that of the wild-type integrin protein in its closed state. Additionally, as will be recognized by those skilled in the art, if signal transduction is required in the integrin molecule (i.e. across the membrane) biasing the variant integrin protein so as to prevent such signal transduction will also "close" or "inactivate" the protein, despite binding.

By "structurally biased", "biased conformational state", "biased", or equivalent term, herein is meant that the new protein's conformation is stabilized in a manner that is different from wild-type protein. In the simplest terms this may be viewed as an increase in the amount of time that the protein's shape is in one particular functional conformation. As will be recognized in the field, the protein is practically never a static entity, as such the "one shape" is a functional definition defined by those functional elements of the protein. By functional elements, herein is meant those chemical entities whose characteristics are important to allow the desired reaction to occur. Since proteins are never truly motionless, stabilization may also be defined in terms of restricting the possible conformations that the wild-type integrin could exist in to fewer in number, or fewer in functional number. Additionally, stabilization may also have a post-ligand binding element, that is the duration of ligand binding may be increased, or the ability of the ligand to leave may be decreased, either view will result in an increased biased conformational state. Additionally, as those skilled in the art will realize, if ligand binding induces a more stabilized state, obtaining a functionally biased conformational state in a protein with ligand, may be achieved by a protein structure which has accelerated conformational changes occurring in the protein.

As is recognized by those skilled in the art, more than the three dimensional state of the protein may be stabilized or biased. Other features which may be stabilized include but are not limited to van der waals interactions hydrophobicity, hydrogen bonds, electrostatics-either charge-charge interaction (either inter or intra protein) or charge-field interactions (either electric or magnetic field) and tunneling of electrons.

Additionally, stabilization may be described by, but not limited by, terms of energetics as is common in the field of protein chemistry. For example as outlined in Shimaoka et al., (Nature Struct Biol. 7:674–678 (2000)), the structurally biased open mutants are lower in energy in the open conformation (and thus more stable) than the wild-type integrin is, while in the closed conformation the structurally biased open integrin is higher in energy than is the wild-type protein. Conversely, the structurally biased closed mutant is higher in energy than the wild-type integrin is in the open confirmation, while it is lower in energy than the wild-type integrin is in the closed state (and thus it is stabilized in the closed state).

As will be recognized by those skilled in the art, there can be a functional difference between "binding" and "binding and signaling." For those integrins or I domains that function by binding to another molecule to allow, for example, stability or traction, binding is the sum total of such a protein's actions. However, if ligand binding to the integrin or I domain is then followed by additional conformational rearrangements, acceleration of binding of a ligand may not be equivalent to acceleration of integrin signaling. However, as will be appreciated by those in the field, the same techniques used to derive the current structures would also apply to determining an optimized structure for acceleration of both binding and signaling. Additionally, as will be appreciated by those skilled in the art, since binding is often the rate limiting step for most reactions in protein science, acceleration of binding will result in a dramatic acceleration of the signaling event as well. By signaling we mean the transduction of some event, not through the actual event itself (i.e. binding would be the event itself, phosphorylation of another protein would be a signal.)

In a preferred embodiment, the amino acid alterations (including substitutions, insertions and deletions) are noncontiguous. By noncontiguous herein is meant that the inserted mutations are not completely continuous along the peptide backbone. At least one amino acid must remain unchanged between two changed amino acids, however, not all changed amino acids need to be noncontiguous. Additionally, regions (areas of contiguous changed or mutated residues) that are noncontiguous are not doubly counted to be noncontiguous with each other if both positions have been already defined as noncontiguous with respect to the same third region. For instance, changing LVLVLVL (SEQ ID NO:8) to LPLPLVL (SEQ ID NO:9) would result in a single noncontiguous change of two amino acids, while LVLVLVL (SEQ ID NO:8) to LPLPLPL (SEQ ID NO: 10) would result in two noncontiguous changes (the left P and right P each being noncontiguous with the center P, while the left and right P are also noncontiguous with each other they have both already been counted in a noncontiguous sequence with respect to the center P.) Likewise, LVLVLVL (SEQ ID NO:8) to LPPPLVL (SEQ ID NO: 11) is a contiguous change and LVLVLVL (SEQ ID NO:8) to LPPVLPP (SEQ ID NO:12) is a single noncontiguous change. However, LVLVLVL (SEQ ID NO:8) to PPLPPVP (SEQ ID NO: 13) would be counted as two noncontiguous changes.

Thus, the variant integrins of the inventions are engineered to have altered properties. The term "altered property" or grammatical equivalent thereof in the context of a polypeptide, as used herein, refers to any characteristic or attribute of a variant integrin polypeptide that can be selected or detected and compared to the corresponding property of a naturally occurring integrin protein. These properties include, but are not limited to oxidative stability, prolonged shelf-life; thermal stability, alkaline stability, pH activity profile, resistance to proteolytic degradation, kinetic association ($K_{on}$) and dissociation ($K_{off}$) rate, protein folding, inducing an immune response, the ability to bind to an alpha or beta subunit of the integrin protein, the ability to be secreted, the ability to modulate potency, the ability to exist in either the open or closed states in a biased manner, and the ability to transduce signals across a membrane.

Unless otherwise specified, a substantial change in any of the above-listed properties, when comparing the property of a variant integrin polypeptide to the property of a naturally occurring integrin protein is preferably at least a 20%, more preferably, 50%, most preferably at least a 100% increase or decrease.

A change in oxidative stability is evidenced by at least about 20%, more preferably at least 50% increase of activity of a variant integrin protein when exposed to various oxidizing conditions as compared to that of integrin. Oxidative stability is measured by known procedures.

A change in alkaline stability is evidenced by at least about a 50% or greater increase or decrease (preferably increase) in the half life of the activity of a variant integrin protein when exposed to increasing or decreasing pH conditions as compared to that of integrin. Generally, alkaline stability is measured by known procedures.

A change in thermal stability is evidenced by at least about a 50% or greater increase or decrease (preferably increase) in the half life of the activity of a variant integrin protein when exposed to a relatively high temperature and neutral pH as compared to that of integrin. Generally, thermal stability is measured by known procedures. In a preferred embodiment, a variant integrin protein of the invention has increase thermal stability when compared to the human integrin. Such a variant integrin protein preferably has an amino acid sequence which comprises substitution of one or more amino acid residues when compared to the amino acid sequence of human integrin. In one aspect of this embodiment, the amino acid sequence of the variant integrin protein comprises 2, 3, 4, 5, 6, 7, 8, 9, 10, or more substitutions when compared to the amino acid sequence of human integrin.

Similarly, variant integrin proteins, for example are experimentally tested and validated in in vivo and in in vitro assays. Suitable assays include, but are not limited to, e.g., examining their binding affinity to natural occurring or variant ligands and to high affinity agonists and/or antagonists. In addition to cell-free biochemical affinity tests, quantitative comparison are made comparing kinetic and equilibrium binding constants for the ligands to the naturally occurring integrin and to the variant integrin proteins. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. Comparing the binding constant between a natural integrin and its corresponding naturally occurring target with the binding constant of a variant integrin protein made in order to evaluate the sensitivity and specificity of the integrin protein to its natural target molecule. (Preferably, binding affinity of the variant integrin protein to natural targets and agonists increases relative to the naturally occurring integrin, while antagonist affinity decreases. Variant integrin proteins with higher affinity to antagonists relative to the wild-type integrin may also be generated by the methods of the invention.

In one embodiment, variant integrin's binding in an iC3b cell binding assay will be at least that of a wild-type integrin. In a preferred embodiment, the increase in the variant integrin's binding in an iC3b binding assay will be 20% of the wild type integrin (as described in Shimaoka et al., (Nature Struct Biol. 7:674–678 (2000)). In a more preferred embodiment, the increase in binding will be at least, close to 50% of the wild type integrin. In the most preferred embodiment, the increase in binding (which can be determined either as done in example 1 or by use of a device similar to a BIAcore) of the variant integrin will be at least 70% of the wild type integrin.

In a preferred embodiment, the variant integrin's binding in an antibody binding assay will be at least 100% of the wild-type (as described in Shimaoka et al., (Nature Struct Biol. 7:674–678 (2000))). In a more preferred embodiment, binding will be at least, 200% of wild-type. In the most preferred embodiment, the binding of the variant integrin in an antibody assay will be at least 300% of wild-type integrin.

In an alternate embodiment of the invention, where the variant integrin is designed in a closed state, a decrease in binding affinity is desired.

In one embodiment, the closed variant integrin's binding in a iC3b assay (as shown by Shimaoka et al., (Nature Struct Biol. 7:674–678 (2000))) will be the same as wild-type. In a preferred embodiment the closed variant integrin's binding will be approximately half of wild-type integrin.

In one embodiment, the variant integrin's binding in an antibody binding assay will be substantially the same as wild-type integrin. In a preferred embodiment, the variant integrin's binding will be less than that of the wild-type integrin (when the antibody preferentially binds to the open state of the protein). Additionally, the desired closed state may express itself as resulting in a smaller percent decrease of cells bound to iC3b than wild type integrin, upon the addition of a blocking agent such as a blocking antibody. (Shimaoka et al., (Nature Struct Biol. 7:674–678 (2000)), and FIG. 3D).

In a preferred embodiment, the antigenic profile in the host animal of the variant integrin protein is similar, and preferably identical, to the antigenic profile of the host integrin; that is, the variant integrin protein does not significantly stimulate the host organism (e.g. the patient) to an immune response; that is, any immune response is not clinically relevant and there is no allergic response or neutralization of the protein by an antibody. That is, in a preferred embodiment, the variant integrin protein does not contain additional or different epitopes from the integrin. By "epitope" or "determinant" herein is meant a portion of a protein which will generate and/or bind an antibody. Thus, in most instances, no significant amount of antibodies are generated to a variant integrin protein. In general, this is accomplished by not significantly altering surface residues, as outlined below nor by adding any amino acid residues on the surface which can become glycosylated, as novel glycosylation can result in an immune response.

In a preferred embodiment the variant integrin proteins of the invention will have a sequence that differs from a wild-type human Integrin protein in at least three amino acid position selected from any of the positions in table 1.

In a preferred embodiment the variant integrin protein of the invention will have a sequence with at least two point mutations at either: 156, 160, 199, 215, 238, 239, 240, 259, 269, 271, 287, 299, 308.

In a preferred embodiment the open variant integrin protein of the invention will have a sequence with at least two point mutations at either: 156, 199, 215, 238, 239, 240, 259, 287, 299.

In a preferred embodiment the open variant integrin protein of the invention will have a sequence with at least two point mutations at either: 139, 153, 157, 199, 238, 239, 287, 299.

In a preferred embodiment the closed variant integrin protein of the invention will have a sequence with at least two point mutations at either: 215, 219, 223, 238.

In a more preferred embodiment, the actual amino acid characteristics of each of the above possible positional mutants is defined in table 1 (SEQ ID NOS:3–6).

In a preferred embodiment, variant integrin proteins (or variant I domains) have variable positions selected solely from core residues of human integrin. Alternatively, at least a majority (51%) of the variable positions are selected from core residues, with at least about 75% of the variable positions being preferably selected from core residue positions, and at least about 90% of the variable positions being particularly preferred. A specifically preferred embodiment has only core variable positions altered as compared to human integrin.

In a preferred embodiment, the variant integrin proteins of the invention are human integrin conformers. By "conformer" herein is meant a protein that has a protein backbone 3D structure that is virtually the same but has significant differences in the amino acid side chains. That is, the variant integrin proteins of the invention define a conformer set, wherein all of the proteins of the set share a backbone structure and yet have sequences that differ by at least 3–5%. The three dimensional backbone structure of an variant integrin protein thus substantially corresponds to the three dimensional backbone structure of human integrin "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the human integrin structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer by examining the energy of the sequence.

Variant integrin proteins may also be identified as being encoded by variant integrin nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, an variant integrin nucleic acid encodes a variant integrin protein. As will be appreciated by those in the art, due to the degeneracy of the genetic code, an extremely large number of nucleic acids may be made, all of which encode the variant integrin proteins of the present invention. Thus, having identified a particular amino acid sequence, those skilled in the art could make any number of different nucleic acids, by simply modifying the sequence of one or more codons in a way which does not change the amino acid sequence of the variant integrin protein.

In one embodiment, the nucleic acid homology is determined through hybridization studies. Thus, for example, a nucleic acid, which hybridizes under high stringency to a nucleic acid sequence encoding integrin (e.g. see GenBank accession numbers J03925, X07640) and encode an integrin protein is considered an integrin gene.

High stringency conditions are known in the art; see for example Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Sambrook et al., supra; Ausubel et al., supra, and Tijssen, supra.

The variant integrin proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated variant integrin nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an variant integrin protein from one organism in a different organism or host cell. Alternatively, the protein may be made at a significantly higher concentration than is normally seen, through the use of an inducible promoter or high expression promoter, such that the protein is made at increased concentration levels. Furthermore, all of the variant integrin proteins outlined herein are in a form not normally found in nature, as they contain amino acid substitutions, insertions and deletions, with substitutions being preferred, as discussed below.

Also included within the definition of variant integrin proteins of the present invention are amino acid sequence variants of the integrin protein sequences outlined herein and shown in the Table 1. That is, the variant integrin proteins may contain additional variable positions as compared to human integrin. These variants fall into one or more of three classes: substitutional, insertional or deletional variants. These variants ordinarily are prepared by site specific mutagenesis of nucleotides in the DNA encoding an integrin protein, using cassette or PCR mutagenesis or other techniques well known in the art, to produce DNA encoding the variant, and thereafter expressing the DNA in recombinant cell culture as outlined above. However, variant integrin protein fragments having up to about 100–150 residues may be prepared by in vitro synthesis using established techniques. Specifically, variant integrin proteins comprising only amino acid sequences for the variant I domain may be prepared by in vitro synthesis.

While the site or region for introducing an amino acid sequence variation is predetermined, the mutation per se need not be predetermined. For example, in order to optimize the performance of a mutation at a given site, random mutagenesis may be conducted at the target codon or region and the expressed integrin variants screened for the optimal combination of desired activity. Techniques for making substitution mutations at predetermined sites in DNA having a known sequence are well known, for example, M13 primer mutagenesis and PCR mutagenesis. Screening of the mutants is done using assays of integrin protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the variant integrin protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original integrin protein, although variants also are selected to modify the characteristics of the integrin proteins as needed. Alternatively, the variant may be designed such that the biological activity of the integrin protein is altered. For example, glycosylation sites may be altered or removed. Similarly, the biological function may be altered; for example, in some instances it may be desirable to have more or less potent variant integrin activity.

The variant integrin proteins and nucleic acids of the invention can be made in a number of ways. Individual nucleic acids and proteins can be made as known in the art and outlined below. Alternatively, libraries of variant integrin proteins can be made for testing.

In a preferred embodiment, the variant integrin library is generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the variant integrin library. That is, as above, these variable positions are collected and all possible combinations are generated, but the amino acid residues that "fill" the variant integrin library are utilized on a frequency basis. Thus, in a non-frequency based variant integrin library, a variable position that has 5 possible residues will have 20% of the proteins comprising that variable position with the first possible residue, 20% with the second, etc. However, in a frequency based variant integrin library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create variant integrin libraries as described herein. SCMF can be used in three ways: the frequencies of amino acids and rotamers for each amino acid are listed at each position; the probabilities are determined directly from SCMF (see Delarue et la. Pac. Symp. Biocomput. 109–21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53–70 (1995); all of which are expressly incorporated by reference. Similar methods include, but are not limited to, OPLS-AA (Jorgensen, et al., J. Am. Chem. Soc. (1996), v 118, pp 11225–11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697–1714; Liwo, et al., Protein (1993), v 2, pp1715–1731; Liwo, et al., J. Comp. Chem. (1997), v 18, pp849–873; Liwo et al., J. Comp. Chem. (1997), v 18, pp874–884; Liwo, et al., J. Comp. Chem. (1998), v 19, pp259–276; Forcefield for Protein Structure Prediction (Liwo, et al., Proc. Natl. Acad. Sci. USA (1999), v 96, pp5482–5485); ECEPP/3 (Liwo et al., J Protein Chem 1994 May;13(4):375–80); AMBER 1.1 force field (Weiner, et al., J. Am. Chem. Soc. v106, pp765–784); AMBER 3.0 force field (U. C. Singh et al., Proc. Natl. Acad. Sci. USA. 82:755–759); CHARMM and CHARMM22 (Brooks, et al., J. Comp. Chem. v4, pp 187–217); cvff3.0 (Dauber-Osguthorpe, et al.,(1988) Proteins: Structure, Function and Genetics, v4, pp31–47); cff91 (Maple, et al., J. Comp. Chem. v15, 162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can add amino acids found in the alignment of homologous sequences to the result of the computation. Preferable one can add the wild type amino acid identity to the probability table if it is not found in the computation.

As will be appreciated, a variant integrin library created by recombining variable positions and/or residues at the variable position may not be in a rank-ordered list. In some embodiments, the entire list may just be made and tested. Alternatively, in a preferred embodiment, the variant integrin library is also in the form of a rank ordered list. This may be done for several reasons, including the size of the variant integrin library is still too big to generate experimentally, or for predictive purposes. This may be done in several ways. In one embodiment, the variant integrin library is ranked using the scoring functions of PDA to rank the library members. Alternatively, statistical methods could be used. For example, the variant integrin library may be ranked by frequency score; that is, proteins containing the most of high frequency residues could be ranked higher, etc. This may be done by adding or multiplying the frequency at each variable position to generate a numerical score. Similarly, the variant integrin library different positions could be weighted and then the proteins scored; for example, those containing certain residues could be arbitrarily ranked.

In a preferred embodiment, the different protein members of the variant integrin library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the variant integrin library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 5. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the variant integrin library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutaions in the desired proportions.

The total number of oligonucleotides needed is a function of the number of positions being mutated and the number of mutations being considered at these positions:
(number of oligos for constant positions)+M1+M2+M3+ . . . Mn=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonuclotide primer, the clusters can be set to the "good" correlations, and eliminate the bad combinations that may decrease the effectiveness of the library. However, if the residues of the cluster are far apart in sequence, and thus will reside on different oligonuclotides for synthesis, it may be desirable to either set the residues to the "good" correlation, or eliminate them as variable residues entirely. In an alternative embodiment, the library may be generated in several steps, so that the cluster mutations only appear together. This procedure, i.e., the procedure of identifying mutation clusters and either placing them on the same oligonucleotides oreliminating them from the library or library generation in several steps preserving clusters, can considerably enrich the experimental library with properly folded protein. Identification of clusters can be carried out by a number of wasy, e.g. by using known pattern recognition methods, comparisons of frequencies of occurrence of mutations or by using energy analysis of the sequences to be experimentally generated (for example, if the energy of interaction is high, the positions are correlated). these correlations may be positional correlations (e.g. variable positions 1 and 2 always change together or never change together) or sequence correlations (e.g. if there is a residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford Unviersity, 1999; Andrews, Harry C. Introduction to mathematical techniques in patter recognition; New York, Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with Neural networks in C++/Abhijit S. Pandya, Robert B. Macy. Boca Raton, Fla.: CRC Press, 1996; Handbook of pattern recognition and computer vision/edited by C. H. Chen, L. F. Pau, P. S. P. Wang. $2^{nd}$ ed. Signapore; River Edge, N.J.: World Scientific, c1999; Friedman, Introduction to Pattern Recognition: Statistical, Structural, Neural, and Fuzzy Logic Approaches; River Edge, N.J.: World Scientific, c1999, Series title: Serien a machine perception and artificial intelligence; vol. 32; all of which are expressly incorporated by reference. In addition programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotides start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in variant integrin libraries defining different length proteins, which can be expressed by a library of pooled oligonucleotide of different lengths.

In a preferred embodiment, the variant integrin library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences can also be an artificial set; for example, from a probability table (for example generated using SCMF) or a Monte Carlo set. Similarly, the "family" can be the top 10 and the bottom 10 sequences, the top 100 sequence, etc. This may also be done using error-prone PCR.

Thus, in a preferred embodiment, in silico shuffling is done using the computational methods described therein. That is, starting with either two libraries or two sequences, random recombinations of the sequences can be generated and evaluated.

In a preferred embodiment, error-prone PCR is done to generate the variant integrin library. See U.S. Pat. Nos. 5,605,793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleotides that code for the mutations at the variant positions of the variant integrin library (bias oligonucleotides). The addition of the oligonucleotides will create a bias favoring the incorporation of the mutations in the variant integrin library. Alternatively, only oligonucleotides for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the variant integrin library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the variant integrin library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild type gene or other gene can be used, as is schematically depicted in FIG. 5. In this embodiment, a starting gene is used; generally, although this is not required, the gene is the wild type gene. In some cases it may be the gene encoding the global optimized sequence, or any other sequence of the list. In this embodiment, oligonucleotides are used that correspond to the variant positions and contain the different amino acids of the variant integrin library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In addition, there are several other techniques that can be used, as exemplified in the figures, e.g. FIGS. 7–9. In a preferred embodiment, ligation of PCR products is done.

In a preferred embodiment, a variety of additional steps may be done to one or more variant integrin libraries; for example, further computational processing can occur, variant integrin libraries can be recombined, or cutoffs from different variant integrin libraries can be combined. In a preferred embodiment, a variant integrin library may be computationally remanipulated to form an additional variant integrin library (sometimes referred to herein as "tertiary libraries"). For example, any of the variant integrin library sequences may be chosen for a second round of PDA, by freezing or fixing some or all of the changed positions in the first variant integrin library. Alternatively, only changes seen in the last probability distribution table are allowed. Alternatively, the stringency of the probability table may be altered, either by increasing or decreasing the cutoff for inclusion. Similarly, the variant integrin library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining different variant integrin libraries. For example, a probability distribution table from a first variant integrin library can be generated and recombined, either computationally or experimentally, as outlined herein. A PDA variant integrin library may be combined with a sequence alignment variant integrin library, and either recombined (again, computationally or experimentally) or just the cutoffs from each joined to make a new tertiary library. The top sequences from several libraries can be recombined. Sequences from the top of a library can be combined with sequences from the bottom of the library to more broadly sample sequence space, or only sequences distant from the top of the library can be combined. Variant integrin libraries that analyzed different parts of a protein can be combined to a tertiary library that treats the combined parts of the protein.

In a preferred embodiment, a tertiary library can be generated using correlations in the variant integrin library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode a variant integrin protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant integrin protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant integrin protein, a replacement of the naturally occurring secretory leader sequence is desired. In this embodiment, an unrelated secretory leader sequence is operably linked to a variant integrin encoding nucleic acid leading to increased protein secretion. Thus, any secretory leader sequence resulting in enhanced secretion of the variant integrin protein, when compared to the secretion of integrin and its secretory sequence, is desired. Suitable secretory leader sequences that lead to the secretion of a protein are know in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding a variant integrin protein. As will be appreciated by those in the art, all combinations are possible and accordingly, as used herein, the combination of components, comprised by one or more vectors, which may be retroviral or not, is referred to herein as a "vector composition".

The variant integrin nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The variant integrin nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The variant integrin proteins of the present invention are produced by culturing a host cell transformed with an expression vector containing nucleic acid encoding a variant integrin protein, under the appropriate conditions to induce or cause expression of the variant integrin protein. The conditions appropriate for variant integrin protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, *Neurospora*, BHK, CHO, COS, *Pichia Pastoris*, etc.

In a preferred embodiment, the variant integrin proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the variant integrin nucleic acid.

In a preferred embodiment, the variant integrin proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the variant integrin protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the variant integrin protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a variant integrin encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, variant integrin proteins are produced in insect cells. Expression vectors for the transformation of insect cells, and in particular, baculovirus-based expression vectors, are well known in the art.

In a preferred embodiment, variant integrin protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the variant integrin polypeptides of the invention may be further fused to other proteins, if desired, for example to increase expression or stabilize the protein.

In one embodiment, the variant integrin nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Additionally, modified amino acids or chemical derivatives of amino acids of consensus or fragments of integrin proteins, according to the present invention may be provided, which polypeptides contain additional chemical moieties or modified amino acids not normally a part of the protein. Covalent and non-covalent modifications of the protein are thus included within the scope of the present invention. Such modifications may be introduced into an integrin polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)alanine, (phosphono)glycine, (phosphono)leucine, (phosphono)isoleucine, (phosphono)threonine, or (phosphono)serine; or sulfated (e.g., —SO$_3$H) threonine, serine, tyrosine.

Other substitutions may include unnatural hyroxylated amino acids that may be made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Preferred alkyl groups herein contain 1 to 12 carbons atoms. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, and nitrogen being preferred. Alkyl includes substituted alkyl groups. By "substituted alkyl group" herein is meant an alkyl group further comprising one or more substitution moieties. A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant integrin polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant integrin polypeptides of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Once made, the variant integrin proteins may be covalently modified. Covalent and non-covalent modifications of the protein are thus included within the scope of the present invention. Such modifications may be introduced into a variant integrin polypeptide by reacting targeted amino acid residues of the polypeptide with an organic derivatizing agent that is capable of reacting with selected side chains or terminal residues.

One type of covalent modification includes reacting targeted amino acid residues of a variant integrin polypeptide with an organic derivatizing agent that is capable of reacting with selected side chains or the N-or C-terminal residues of a variant integrin polypeptide. Derivatization with bifunctional agents is useful, for instance, for crosslinking a variant integrin protein to a water-insoluble support matrix or surface for use in the method for purifying anti-variant integrin antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the variant integrin polypeptide included within the scope of this invention comprises altering the native glycosylation pattern of the polypeptide. "Altering the native glycosylation pattern" is intended for purposes herein to mean deleting one or more carbohydrate moieties found in native sequence variant integrin polypeptide, and/or adding one or more glycosylation sites that are not present in the native sequence variant integrin polypeptide.

Addition of glycosylation sites to variant integrin polypeptides may be accomplished by altering the amino acid sequence thereof. The alteration may be made, for example, by the addition of, or substitution by, one or more serine or threonine residues to the native sequence variant integrin polypeptide (for O-linked glycosylation sites). The variant integrin amino acid sequence may optionally be altered through changes at the DNA level, particularly by mutating the DNA encoding the variant integrin polypeptide at preselected bases such that codons are generated that will translate into the desired amino acids.

Another means of increasing the number of carbohydrate moieties on the variant integrin polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the variant integrin polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, permeability across the blood brain barrier biological half life, and the like. Such moieties or modifications of variant integrin polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of variant integrin comprises linking the variant integrin polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Variant integrin polypeptides of the present invention may also be modified in a way to form chimeric molecules comprising a variant integrin polypeptide fused to another, heterologous polypeptide or amino acid sequence. In one embodiment, such a chimeric molecule comprises a fusion of a variant integrin polypeptide with a tag polypeptide which provides an epitope to which an anti-tag antibody can selectively bind. The epitope tag is generally placed at the amino-or carboxyl-terminus of the variant integrin polypeptide. The presence of such epitope-tagged forms of a variant integrin polypeptide can be detected using an antibody against the tag polypeptide. Also, provision of the epitope tag enables the variant integrin polypeptide to be readily purified by affinity purification using an anti-tag antibody or another type of affinity matrix that binds to the epitope tag. In an alternative embodiment, the chimeric molecule may comprise a fusion of a variant integrin polypeptide with an immunoglobulin or a particular region of an immunoglobulin. For a bivalent form of the chimeric molecule, such a fusion could be to the Fc region of an IgG molecule.

The library protein may also be made as a fusion protein, using techniques well known in the art. Thus, for example, for the creation of monoclonal antibodies, if the desired epitope is small, the library protein may be fused to a carrier protein to form an immunogen. Alternatively, the library protein may be made as a fusion protein to increase expression, or for other reasons. For example, when the library protein is an library peptide, the nucleic acid encoding the peptide may be linked to other nucleic acid for expression purposes. Similarly, other fusion partners may be used, such as targeting sequences which allow the localization of the library members into a subcellular or extracellular compartment of the cell, rescue sequences or purification tags which allow the purification or isolation of either the library protein or the nucleic acids encoding them; stability sequences, which confer stability or protection from degradation to the library protein or the nucleic acid encoding it, for example resistance to proteolytic degradation, or combinations of these, as well as linker sequences as needed.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the library member comprises a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the library member or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_nGGPP$ (SEQ ID NO:7), where X is any amino acid and n is an integer of least four.

In one embodiment, the library nucleic acids, proteins and antibodies of the invention are labeled. By "labeled" herein is meant that nucleic acids, proteins and antibodies of the invention have at least one element, isotope or chemical compound attached to enable the detection of nucleic acids, proteins and antibodies of the invention. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology 6:1204–1210 (1988)]; the KT3 epitope peptide [Martin et al., Science 255:192–194 (1992)]; tubulin epitope peptide [Skinner et al., J. Biol. Chem. 266:15163–15166 (1991)]; and the T7 gene 10 protein peptide tag [Lutz-Freyermuth et al., Proc. Natl. Acad. Sci. U.S.A. 87:6393–6397 (1990)].

In a preferred embodiment, the variant integrin protein is purified or isolated after expression. Variant integrin proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the variant integrin protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the variant integrin protein. In some instances no purification will be necessary.

Once made, the variant integrin proteins and nucleic acids of the invention find use in a number of applications. In one embodiment, the variant integrin proteins (or simply the variant I domains themselves, regardless of whether they are related to integrin) are administered to a patient to treat an integrin-associated disorder.

It should be noted that therapeutic proteins utilized in these methods will preferentially have residues in the hydrophobic cores screened, to prevent changes in the molecular surface of the protein that might induce immunogenic responses. Therapeutic proteins can also be designed in the region surrounding their binding sites to their receptors. Such a region can be defined, for example, by including in the design all residues within a certain distance, for example 4.5 Å of the binding site residues. This range can vary from 4 to 6–10 Å. This design will serve to improve activity and specificity.

By "integrin related disorder" or "integrin responsive disorder" or "condition" herein is meant a disorder that can be ameliorated by the administration of a pharmaceutical composition comprising a variant integrin protein, including, but not limited to, inflammatory and immunological disorders. In a preferred embodiment, the variant integrin protein is used to treat rheumatoid arthritis.

In a preferred embodiment, a therapeutically effective dose of a variant integrin protein (or simply the I domain) is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 5 μg/kg are used, administered either intraveneously or subcutaneously. As is known in the art, adjustments for variant integrin protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, in the case of an autoimmune disease successful administration of a variant integrin protein prior to the onset of the disease results in "treatment" of the disease. As another example, successful administration of an variant integrin protein after clinical manifestation of the disease to combat the symptoms of the disease comprises "treatment" of the disease. "Treatment" also encompasses administration of a variant protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

In another embodiment, a therapeutically effective dose of a variant integrin protein, a variant integrin gene, or a variant integrin antibody is administered to a patient having a disease involving inappropriate expression of integrin. A "disease involving inappropriate expression of at integrin" within the scope of the present invention is meant to include diseases or disorders characterized by aberrant integrin, either by alterations in the amount of integrin present or due to the presence of mutant integrin. An overabundance may be due to any cause, including, but not limited to, overexpression at the molecular level, prolonged or accumulated appearance at the site of action, or increased activity of integrin relative to normal. Included within this definition are diseases or disorders characterized by a reduction of integrin. This reduction may be due to any cause, including, but not limited to, reduced expression at the molecular level, shortened or reduced appearance at the site of action, mutant forms of integrin, or decreased activity of integrin relative to normal. Such an overabundance or reduction of integrin can be measured relative to normal expression, appearance, or activity of integrin according to, but not limited to, the assays described and referenced herein.

The administration of the variant integrin proteins of the present invention, preferably in the form of a sterile aqueous solution, can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the variant integrin protein may be directly applied as a solution or spray. Depending upon the manner of introduction, the pharmaceutical composition may be formulated in a variety of ways. The concentration of the therapeutically active variant integrin protein in the formulation may vary from about 0.1 to 100 weight %. In another preferred embodiment, the concentration of the variant integrin protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant integrin protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the variant integrin proteins are added in a micellular formulation; see U.S. Pat. No. 5,833, 948, hereby expressly incorporated by reference in its entirety.

Combinations of pharmaceutical compositions may be administered. Moreover, the compositions may be administered in combination with other therapeutics.

In one embodiment provided herein, antibodies, either polyclonal or monoconal can be raised against either of the biased state variant integrins by procedures which are common in the field and then the resulting antibodies can be screened by a variety of methods, some of which are outlined below for general screening of bioactive molecules against variant integrins. As those skilled in the art realize the advantages of such antibodies go beyond the previously mentioned uses. Antibodies which can differentiate between the biased open and biased closed variant integrins will allow different treatments to different areas.

Treatments include the below defined antibody localized medicine. Treatments may also involve the visualization of active and inactive (open and closed respectively) populations of integrin proteins. Such information may be useful both as to the immediate health of the cell and of the cells environment.

As will be realized by those in the art, antibodies to a biased conformation may bind selectively because they bind to the active site of the molecule. The active site is defined as a three dimensional space where the ligand can directly contact the integrin. Since the antibody may directly contact or cover this active site, the antibody itself may prevent binding of the ligand to the integrin, allowing the antibody to act as a bioactive molecule. Uses for such an antibody would be similar to uses for the bioactive molecules.

Additionally, as those skilled in the art will appreciate, since integrin is dependent upon certain metal ions, and the binding of such metal ions effects the state of the integrin protein, conformationally biased molecules may also enable antibodies to be differentiated on the basis of the presence or absence of a metal ion in the molecule's MIDAS because the activated variant integrin will retain the structure of the metal bound integrin more readily than the wild-type integrin.

Additionally, as those skilled in the art will realize, the conformationally biased variant integrin proteins will enable the design of antibodies similar to catalytic antibodies, which in turn can be used to bias the state/conformation of the wild-type integrin proteins to mimic the original state of the designed conformationally biased (variant) integrin. By "catalytic antibodies", herein is meant that an antibody which binds to a molecule's intermediate conformation (as used in the field of enzymatics to denote the conformational state associated with the highest energy portion of a molecule's free energy plot). The effect of the catalytic antibody binding is to promote more of the open (or closed) integrin protein.

As will be appreciated by those in the field, the antibody may stabilize the protein by binding to the open conformation and either stabilizing this state or preventing dissociation of the bound ligand. Since the variant integrin proteins are designed to be biased in the open conformation, finding antibodies which bind well with the open state and not to the biased closed (variant) integrin proteins will direct efforts to find antibodies which stabilize the open state. Likewise, it is possible to stabilize the closed state of the integrin protein to find antibodies which do the opposite.

As will be appreciated by those in the art, the antibody itself need not be directed solely to the activated I domain of the variant integrin protein, and may be targeted to any part of the alpha subunit, or the alpha-beta dimer, so long as a biased I domain is part of the molecule. Additionally, antibodies may be targeted to the intracellular section of the activated variant integrin domain. In a preferred embodiment, these anti-variant integrin antibodies are used for immunotherapy. Thus, methods of immunotherapy are provided. By "immunotherapy" is meant treatment of an integrin related disorders with an antibody raised against a variant integrin protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant integrin protein antigen to which antibodies are raised. As appreciated by one of ordinary skill in the art, the variant integrin protein antigen may be provided by injecting a variant integrin polypeptide against which antibodies are desired to be raised into a recipient, or contacting the recipient with a variant integrin protein encoding nucleic acid, capable of expressing the variant integrin protein antigen, under conditions for expression of the variant integrin protein antigen.

In another preferred embodiment, a therapeutic compound is conjugated to an antibody, preferably an anti-variant integrin protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant integrin protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

Additionally, the antibodies may preferentially bind to "open" variants and not to the closed variant integrin or vice versa. Such differentiated antibodies can be produced by screening antibodies that bind to an activated variant integrin (or variant I domain) against the closed or inactivated biased (variant) integrin, those which bind in the first scenario, but not to the closed state are differentiated antibodies. Such discrimination will not only allow identification of areas of high or low integrin activity, but allow localization by the above described ways to localize the curative effects of the drugs associated with the toxins to be determined by activity of the integrin proteins themselves.

Additionally, as those skilled in the art will realize, by attaching molecules that are only toxic in combination, either through a combined unique effect or a concentration effect, cell death will only occur in those cells with large amounts of open (active) integrin where large amounts of the antibody can bind. As those in the art will appreciate, this could be applied to for integrin populations that are biased in the closed state.

One skilled in the art will realize that the antibodies may be raised against the biased open variant integrin I domain; the variant integrin protein with the biased open variant integrin I domain; or the entire variant integrin, including but not limited to the beta subunit, with the biased open variant integrin I domain. As demonstrated in this patent and as appreciated by those skilled in the art, the effects of biasing the I domain to one state is translated across the entire protein.

In a preferred embodiment, variant integrin proteins are administered as therapeutic agents, and can be formulated as outlined above. Similarly, variant integrin genes (including both the full-length sequence, partial sequences, or regulatory sequences of the variant integrin coding regions) can be administered in gene therapy applications, as is known in the art. These variant integrin genes can include antisense applications, either as gene therapy (i.e. for incorporation into the genome) or as antisense compositions, as will be appreciated by those in the art.

In a preferred embodiment, the nucleic acid encoding the variant integrin proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143–4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

In a preferred embodiment, variant integrin genes are administered as DNA vaccines, either single genes or combinations of variant integrin genes. Naked DNA vaccines are generally known in the art. Brower, Nature Biotechnology, 16:1304–1305 (1998). Methods for the use of genes as DNA vaccines are well known to one of ordinary skill in the art, and include placing a variant integrin gene or portion of a variant integrin gene under the control of a promoter for expression in a patient in need of treatment. The variant integrin gene used for DNA vaccines can encode full-length variant integrin proteins, but more preferably encodes portions of the variant integrin proteins including peptides derived from the variant integrin protein. In a preferred embodiment a patient is immunized with a DNA vaccine comprising a plurality of nucleotide sequences derived from a variant integrin gene. Similarly, it is possible to immunize a patient with a plurality of variant integrin genes or portions thereof as defined herein. Without being bound by theory, expression of the polypeptide encoded by the DNA vaccine, cytotoxic T-cells, helper T-cells and antibodies are induced which recognize and destroy or eliminate cells expressing integrin proteins.

In a preferred embodiment, the DNA vaccines include a gene encoding an adjuvant molecule with the DNA vaccine. Such adjuvant molecules include cytokines that increase the immunogenic response to the variant integrin polypeptide encoded by the DNA vaccine. Additional or alternative adjuvants are known to those of ordinary skill in the art and find use in the invention.

In a preferred embodiment, the library member is used to identify target molecules, i.e. the molecules with which the member interacts. As will be appreciated by those in the art, there may be primary target molecules, to which the library member binds or acts upon directly, and there may be secondary target molecules, which are part of the signalling pathway affected by the library member; these might be termed "validated targets".

In one embodiment, the biased variant integrin proteins or variant I domains are used to screen for bioactive agents as described below. If the libraries made consist only of the variant I domains, they may be converted/incorporated at any time into equivalent libraries of alpha subunits with the variant I domain or complete variant integrin proteins (alpha and beta subunits) with the variant I domain (although, as demonstrated in example 2) they need not be.) Additionally, as will be recognized in the art, these molecules may target either the extracellular or intracellular regions of the variant integrin protein.

In a preferred embodiment, the library may be put onto a chip or substrate as an array to make a "protein chip" or "biochip" to be used in high-throughput screening (HTS) techniques. Thus, the invention provides substrates with arrays comprising libraries (generally secondary or tertiary libraries" of proteins.)

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluorescese.

Generally the substrate is flat (planar), although as will be appreciated by those in the art, other configurations of substrates may be used as well; for example, three dimensional configurations can be used. Similarly, the arrays may be placed on the inside surface of a tube, for flow-through sample analysis to minimize sample volume.

By "array" herein is meant a plurality of library members in an array format; the size of the array will depend on the composition and end use of the array. Arrays containing from about 2 different library members to many thousands can be made. Generally, the array will comprise from $10^2$ to $10^8$ different proteins (all numbers are per square centimeter), with from about $10^3$ to about $10^6$ being preferred and from about $10^3$ to $10^5$ being particularly preferred. In addition, in some arrays, multiple substrates may be used, either of different or identical compositions. Thus for example, large arrays may comprise a plurality of smaller substrates.

As will be appreciated by those in the art, the library members may either be synthesized directly on the substrate, or they may be made and then attached after synthesis. In a preferred embodiment, linkers are used to attach the proteins to the substrate, to allow both good attachment, sufficient flexibility to allow good interaction with the target molecule, and to avoid undesirable binding reactions.

In a preferred embodiment, the library members are synthesized first, and then covalently or otherwise immobilized to the substrate. This may be done in a variety of ways, including known spotting techniques, ink jet techniques, etc.

In a preferred embodiment, the library may be put onto a chip or substrate as an array to make a "protein chip" or "biochip" to be used in high-throughput screening (HTS) techniques. Thus, the invention provides substrates with arrays comprising libraries (generally secondary or tertiary libraries) of proteins.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluorescese.

Generally the substrate is flat (planar), although as will be appreciated by those in the art, other configurations of substrates may be used as well; for example, three dimensional configurations can be used. Similarly, the arrays may be placed on the inside surface of a tube, for flow-through sample analysis to minimize sample volume.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occuring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As will be appreciated by those in the art, the proteinaceous library members may be attached to the substrate in a wide variety of ways. The functionalization of solid support surfaces such as certain polymers with chemically reactive groups such as thiols, amines, carboxyls, etc. is generally known in the art. Accordingly, substrates may be used that have surface chemistries that facilitate the attachment of the desired functionality by the user. Some examples of these surface chemistries include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different libraries to the substrates, generally using known chemistries. For example, libraries containing carbohydrates may be attached to an amino-functionalized support; the aldehyde of the carbohydrate is made using standard techniques, and then the aldehyde is reacted with an-amino group on the surface. In an alternative embodiment, a sulfhydryl linker may be used. There are a number of sulfhydryl reactive linkers known n the art such as SPDP, maleimides, a-haloacetyls, and pyridyl disulfides (see for example the 1994 Pierce Chemical Company catalog, technical section on cross-linkers, pages 155–200, incorporated herein by reference) which can be used to attach cysteine containing members to the support. Alternatively, an amino group on the library member may be used for attachment to an amino group on the surface. For example, a large number of stable bifunctional groups are well known in the art, including homobifunctional and heterobifunctional linkers (see Pierce Catalog and Handbook, pages 155–200). In an additional embodiment, carboxyl groups (either from the surface or from the protein) nay be derivatized using well known linkers (see the Pierce catalog). For example, carbodiimides activate carboxyl groups for attack by good nucleophiles such as amines (see Torchilin et al., Critical (Rev. Therapeutic Drug Carrier Systems, 7(4):275–308 (1991), expressly incorporated herein). In addition, library proteins may also be attached using other techniques known in the art, for example for the attachment of antibodies to polymers; see Slinkin et al., Bioconj. Chem. 2:342–348 (1991); Torchilin et al., supra; Trubetskoy et al., Bioconj. Chem. 3:323–327 (1992); King et al., Cancer Res. 54:6176–6185 (1994); and Wilbur et al., Bioconjugate Chem. 5:220–235 (1994), all of which are hereby expressly incorporated by reference). Similarly, when the library members are made recombinantly, the use of epitope tags (FLAG, etc.) or His6 tags allow the attachment of the members to the surface i.e. with antibody coated surfaces, metal (Ni) surfaces, etc.). In addition, labeling the library members with biotin or other binding partner pairs allows the use of avidin coated surfaces, etc. It should be understood that the proteins may be attached in a variety of ways, including those listed above. What is important is that manner of attachment does not significantly alter the functionality of the protein; that is, the protein should be attached in such a flexible manner as to allow its interaction with a target.

Once the biochips are made, they may be used in any number of formats for a wide variety of purposes, as will be appreciated by those in the art. For example, the scaffold protein serving as the library starting point may be an enzyme; by putting libraries of variants on a chip, the variants can be screened for increased activity by adding substrates, or for inhibitors. Similarly, variant libraries of ligand scaffolds can be screened for increased or decreased binding affinity to the binding partner, for example a cell surface receptor. Thus, in this embodiment, for example, the extracellular portion of the receptor can be added to the array and binding affinity tested under any number of conditions; for example, binding and/or activity may be tested under different pH conditions, different buffer, salt or reagent concentrations, different temperatures, in the presence of competitive binders, etc.

Thus, in a preferred embodiment, the methods comprise differential screening to identity bioactive molecules that are capable of either binding to the variant proteins and/or modulating the activity of the variant proteins. "Modulation" in this context includes both an increase in activity (e.g. enzymatic activity or binding affinity) and a decrease.

Another preferred embodiment utilizes differential screening to identify drug candidates that bind to the native protein, but cannot bind to modified proteins.

The most preferred embodiment utilizes differential screening to identify drug candidates that bind to the active variant protein, but can not bind to the inactive variant protein. As those skilled in the art will appreciate, there may be conditions where the most preferred embodiment would bind the closed but not the open.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the activity of the variant protein is increased; in another preferred embodiment, the activity of the variant protein is decreased. Thus, bioactive agents that are antagonists are preferred in some embodiments, and bioactive agents that are agonists may be preferred in other embodiments.

Thus, in a preferred embodiment, the biochips comprising the variant integrin or tertiary libraries are used to screen candidate agents for binding to library members. By "candidate bioactive agent" or "candidate drugs" or grammatical equivalents herein is meant any molecule, e.g. proteins (which herein includes proteins, polypeptides, and peptides), small organic or inorganic molecules, polysaccharides, polynucleotides, etc. which are to be tested against a particular target. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate agents, including the wide variety of known combinatorial chemistry-type libraries.

In a preferred embodiment, candidate agents are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate bioactive agents prior to the assay; only candidate agents that bind to the target need be identified. In addition, as is known in the art, coding tags using split synthesis reactions may be done, to essentially identify the chemical moieties on the beads.

Alternatively, a preferred embodiment utilizes libraries of natural compounds in the form of bacterial, fungal, plant and animal extracts that are available or readily produced, and can be attached to beads as is generally known in the art.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate bioactive agents include proteins, nucleic acids, and chemical moieties.

In a preferred embodiment, the candidate bioactive agents are proteins. In a preferred embodiment, the candidate bioactive agents are naturally occurring proteins or fragments of naturally occurring proteins. Thus, for example, cellular extracts containing proteins, or random or directed digests of proteinaceous cellular extracts, may be attached to beads as is more fully described below. In this way libraries of procaryotic and eucaryotic proteins may be made for screening against any number of targets. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By"randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents. In addition, the candidate agents may themselves be the product of the invention; that is, a library of proteinaceous candidate agents may be made using the methods of the invention.

The library should provide a sufficiently structurally diverse population of randomized agents to effect a probabilistically sufficient range of diversity to allow binding to a particular target. Accordingly, an interaction library must be large enough so that at least one of its members will have a structure that gives it affinity for the target. Although it is difficult to gauge the required absolute size of an interaction library, nature provides a hint with the immune response: a diversity of $10^{7-108}$ different antibodies provides at least one combination with sufficient affinity to interact with most potential antigens faced by an organism. Published in vitro selection techniques have also shown that a library size of $10^{7-108}$ is sufficient to find structures with affinity for the target. A library of all combinations of a peptide 7 to amino acids in length, such as generally proposed herein, has the potential to code for $20^7$ ($10^9$) to $20^{20}$. Thus, with libraries of $10^{7-108}$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

Thus, in a preferred embodiment, the invention provides biochips comprising libraries of variant proteins, with the library comprising at least about 100 different variants, with at least about 500 different variants being preferred, about 1000 different variants being particularly preferred and about 5000–10,000 being especially preferred.

In one embodiment, the candidate library is fully randomized, with no sequence preferences or constants at any position. In a preferred embodiment, the candidate library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate bioactive agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

In a preferred embodiment, the candidate bioactive agents are nucleic acids. See above for definition.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate bioactive agents are organic moieties. In this embodiment, as is generily described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, aeterocyclic compounds (including purines, pyrimidines, benzodiazepins, beta-lactams, tetracylines, ephalosporins, and carbohydrates), steroids (including estrogens, androgens, cortisone, ecodysone, atc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate agent at a time. Thus, the library of candidate agents used in any particular assay may include only one type of agent (i.e. peptides), or multiple types (peptides and organic agents).

Thus, in a preferred embodiment, the invention provides biochips comprising variant libraries of at least one scaffold protein, and methods of screening utilizing the biochips. Thus, for example, the invention provides completely defined libraries of variant scaffold proteins having a defined set number, wherein at least 85–90–95% of the possible members are present in the library.

In addition, as will also be appreciated by those in the art, the biochips of the invention may be part of HTS system utilizing any number of components. Fully robotic or microfluidic systems include automated liquid-, particle-, cell- and organism-handling including high throughput pipetting to perform all steps of gene targeting and recombination applications. This includes liquid, particle, cell, and organism manipulations such as aspiration, dispensing, mixing, diluting, washing, accurate volumetric transfers; retrieving, and discarding of pipes tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

The system used can include a computer workstation comprising a microprocessor programmed to manipulate a device selected from the group consisting of a thermocycler, a multichannel pipettor, a sample handler, a plate handler, a gel loading system, an automated transformation system, a gene sequencer. a colony picker, a bead picker, a cell sorter, an incubator, a light microscope, a fluorescence microscope, a spectrofluorimeter, a spectrophotometer, a luminometer, a CCD camera and combinations thereof.

In a preferred embodiment, the methods of the invention are used to generate variant libraries to facilitate and correlate single nucleotide polymorphism (SNP) analysis. That is, by drawing on known SNP data and determining the effect of the SNP on the protein, information concerning SNP analysis can be determined. Thus, for example, making a "sequence alignment" of sorts using known SNPs can result in a probability distribution table that can be used to design all possible SNP variants, which can then be put on a biochip and tested for activity and effect.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE 1

Design And Characterization of Novel Variant Integrin Proteins by PDA

Summary: Sequences for a variant integrin activity proteins were designed by simultaneously optimizing residues in the buried core of the protein using Protein Design Automation (PDA) as described in WO98/47089, U.S. Ser. Nos. 09/058,459, 09/127,926, 60/104,612, 60/158,700, 09/419,351, 60/181,630, 60/186,904, and U.S patent application, entitled Protein Design Automation For Protein Libraries (Filed: Apr. 14, 2000; Inventor: Bassil Dahiyat), all of which are expressly incorporated by reference in their entirety. Several core designs were completed either with stabilized open or closed conformations of the protein. Up to 45 of the 184 residues that make up the I domain were allowed variability for both mutations and rotamer conformation. Predicted stabilized open and stabilized closed I domains, either incorporated in complete integrin proteins or in isolation, were then made and tested to determine the binding ability of the novel integrin proteins. Table 1 shows the mutations for the examined sequences for each of the novel I domains and integrins containing I domains that were tested for binding activity.

Computational Design

In order to stabilize the alphaM I domain in its open (active, high affinity, or 1ido conformation) or in its closed (inactive, low affinity, or 1jlm conformation) a computational protein design algorithm called ORBIT (Optimization of Rotamers By Iterative Techniques) that selects amino acid sequences that are optimal for a target fold (Dahiyat, B. I. & Mayo, S. L. Science 278, 82–87 (1997); Street, A. G. & Mayo, S. L. Structure 7:R105–R109 (1999); Gordon, et al. Curr. Opin. Struct. Biol. 9:509–513 (1999).) was used. The algorithm considers pairwise interaction energies between amino acid side chains and between the side chains and the protein backbone. The interaction energies are calculated according to an empirical energy function that contains terms for van der Waals, electrostatics, hydrogen bonding, and salvation. Amino acids are represented with a discrete set of allowed side chain conformations, called rotamers. The resulting rotamer-space optimization problem has a combinatorial complexity here of up to $6 \times 10^{100}$, and was solved using the dead-end elimination theorem (Lasters, et al. Protein Eng. 8:815–822 (1995)). In order to prevent mutations that could directly affect binding of ligands such as iC3b, the design procedure was limited to residues in the protein's hydrophobic core. Core residues near the $Mg^{2+}$ of the MIDAS, or that are partially exposed and near the bottom of the I-domain where they may interact with the putative integrin b-propeller domain, were also kept as wild type. Out of 184 residues in the Mac-1 I-domain, 40 to 45 hydrophobic core residues were included in the calculations.

Computational details, potential functions, and methods for defining core residues are as described (Dahiyat, B. I. & Mayo, S. L. Science 278, 82–87 (1997);Dahiyat, B. I. & Mayo, S. L. Proc. Natl. Acad. Sci. U.S. A. 94:10172–10177 (1997);Dahiyat, B. I. & Mayo, S. L. Protein Sci. 5:895–903 (1996); Dahiyat, et al., Protein Sci. 6:1333–1337 (1997); Street, A. G. & Mayo, S. L. Fold Des. 3:253–258 (1998)). A scale factor of 0.9 was used for all van der Waals radii (Dill, K. A. Biochemistry 29:7133–7155 (1990)). "Solvation potential 1" utilized 23.2 cal/mol/$Å^2$ to benefit hydrophobic burial (Dahiyat, et al., Protein Sci. 6:1333–1337 (1997)) and a hydrophobic exposure penalty of the same magnitude to penalize residual hydrophobic exposure (Dill, K. A. Biochemistry 29:7133–7155 (1990)). "Solvation potential 2"(Casimiro, et al., Biochemistry 34:6640–6648 (1995)) utilized 48.0 cal/mol/$Å^2$ for the hydrophobic burial benefit and an exposure penalty 1.6 times the magnitude of the burial benefit. Energies for polar surface area burial were not included in any of the calculations; however, a penalty of 2.0 kcal/mol was applied to the burial of polar hydrogens not involved in hydrogen bonds (Street, A. G. & Mayo, S. L. Fold Des. 3:253–258 (1998)).

Out of 184 residues in the Mac-1 I-domain (D132-K315), 56 were initially defined as core residues. Rresidues 176 and 267, both hydrogen-bonded tyrosines; and residues Phe 234, Ile 265, Val 296 and Leu 305, partially exposed and near the bottom of the I domain where they may interact with the beta-propeller domain of integrins, were excluded from the calculations. For calculation q, the 42 residues Ile 135, Ala 136, Phe 137, Leu 138, Ile 139, Ile 145, Phe 150, Phe 156, Val 157, Val 160, Leu 164, Phe 171, Leu 173, Phe 186, Val 199, Ile 202, Ala 212, Ile 215, Val 218, Val 219, Leu 222, Phe 223, Ala 229, Ala 233, Leu 237, Val 238, Val 239, Ile 240, Val 255, Ala 259, Val 264, Val 268, Ile 269, Val 271, Ala 274, Leu 284, Ile 287, Ala 288, Val 299, Ala 304, Ile 308, and Leu 312 were allowed to become Ala, Val, Leu, Ile, Phe, Tyr, or Trp; and the three residues Met 153, Met 161, and Met 174 were allowed to be Ala, Val, Leu, Ile, Met, Phe, Tyr, or Trp. Residues Leu 170, Phe 189, Leu 198, Ile 236, and Phe 297 had some solvent exposure and were not allowed to mutate but were allowed to change rotamer. The same residues were used for calculation r, except three residues in the C-terminal alpha-helix, Ala 304, Ile 308, and Leu 312, were not allowed to mutate but were allowed to change rotamer. In the jlm2r calculation, we used the same core residues as in the r calculation except for omitting Val 271 and Ala 274 that are surface-exposed in the 1jlm structure.

Four mutant sequences (SEQ ID NOS:3–8) each were computed based on the open 1ido structure and the closed 1jlm structure using two different solvation potentials and subsets of core residues. Three out of a total of four designed ido mutants were well expressed; all have unique amino acid substitutions (Table 1). Fewer substitutions were predicted for jlm mutants, and only one of these, jlm2r (SEQ ID NO:6), was tested. All mutated sidechains are buried in the core of the I domain and are distant from the MIDAS and from the residues critical for iC3b binding(Li, R., et al. J. Cell Biol. 143:1523–1534 (1998); Zhang, L & Plow, E. F. Biochemistry 38:8064–8071 (1999)), which are located on the top of the I-domain (FIG. 1). Thus, the mutated residues cannot directly affect binding of iC3b. The energies of the selected sequences were determined in both the 1ido and 1jlm backbones (Table 1). All of the mutant sequences had energies that were lower than wild-type in the desired backbone configuration, and higher than wild-typo in the undesired configuration. Thus, the open ido1q, 1do1r, and ido2r mutants (SEQ ID NOS:3–5) both stabilized the alphaM I domain in the 1ido conformation and destabilized it in the 1jlm. conformation (Harbury, et al. Science 282:1462–1467 (1998)). Similar results were obtained regardless of the solvalion potential used in the calculation. The energy of the wild-type sequence was lower in the 1jlm structure than in the lido structure, and thus the wild-type sequence should favor the 1jlm conformation (Table 1). This is consistent with the finding that for all alphaM, alphaL, alpha2 and alpha1 I-domain crystal structures determined to date, the I domain assumes a closed, 1jlm-like structure in the absence of a bound ligand or pseudo-ligand(Lee, et al., Cell 80:631–638 (1995); Qu, A. & Leahy, D. J. Proc. Natl. Acad. Sci. U.S.A. 92:10277–10281 (1995); Qu, A. & Leahy, D. J. Structure 4:931–942 (1996); Emsley, et al., J. Biol. Chem. 272:28512–28517 (1997); Baldwin, E. T. at al. Structure 6:923–935 (1998); Nolte, M. at al. FEBS Lett. 452:379–385 (1999); Rich, R. L. et al. J. Biol. Chem. 274:24906–24913 (1999).

Ligand Binding by Designed I-domains within alphaMbeta2 (aMb2)

The function of mutant I domains was first examined within intact Mac-1 alphaMbeta2 heterodimers in transfected cells. Formation of alphaMbeta2, heterodimers was confirmed by monoclonal antibody CBRM1/20, which recognizes an epitope in the putative beta-propeller domain of the alphaM subunit only after association with the beta2 subunit (Oxvig, C. & Springer, T. A. Proc. Natl. Acad. Sci. U.S.A. 95:4870–4875 (1998); Lu, C., Oxvig, C. & Springer, T. A. J. Biol. Chem. 273:15138–15147 (1998)). Monoclonal antibody CBRM1/5, which binds to a region of the I domain near the MIDAS that undergoes shape-shifting and only recognizes activated aMb2 (Oxvig, et al. Proc. Natl. Acad. Sci. U.S.A. 96:2215–2220 (1999); Diamond, M. S. & Springer, T. A. J. Cell Biol. 120:545–556 (1993)), was used as a probe of I domain activation. Binding of CBRM1/5 monoclonal antibody was increased 2 to 4 fold in the three designed open mutants, and slightly decreased in the designed closed mutant (FIG. 2*a*). Ligand binding was examined by adhesion of 293T cell transfectants to iC3b immobilized in microtiter plates. Wild-type beta2-integrins including aMb2 and aLb2 are basally active in 293T cells (Oxvig, et al. Proc. Natl. Acad. Sci. U.S.A. 96:2215–2220 (1999); Lu, C. & Springer, T. A. J. Immunol. 159:268–278 (1997)). Nonetheless, bindings of all designed open mutants to iC3b was greater than that of wild-type and was comparable to that of wild-type Mac-1 activated by monoclonal antibody CBR LFA1/2 to the beta2 subunit (Petruzzelli, et al. J. Immunol. 155:854–866 (1995)) (FIG. 2*b*). By contrast, the designed closed mutant bound less than wild-type (FIG. 2*b*).

The function of designed I domains within intact aMb2 was further investigated in stably transfected K562 cells (FIG. 3), in which aMb2 shows little basal activity (Oxvig, et al. Proc. Natl. Acad. Sci. U.S.A. 96:2215–2220 (1999); Lu, C. & Springer, T. A. J. Immunol. 159:268–278 (1997)). aMb2 heterodimers containing wild-type or the designed closed mutant I domain showed little expression of the CBRM1/5 activation epitope (FIGS. 3*a, b*) or binding to iC3b (FIG. 3*c*). By contrast, aMb2 containing designed open mutant I domains showed marked expression of the CBRM1/5 epitope (FIGS. 3*a, b*) and binding to iC3b (FIG. 3*c*). Binding to iC3b was increased 10 to 13-fold relative to wild-type and was similar to binding in the presence of the activating monoclonal antibody CBR LFA-1/2 (FIG. 3*c*). Binding of the designed open mutants to iC3b appeared to be maximal, because it could not be further increased by the activating monoclonal antibody CBR LFA-1/2 (FIG. 3*d*). The alphaMbeta2 heterodimer containing the designed closed mutant I domain was resistant to activation; binding to iC3b activated by CBR LFA-1/2 monoclonal antibody was reduced 85% for jlm2r compared to wild-type (FIG. 3D). All mutant and wild-type heterodimers bound CBR LFA-1/2 monoclonal antibody equally well (not shown). All binding was specific, since it was completely inhibited by monoclonal antibody CBRM1/5 (FIG. 3D) As is demonstrated in this example, the binding properties of entire integrin proteins can be manipulated to either increase the variant protein's binding ability or decrease it.

Plasmid Construction and Mutagenesis

Recursive PCR with 10 overlapping oligonucleotides (Casimiro, et al., Biochemistry 34:6640–6648 (1995); Prodromou, C. & Pearl, L. H. Protein Engineering 5:827–829 (1992)) was used to construct a 649 bp I domain mutant DNA fragment. Unique BamHI and KpnI sites were introduced at nucleotide positions 451 and 1681, respectively, using silent mutations. The PCR products containing mutated I domain cDNA fragments were cut with BamHI and KpnI and swapped into wild-type alphaM cDNA. Human beta2 subunit cDNA (Kishimoto, et al. Cell 48:681–690 (1987)) was subcloned into pcDNA3.1(+). To construct isolated, cell-surface I domains, the signal peptide and following 9 bp from the 5' end of alphaM were ligated to the sequence G127-P348 containing the I domain. HindIII and SalI sites were introduced immediately adjacent to the 5' and 3' ends of this fragment, respectively. The HindIII-SalI fragment was subcloned in frame with and 5' to a c-myc tag and the PDGFR transmembrane domain in vector pDisplay™ (Invitrogen) and further subcloned into pcDNA3.1/Hygro. All DNA amplification was carried out with Pfu DNA polymerase (Stratagene) and the final constructs were verified by sequencing.

Cell lines and transfection. 293T cells were maintained and transfected by calcium phosphate coprecipitation (Oxvig, et al. Proc. Natl. Acad. Sci. U.S.A. 96:2215–2220 (1999)) by using 12 micrograms of alpha subunit and 8 micrograms of beta subunit cDNA or 10 microgras I domain-PDGFR cDNA. After 48 h, cells were detached with 5 mM EDTA in PBS and subjected to flow cytometry or adhesion assays.

For stable K562 cell lines, 2 micrograms of SspI-linearized pcDNA3.1/Hygro(+) containing the alphaM cDNA was cotransfected with 20 micrograms of the SspI-linearized wild-type beta2 cDNA in pcDNA3.1(+) by electroporation as described (Oxvig, et al. Proc. Natl. Acad. Sci. U.S.A. 96:2215–2220 (1999); Lu, C. & Springer, T. A. J. Immunol. 159:268–278 (1997)).

Immunofluorescence flow-cytometry was described (Lu, et al. J. Biol. Chem. 273:15138–15147 (1998)).

Binding of Transfectants to Immobilized iC3b

Binding of fluorescently labeled cells to human complement component iC3b immobilized in flat-bottomed 96-well plates was as described (Oxvig, et al. Proc. Natl. Acad. Sci. U.S.A. 96:2215–2220 (1999); Lu, C. & Springer, T. A. J. Immunol. 159:268–278 (1997)) except plates were blocked with 2% non-fat milk in PBS; and binding assays using 293T cell transfectants were performed at room temperature.

EXAMPLE 2

Design and Characterization of Novel I Domain Proteins by PDA

The ability of variant I domains to bind in isolation of the rest of the variant integrin protein is also possible through these novel proteins.

Work with the integrin alphaLbeta2 has shown that when an isolated I domain is expressed on the cell surface, ligand binding is much weaker than with an intact integrin and is only detected when the I domain is expressed at very high levels (Knorr, R. & Dustin, M. L. J. Exp. Med. 186:719–730 (1997)). Since shape-shifting in I-domains is proposed to be related to conformational movements elsewhere in integrins (Springer, T. A. Proc. Natl. Acad. Sci. U.S.A. 94:65–72 (1997)), it was important to examine ligand binding by the variant I domains in isolation from other integrin domains. Therefore, mutant alphaM I domains (the same domains as described in EXAMPLE 1) were expressed transiently on the surface of 293T cells or stably on K562 cells after fusion to an N-terminal signal sequence and a C-terminal platelet-derived growth factor receptor (PDGFR) transmembrane domain. Wild-type I-domain and designed closed I-domain showed essentially no binding to iC3b (FIGS. 4a, b). By contrast, designed open mutant I-domains expressed at the same level on the cell surface gave robust binding to iC3b (FIGS. 4a, b), and binding was enhanced by addition of $Mn^{2+}$ (FIG. 4b). Furthermore, binding was completely inhibited by EDTA, showing that ligand binding was dependent on the MIDAS (FIG. 4c). As is demonstrated by this example, a variant I domain can be produced which is able to bind without the rest of the variant integrin protein.

We claim:

1. A non-naturally occurring integrin protein comprising thirteen amino acid substitutions as compared to the human integrin protein of SEQ ID NO:1, said substitutions comprising amino acid substitutions F156L, V160I, V199I, I215L, V238F, V239L, I240L, A259L, I269L, V271F, I287V, V299A, and I308V and comprising the amino acid sequence of SEQ ID NO.:3.

2. A non-naturally occurring integrin protein comprising nine amino acid substitutions as compared to the human integrin protein of SEQ ID NO:1, said substitutions comprising amino acid substitutions F156W, V199I, I215L, V238F, V239L, I240L, A259L, I287V, and V299I and comprising the amino acid sequence of SEQ ID NO.:4.

3. A non-naturally occurring integrin protein comprising eight amino acid substitutions as compared to the human integrin protein of SEQ ID NO:1, said substitutions comprising amino acid substitutions I139V, M153A, V157I, V199I, V238I, V239L, I287V, and V299I and comprising the amino acid seauence of SEQ ID NO.:5.

4. A non-naturally occurring integrin protein comprising four amino acid substitutions as comnared to the human integrin protein of SEQ ID NO:1, said substitutions comprising amino acid substitutions I215V, V219I, F223L, and V238I and comprising the amino acid seouence of SEQ ID NO.:6.

* * * * *